US012703721B2

(12) United States Patent
Marshall et al.

(10) Patent No.: US 12,703,721 B2
(45) **Date of Patent: *Aug. 11, 2026**

(54) CONFORMATIONALLY STABILIZED RSV PRE-FUSION F PROTEINS

(71) Applicant: Calder Biosciences Inc., New York, NY (US)

(72) Inventors: Christopher Marshall, New York, NY (US); Mark Yondola, New York, NY (US); Roberto Mariani, New York, NY (US); Aaron Zomback, Cheshire, CT (US); Sonal Gidwani, New York, NY (US)

( * ) Notice: Subject to any disclaimer, the term of this patent is extended or adjusted under 35 U.S.C. 154(b) by 134 days.

This patent is subject to a terminal disclaimer.

(21) Appl. No.: 18/601,398

(22) Filed: Mar. 11, 2024

(65) Prior Publication Data

US 2025/0092094 A1 Mar. 20, 2025

Related U.S. Application Data

(63) Continuation of application No. 17/668,287, filed on Feb. 9, 2022, now Pat. No. 11,926,649, which is a continuation of application No. 16/637,155, filed as application No. PCT/US2018/045463 on Aug. 7, 2018, now Pat. No. 11,267,848.

(60) Provisional application No. 62/674,791, filed on May 22, 2018, provisional application No. 62/640,467, filed on Mar. 8, 2018, provisional application No. 62/629,685, filed on Feb. 12, 2018, provisional application No. 62/542,247, filed on Aug. 7, 2017.

(51) Int. Cl.

| | |
|---|---|
| ***C07K 14/005*** | (2006.01) |
| ***A61K 39/155*** | (2006.01) |
| ***A61P 31/14*** | (2006.01) |
| ***C12N 7/00*** | (2006.01) |

(52) U.S. Cl.

CPC .......... *C07K 14/005* (2013.01); *A61K 39/155* (2013.01); *A61P 31/14* (2018.01); *C12N 7/00* (2013.01); *C12N 2760/18522* (2013.01); *C12N 2760/18534* (2013.01); *C12N 2760/18571* (2013.01)

(58) Field of Classification Search

None

See application file for complete search history.

(56) References Cited

U.S. PATENT DOCUMENTS

| | | | | |
|---|---|---|---|---|
| 10,125,172 | B2 * | 11/2018 | Marshall | A61P 31/12 |
| 11,267,848 | B2 * | 3/2022 | Marshall | A61P 31/14 |
| 11,926,649 | B2 * | 3/2024 | Marshall | A61K 39/155 |
| 2015/0030622 | A1 * | 1/2015 | Marshall | C07K 14/005 530/350 |

* cited by examiner

*Primary Examiner* — Shanon A. Foley
*Assistant Examiner* — Myron G Hill
(74) *Attorney, Agent, or Firm* — GRIMES & YVON LLP

(57) ABSTRACT

The present invention provides mutant RSV F molecules, such as those that can be, or are stabilized, in a pre-fusion conformation by the introduction of one or more DT cross-links. The present invention also provides methods of making such mutant RSV F molecules, compositions comprising such mutant RSV F molecules, and methods of use of such mutant RSV F molecules, for example in vaccination methods, therapeutic methods, and antibody production methods.

20 Claims, 11 Drawing Sheets

Specification includes a Sequence Listing.

Fig. 3A-B

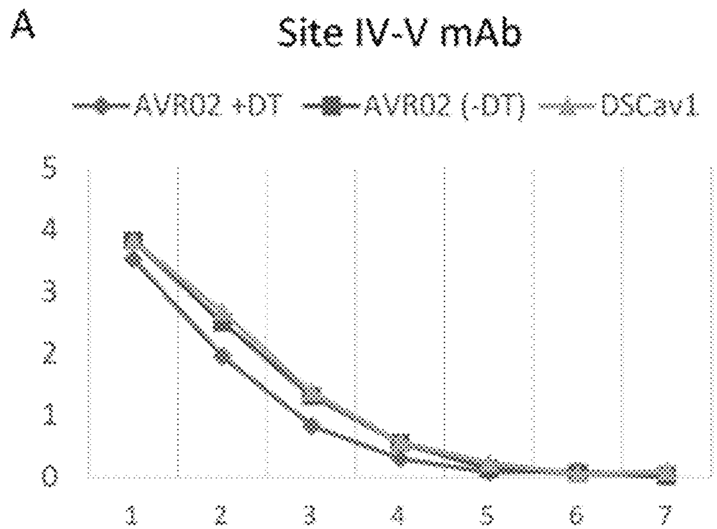
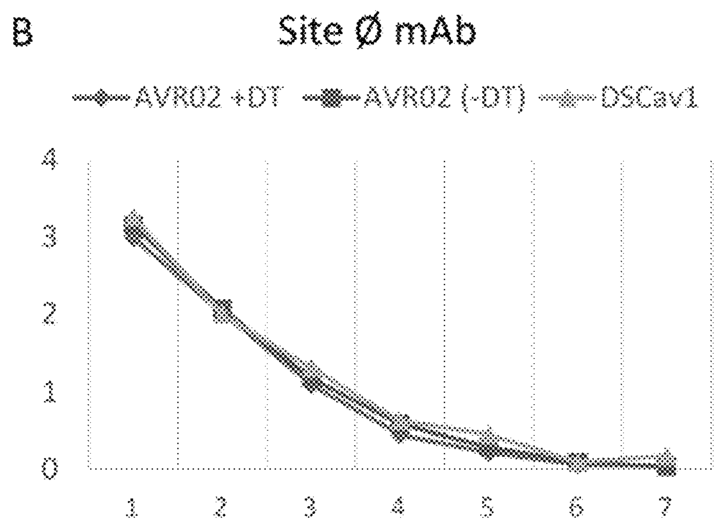
Fig 5 A-B

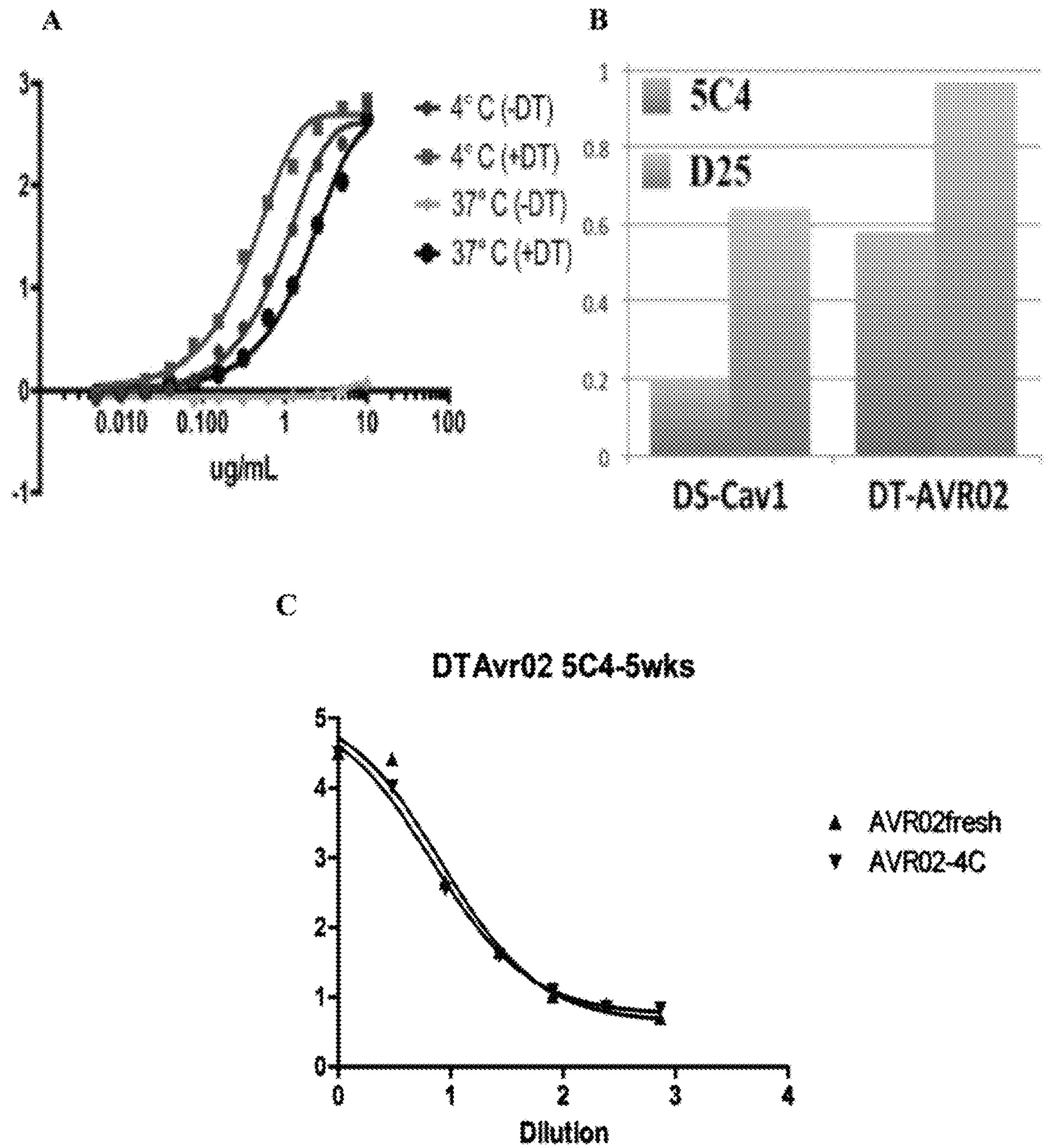
Fig. 6A-C

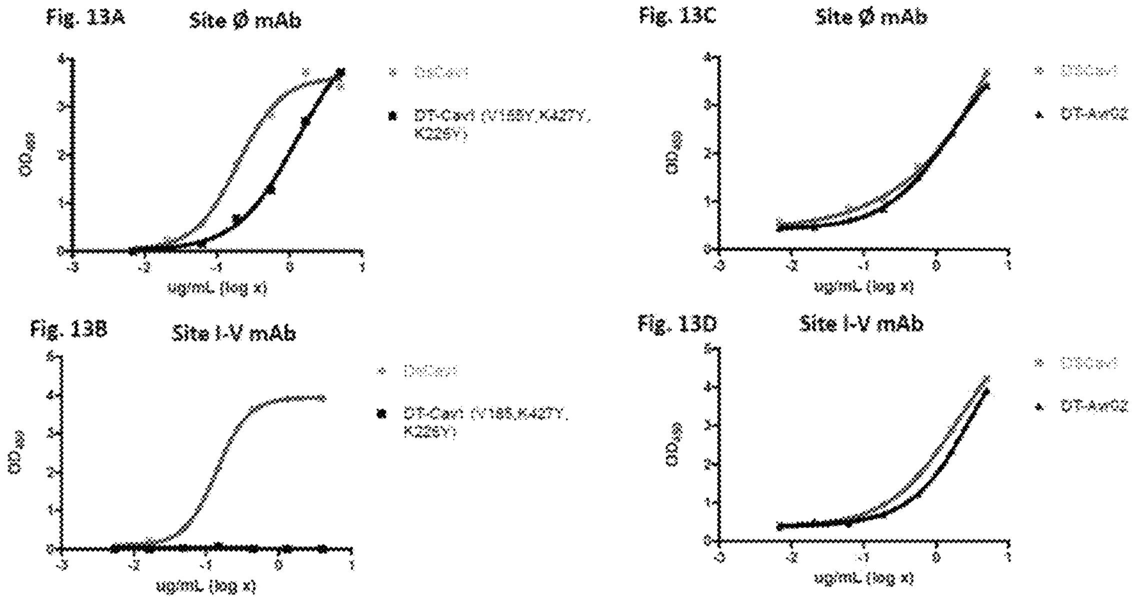
Fig. 13A-D
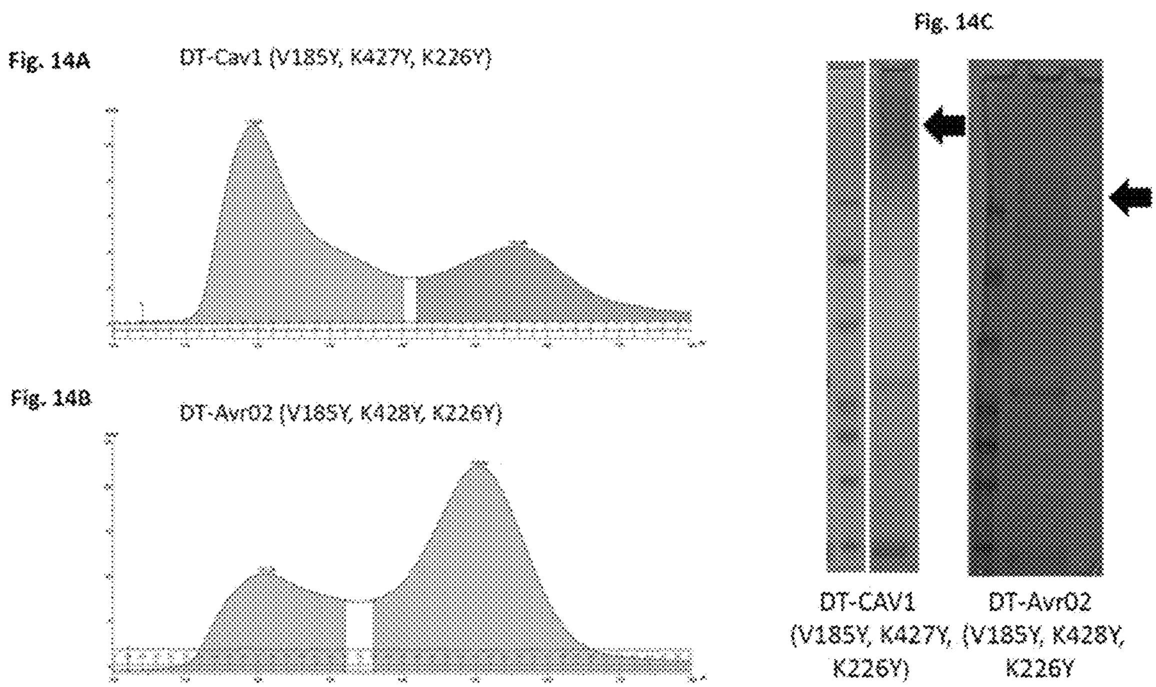
Fig. 14A-C

A
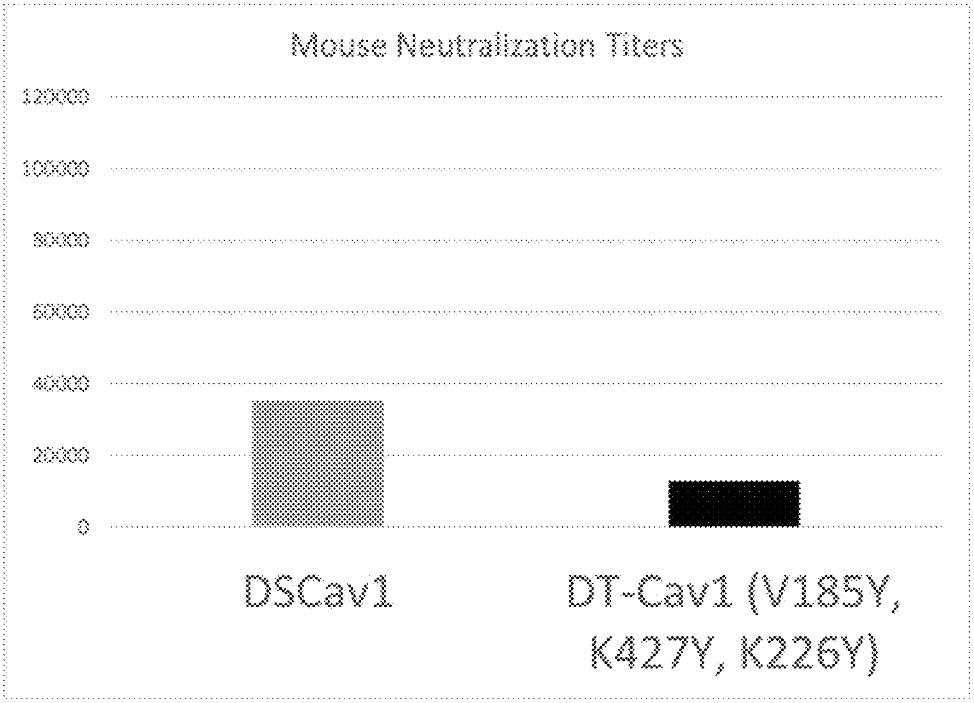
B
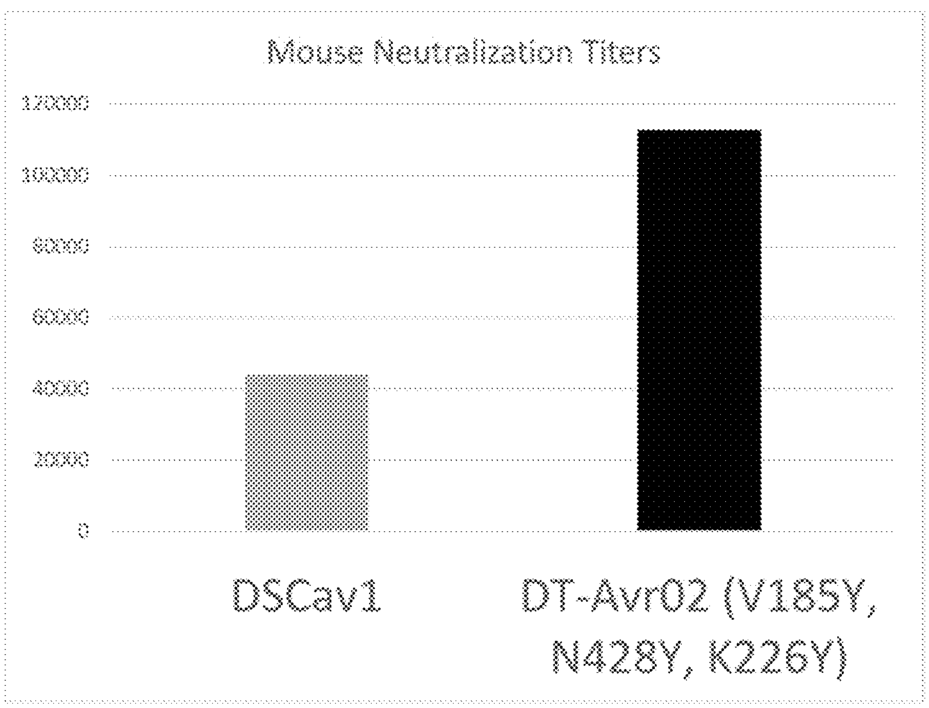
Fig. 15A-B

A
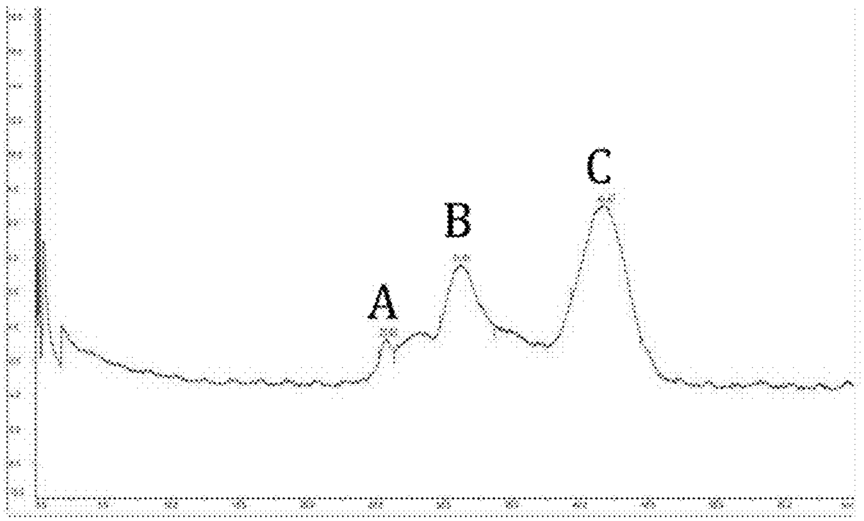
B
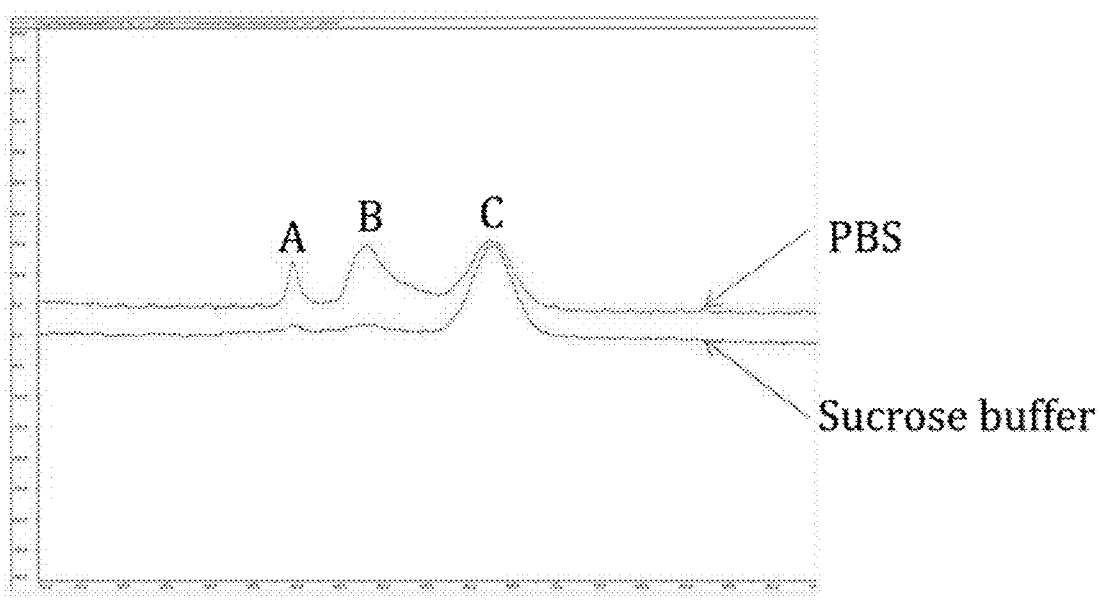
Fig. 16A-B

CONFORMATIONALLY STABILIZED RSV PRE-FUSION F PROTEINS

CROSS-REFERENCE TO RELATED APPLICATIONS

This application is a continuation of U.S. patent application Ser. No. 17/668,287, filed on Feb. 9, 2022, which is a continuation of U.S. patent application Ser. No. 16/637,155, filed on Feb. 6, 2020, now U.S. Patent No, 11,267,848, which is a U.S. national stage entry under 35 U.S.C. 371 of International Patent Application PCT/US2018/045463, filed on Aug. 7, 2018, and claims the benefit of priority of U.S. Provisional Patent Application No. 62/542,247, filed on Aug. 7, 2017, U.S. Provisional Patent Application No. 62/629,685, filed on Feb. 12, 2018, U.S. Provisional Patent Application No. 62/640,467, filed on Mar. 8, 2018, and U.S. Provisional Patent Application No. 62/674,791, filed on May 22, 2018, the complete contents of each of which patent applications are hereby incorporated by reference in their entireties.

STATEMENT REGARDING FEDERALLY SPONSORED RESEARCH

This invention was made with government support under grant number AI112124 awarded by the National Institutes of Health. The government has certain rights in the invention.

SEQUENCE LISTING

The instant application contains a Sequence Listing which has been filed electronically in XML file format and is hereby incorporated by reference in its entirety. Said XML copy, created on Nov. 15, 2024, is named CALDER_009_US3_SL.xml and is 154,378 bytes in size.

INCORPORATION-BY-REFERENCE

For the purposes of only those jurisdictions that permit incorporation by reference, the content of all documents cited herein is hereby incorporated by reference in its entirety.

BACKGROUND OF THE INVENTION

Each year respiratory syncytial virus (RSV) infects 4-5 million children in the U.S. and is the leading cause of infant hospitalizations (~150,000 hospitalizations). Globally, it accounts for 6.7% of deaths in infants less than 1 year old, second only to malaria. In addition, it poses a serious threat to other high-risk groups, including elderly and immunocompromised subjects, where it results in approximately an additional 180,000 hospitalizations and 12,000 deaths in the U.S. There are no current frontline treatments for RSV, and the only currently approved prophylactic treatment for RSV is passive administration of the licensed monoclonal antibody Synagis (palivizumab), which recognizes the RSV fusion (F) protein, and reduces incidence of severe disease by only ~50%. The high cost of prophylaxis with Synagis limits its use only to premature infants and infants less than 24 months old with congenital heart disease. For a review see Costello et al., "Targeting RSV with Vaccines and Small Molecule Drugs, Infectious Disorders," Drug Targets, 2012, vol. 12, no. 2. The development of a more effective and, ideally, more cost-effective RSV vaccine would be of enormous value.

The RSV F protein is an RSV envelope glycoprotein. In nature the RSV F protein is translated as a single precursor polypeptide—designated "F0". The F0 precursor polypeptide is generally 574 amino acids in length, of which amino acids 1-25 comprise a signal peptide. The precursor polypeptide F0 forms a precursor trimer, which is proteolytically cleaved by cellular proteases to yield a Pep 27 polypeptide, an F1 polypeptide and an F2 polypeptide. The F2 polypeptide typically contains amino acid residues 26-109 of the F0 precursor. The F1 polypeptide typically contains amino acid residues 137-574 of the F0 precursor. The F1 and F2 polypeptides are linked by disulfide-bonds to form a heterodimer which is referred to as an RSV F "protomer." Three such protomers form the mature trimeric form of the RSV F molecule.

The RSV F protein is known to induce potent neutralizing antibodies that correlate with protection against RSV. Recently it has been shown that the pre-fusion conformation of the RSV F protein trimer (which may be referred to as "pre-fusion F" or "pre-F" herein) is the primary determinant of neutralizing activity in human sera. Also, the most potent neutralizing antibodies (nAbs) isolated to date specifically bind only to the pre-fusion conformation. However, soluble pre-F is highly unstable and readily transitions to the post-fusion conformation—limiting its usefulness as a vaccine immunogen.

An RSV F protein stabilized in its pre-fusion conformation could be very valuable—providing a candidate RSV vaccine immunogen.

The crystal structure of the RSV F protein (bound to a potent neutralizing Ab-D25) in its pre-fusion conformation was described in Mclellan et al., 2013, Science, 340, p. 1113-1117, the contents of which are hereby incorporated by reference in their entirety.

Several different approaches have been developed with the aim of trying to stabilize RSV F its pre-F conformation. For example, Marshall et al. previously described introducing "to tyrosine" point mutations and dityrosine (DT) crosslinks at certain specified positions in the RSV F protein. See International Patent Application No. PCT/US2014/048086. Other approaches have included introducing "to cysteine" mutations, di-sulfide bonds, and/or cavity-filling amino acid substitutions at certain specified positions in the RSV F protein. See U.S. Pat. Nos. 9,738,689, 9,950,058, or Mclellan et al. (2013) Science 342:592-598.

BRIEF SUMMARY OF THE INVENTION

The present invention provides certain new developments and improvements over and above the work described previously by Marshall et al. in patent application PCT/US2014/048086, including, but not limited to, providing certain new mutant RSV F molecules that are not described in PCT/US2014/048086 and that have improved properties as compared to the molecules described in PCT/US2014/048086—as well as compared to other RSV F mutants and RSV F candidate immunogens. As illustrated in the Examples section of this patent disclosure, when these new mutant RSV F molecules are administered to animals in vivo using accepted preclinical animal models, they are highly immunogenic.

In some embodiments the present invention provides mutant RSV F molecules that comprise a point mutation to tyrosine (abbreviated to "Tyr" or "Y" according to standard conventions) at amino acid position 428—i.e. a "428Y mutation." As described further in the Examples section of this patent disclosure, mutant RSV F molecules comprising such a 428Y mutation (referred to as "428Y mutants") have improved properties as compared to mutant RSV F molecules that are otherwise identical but that comprise a 427Y mutation instead of a 428Y mutation. These improved properties include: (i) an approximately five-fold increase in serum neutralization titers following vaccination, (ii) a markedly improved antigenic profile as determined by binding to antibodies specific for antigenic site IV-V and antibodies specific for the pre-fusion specific antigenic site Ø, and (iii) a marked increase in the production of RSV F trimeric complexes as compared to hexameric complexes. Building on these discoveries, the present invention provides various new and improved mutant RSV F molecules including, but not limited to, mature RSV F trimers, mature RSV F trimers that are conformationally locked in the pre-fusion conformation by one or more DT cross links, various precursors thereof, and various components thereof (including F1 and F2 polypeptides and protomers). The present invention also provides amino acid sequences of such mutant RSV F molecules, nucleotide sequences that encode such mutant RSV F molecules, vectors a that comprise such nucleotide sequences, cells that comprise and/or express such nucleotide sequences or vectors, methods of making such mutant RSV F molecules, and methods of use of such mutant RSV F molecules—including, but not limited to, uses in vivo for vaccination against RSV and uses as immunogens for antibody production.

Accordingly, in one embodiment, the present invention provides mutant RSV F molecules that comprise a point-mutation to-tyrosine at amino acid position 428 (i.e. a 428Y mutation) or at an amino acid position that corresponds to position 428—for example as determined by alignment to, and/or using the amino acid numbering of SEQ ID NO. 1. In some embodiments such mutant RSV F molecules are, or comprise, RSV F monomers or protomers—each monomer or protomer comprising a 428Y mutation. In some embodiments such mutant RSV F molecules are, or comprise, RSV F trimers (e.g. mature RSV F trimers)—each trimer comprising three 428Y mutations.

In some embodiments, such mutant RSV F molecules comprising a 428Y mutation also comprise a point mutation to tyrosine at amino acid position 226 (i.e. a 226Y mutation), or at an amino acid position that corresponds to position 226—for example as determined by alignment to, and/or using the amino acid numbering of, SEQ ID NO. 1. In some embodiments such mutant RSV F molecules are, or comprise, RSV F monomers or protomers—each monomer or protomer comprising both a 428Y mutation and a 226Y mutation. In some embodiments such mutant RSV F molecules are, or comprise, RSV F trimers (e.g. mature RSV F trimers)—each trimer comprising three 428Y mutations and three 226Y mutations.

In some embodiments, such mutant RSV F molecules comprising a 428Y mutation also comprise a point mutation to tyrosine at amino acid position 185 (i.e. a 185Y mutation), or at an amino acid position that corresponds to position 185—for example as determined by alignment to, and/or using the amino acid numbering of, SEQ ID NO. 1. In some embodiments such mutant RSV F molecules are, or comprise, RSV F monomers or protomers—each monomer or protomer comprising both a 428Y mutation and a 185Y mutation. In some embodiments such mutant RSV F molecules are, or comprise, RSV F trimers (e.g. mature RSV F trimers)—each trimer comprising three 428Y mutations and three 185Y mutations.

In some embodiments such mutant RSV F molecules comprising a 428Y mutation also comprise both: (a) a point mutation to tyrosine at amino acid position 226 (i.e. a 226Y mutation), or at an amino acid position that corresponds to position 226—for example as determined by alignment to, and/or using the amino acid numbering of, SEQ ID NO.1, and (b) a point mutation to tyrosine at amino acid position 185 (i.e. a 185Y mutation), or at an amino acid position that corresponds to position 185—for example as determined by alignment to, and/or using the amino acid numbering of, SEQ ID NO.1. In some embodiments such mutant RSV F molecules are, or comprise, RSV F monomers or protomers—each monomer or protomer comprising a 428Y mutation, a 226Y mutation and a 185Y mutation. In some embodiments such mutant RSV F molecules are, or comprise, RSV F trimers (e.g. mature RSV F trimers)—each trimer comprising three 428Y mutations, three 226Y mutations, and three 185Y mutations.

Each of the various mutant RSV F molecules described above, and elsewhere herein, can also comprise various other mutations.

In some embodiments the mutant RSV F molecules described herein also comprise one or more additional to-tyrosine mutations—such as one or more of the to-tyrosine mutations described in International Patent Application No. PCT/US2014/048086 (Publication No. WO/2015/013551)—the contents of which are hereby incorporated by reference.

In some embodiments the mutant RSV F molecules described herein also comprise one or more to-cysteine mutations—such as one or more or those described in U.S. Pat. Nos. 9,738,689, 9,950,058, or Mclellan et al. (2013) Science 342:592-598, each of which is hereby incorporated by reference. In some such embodiments the RSV F molecules comprise so-called "DS" mutation(s)—as described in U.S. Pat. No. 9,738,689, U.S. Pat. No. 9,950,058, or Mclellan et al. (2013) Science 342:592-598. For example, in some embodiments, the RSV F molecules comprise a 155C mutation, a 290C mutation, or both a 155C and 290C mutation.

In some embodiments the mutant RSV F molecules described herein also comprise one or more cavity-filling amino acid substitutions—such as one or more or those described in U.S. Pat. Nos. 9,738,689, 9,950,058, or Mclellan et al. (2013) Science 342:592-598, each of which is hereby incorporated by reference. In some such embodiments the RSV F molecules comprise so-called "Cav1" mutation(s)—as described in U.S. Patent No. 9,738, 689, U.S. Pat. No. 9,950,058, or Mclellan et al. (2013) Science 342:592-598. For example, in some embodiments, the RSV F molecules comprise a S19OF cavity-filling mutation, a V207L cavity-filling mutation, or both a S190F and V207L cavity-filling mutation.

In some embodiments the mutant RSV F molecules described herein further comprise a heterologous trimerization domain. In some of such embodiments, the trimerization domain is a foldon domain.

In some embodiments the mutant RSV F molecules described herein further comprise one or more tags that may be useful for the detection and/or purification of the RSV F molecules. In some embodiments such tags may be cleavable tags. In some of such embodiments, the tag is a His tag, a Strep tag, or a StrepII tag.

Each of the mutant RSV F molecules described above, and elsewhere herein, can be provided in either membrane bound or soluble (i.e. non-membrane bound) form. In some embodiments membrane bound forms include the transmembrane and cytoplasmic domains of naturally occurring RSV F proteins—details of which (including sequences) are provided in the Detailed Description section of this patent disclosure. In some embodiments membrane bound forms may include other transmembrane and cytoplasmic domains—i.e.

that are not native to RSV F proteins. In some embodiments, soluble (i.e. non-membrane bound) forms of the mutant RSV F molecules described herein are used. Soluble forms may be particularly useful where the RSV F molecule is to be used as a component of a pharmaceutical composition—e.g. for use as a vaccine for protection against RSV. Such soluble versions of the mutant RSV F molecules described herein can be produced by, for example, removing the transmembrane and cytoplasmic domains—as described further in the Detailed Description section of this patent disclosure. In some such embodiments heterologous sequences may be added to replace the transmembrane and cytoplasmic domains—such as, for example, heterologous trimerization domains, such as foldon domains—as described further in the Detailed Description section of this patent disclosure.

Each of the mutant RSV F molecules described above, and elsewhere herein, can be provided in the form of a mature RSV F trimer that comprises one-or-more-more DT cross links and is conformationally locked in its pre-F conformation. Such conformationally locked RSV F molecules are made by performing a DT crosslinking reaction—as described in the Detailed Description and Examples sections of the present application and/or as described in International Patent Application No. PCT/US2014/048086 (Publication No. WO/2015/013551)—the contents of which are hereby incorporated by reference.

In some embodiments the present invention provides a mutant RSV F molecule as described herein comprising at least one DT cross-link. In some embodiments the present invention provides a trimeric mutant RSV F molecule as described herein comprising at least three DT cross-links. In some embodiments the present invention provides a trimeric mutant RSV F molecule as described herein comprising at least six DT cross-links.

In some embodiments the present invention provides a mutant RSV F molecule as described herein comprising at least one DT cross-link wherein at least one tyrosine of the at least one DT cross-link was introduced by a point-mutation to tyrosine. In some embodiments the present invention provides a mutant trimeric RSV F molecule as described herein comprising at least three DT cross-links, wherein at least one tyrosine of each of the at least three DT cross-links was introduced by a point-mutation to tyrosine.

For example, in some embodiments a DT cross-link is introduced between a tyrosine at residue 198 (typically a naturally occurring tyrosine) and an introduced tyrosine at residue 226 (i.e. resulting from a 226Y mutation)—forming an intramolecular 198Y-226Y DT crosslink. This creates an RSV F trimer comprising three intramolecular DT cross-links. In some embodiments a DT cross-link is introduced between an introduced tyrosine at residue 185 (i.e. resulting from a185Y mutation) and an introduced tyrosine at residue 428 (i.e. resulting from a 428Y mutation)—forming a 185Y-428Y intermolecular DT crosslink. This creates an RSV F trimer comprising three intermolecular DT cross-links.

And in some embodiments both a 198Y-226Y intramolecular DT cross link and a 185Y-428Y intermolecular DT crosslink are introduced. This creates an RSV F trimer comprising six DT cross links—three intramolecular DT cross-links and three intermolecular DT cross-links.

In some embodiments the present invention provides compositions comprising one or more of the mutant RSV F molecules described above or elsewhere herein. In some such embodiments the composition is a pharmaceutical composition—i.e. its components are suitable for administration to a living subject. In some such embodiments the pharmaceutical composition comprises one or more adjuvants. Exemplary adjuvants include, but are not limited to, alum adjuvants. In some embodiments the pharmaceutical composition comprises a carrier. In some embodiments the pharmaceutical composition comprises an immunostimulatory agent. In some embodiments the composition is, or forms part of, an RSV vaccine, or can be used in a method of vaccination.

In some embodiments the present invention provides nucleic acid molecules that encode the various different mutant RSV F molecules described above and elsewhere herein. In some embodiments the present invention provides vectors that comprise such nucleic acid molecules. In some embodiments the present invention provides cells that comprise such nucleic acid molecules or vectors.

In some embodiments the present invention provides methods for treating or preventing RSV in a subject. In some embodiments the present invention provides methods of vaccinating a subject against RSV. In some embodiments the present invention provides methods of eliciting the production of RSV neutralizing antibodies in a subject. Each of such methods comprise administering to the subject an effective amount of a mutant RSV F molecule as described herein, or an effective amount of a pharmaceutical composition comprising such a mutant RSV F molecule. In some such embodiments the subject is a non-human mammal. For example, in some embodiments the subject may be a non-human mammal that is useful for conducting preclinical studies, such as a rodent (e.g. a mouse or a cotton rat) or a non-human primate. In some embodiments the subject may be a human. In embodiments where the subject is a human the human subject can be of any age. In some embodiments the human subject is an infant. In some embodiments the human subject is a child. In some embodiments the human subject is less than 24 months in age. In some embodiments, the human subject is an adult. In some embodiments, the human subject is greater than 50 years in age. In some embodiments, the human subject is greater than 60 years in age.

In some embodiments the present invention provides methods for producing anti-RSV F antibodies—using the mutant RSV F molecules described herein as immunogens. Such antibodies may be useful for a variety of applications, including for research applications and for therapeutic applications. For example, in some embodiments such methods comprise administering a mutant RSV F molecule as described herein to an animal subject that is useful for the production of antibodies, such as a mouse or a rabbit. In some embodiments the subject may be an animal that has been genetically altered to allow for the production of fully human antibodies. In other embodiments the mutant RSV F molecules described herein can be used as immunogens in other systems useful for antibody production, including, but not limited to, library screening methods, such as phage display screening methods.

These and other aspects of the present invention are described further in the Detailed Description, Examples, Claims, Figures/Drawings, and Brief Description of the Drawings sections of this patent application—all of which sections are intended to be read in conjunction with one another. Furthermore, one of skill in the art will recognize that the various embodiments of the present invention described above and elsewhere throughout this patent disclosure can be combined in various different ways, and that such combinations are within the scope of the present invention.

BRIEF DESCRIPTION OF THE DRAWINGS

FIG. 3A—After performing the DT cross-linking reaction, stability introduced by the intramolecular crosslink between 198Y and 226Y ("Design 1") was measured at 4° C. over 2 weeks by ELISA using D25, a prefusion-specific mAb that binds Site Ø. FIG. 3B—The intermolecular DT bond formation between 185Y and 428Y ("Design 2") was assayed by Western blotting, by comparison to WT (Motavizumab is primary Ab). The $F_1$ protein shifts to the size of a trimer (TM).

FIGS. 5A-B. Comparison of conformational integrity of DS-Cav1, an un-crosslinked version of a 428Y RSV F mutant (AVR02), and a DT crosslinked version of the 428Y mutant (DT-AVR02) by ELISA using motavizumab to normalize, and using an antibody that binds to antigenic site IV/V (FIG. 5A) and an antibody that binds to site Ø (FIG. 5B) to assess conformational integrity.

FIGS. 6A-C. Site Ø antigenicity after 100 hr 37° C. thermo-challenge. FIG. 6A. Comparison of retained binding of 5C4 (site Ø) to a 428Y RSV F mutant (AVR02) and a DT crosslinked version of the 428Y RSV F mutant (DT-AVR02) after incubation at 4° C. and 37° C. FIG. 6B. Retained 5C4 and D25 binding to DS-Cav1 and DT-AVR02 after 100 hr incubation at 37° C. The left bar in each pair is 5C4. The right bar in each pair is D25. FIG. 6C. Retained binding of 5C4 (site Ø) to a 428Y RSV F mutant (AVR02) after 5 weeks at 4° C.

FIGS. 13A-D. Tyrosine substitution at position 428 (428Y) instead of 427 (447Y) dramatically improves the antigenic profile of RSV F mutants. Streptactin purified, soluble 427Y (DT-Cav1) mutants (FIG. 13A-B) or 428Y (DT-AVR02) mutants (FIGS. 13. C-D) were subjected to DT cross-linking, purified, and analyzed for antigenicity using the indicated mAbs. ELISAs were normalized for total protein using Motavizumab and performed on Ni-NTA coated plates. DSCav1 was used as a positive control. The prefusion structure was probed with two conformational antibodies; a mAb specific for site Ø, and a prefusion specific mAb that binds between antigenic site IV/V.

FIGS. 14A-C. Size Exclusion Chromatography (SEC) and SDS-PAGE analysis reveal markedly different profiles of a DT cross linked 427Y RSV F mutant (DT-Cav1) and a DT cross linked 428Y RSV F mutant (DT-AVR02). The size exclusion chromatography profiles of the indicated RSV F mutants (427 Y/DT-Cav1 FIG. 14A top, left and 428Y/DT-AVR02 FIG. 14B bottom left) immediately following the dityrosine crosslinking reaction are shown. The 428Y mutation accomplishes a dramatic reduction in higher-order species following the crosslinking reaction. Final products after separation under reducing and denaturing conditions on SDS-PAGE gels, followed by Coomassie staining, are shown in FIG. 14C (right). Arrows indicate the higher order species (427Y/DT-Cav1) and the crosslinked trimeric species (428Y/DT-AVR02).

FIGS. 15A-B. Serum Neutralization titers from animals vaccinated with a DT cross linked 428Y RSV F mutant (DT-AVR02) are dramatically higher than those from animals vaccinated with a DT cross linked 427Y RSV F mutant (DT-Cav1). Animals were vaccinated in a prime: boost regimen with 10 μg (micrograms) of either a DS-Cav1 control (benchmark comparator) or the indicated DT cross linked molecules (427Y/DT-Cav1 in FIG. 15A (left) and 428Y/DT-AVR02 in FIG. 15B (right)). Serum was harvested post boost, heat-inactivated, and neutralization titers were obtained using an RSV-Renilla Luciferase reporter virus. Neutralization titers as indicated are the average of 5 animals/group and calculated as the reciprocal serum dilution resulting in 50% inhibition of luciferase activity.

FIGS. 16A-B. Formulation with Sucrose Reduces Formation of RSV F Aggregates. Experiments were performed using a DT-cross-linked 428Y mutant (DT-AVR02). After final concentration, analytical size-exclusion chromatography (SEC) was performed. As shown in FIG. 16A three peaks were identified—of which peak C is trimers, and peaks A and B are aggregates. Formulation of the DT-AVR02 molecule with 10% sucrose during elution of the purification step appeared to eliminate the formation of aggregates. As shown in FIG. 16B, peak C (trimers) remained but peaks A and B (aggregates) were not apparent in the samples formulated with 10% sucrose.

DETAILED DESCRIPTION OF THE INVENTION

Figure 1:
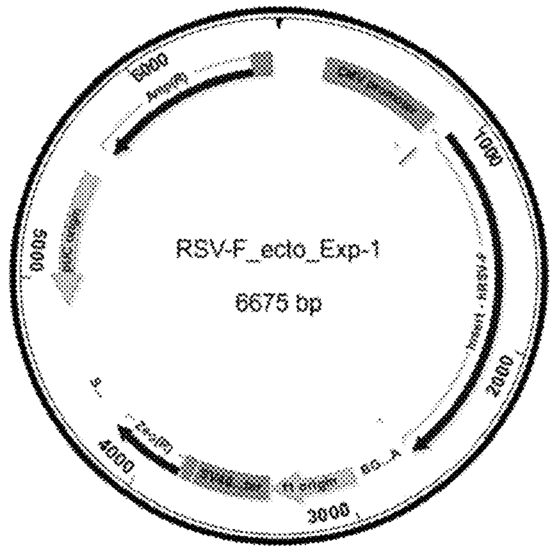
FIG. 1. Exemplary nucleic acid vector for expression of the RSV F molecules described herein in mammalian cells.

The present invention provides, in part, mutant RSV F molecules that comprise one-or-more to-tyrosine mutations and that can be, or are, stabilized in a pre-fusion conformation by the introduction of one-or-more DT cross-links. The present invention also provides nucleic acid molecules that encode such mutant RSV F molecules, methods of making such mutant RSV F molecules, compositions comprising such mutant RSV F molecules, and methods of use of such mutant RSV F molecules—including, but not limited to, vaccination methods, therapeutic methods, and antibody production methods.

Definitions

The technical and scientific terms used in the present disclosure have the meanings commonly understood by those of ordinary skill in the art and/or their meaning is clear from the context in which the terms are used—unless specifically defined otherwise herein. Several terms are defined below. Other terms are defined elsewhere in the text of this patent disclosure.

As used in this specification and the appended claims, the singular forms "a," "an," and "the" include plural referents, unless the context clearly dictates otherwise. The terms "a" (or "an") as well as the terms "one or more" and "at least one" can be used interchangeably. Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Système International de Unites (SI) accepted form. Numeric ranges provided herein are inclusive of the numbers defining the range.

As used in the present specification the terms "about" and "approximately," when used in relation to numerical values, mean within + or −20% of the stated value.

As used herein the term "exemplary" means serving as an example, instance, or illustration.

As used herein the term "RSV F molecules" refers to all forms of the RSV F protein that comprise an F1 polypeptide and an F2 polypeptide—i.e. including F0 precursor polypeptides, trimers of F0 precursor polypeptides, RSV F protomers, and mature RSV F trimers—whether membrane bound or soluble. As used herein the term "mutant RSV F molecules" refers to RSV F molecules that contain one or more artificially introduced/man-made mutations. An As used herein the term "F1 polypeptide" refers to a polypeptide comprising amino acid residues 137-513 of an RSV F F0 precursor sequence. Amino acid residues 137-513 do not include the RSV F transmembrane and cytoplasmic domains. In some embodiments F1 polypeptides may also include the RSV F transmembrane and cytoplasmic domains (located within residues 514-574 of the RSV F F0 precursor sequence).

As used herein the term "F2 polypeptide" refers to a polypeptide comprising amino acid residues 26-109 of an RSV F F0 precursor sequence.

As used herein the terms "protein" and "polypeptide" are used interchangeably, unless otherwise stated. As used herein the term "protein complex" refers to an assembly of two or more proteins or protein subunits, such as two or more monomers or protomers. Unless otherwise stated, all description herein that relates to proteins or polypeptides applies equally to protein complexes, and vice versa.

As used herein, the terms "nucleic acid molecules," nucleic acid sequences," and "nucleotide sequences" are used interchangeably.

As used herein the terms "stabilized" and "locked" are used interchangeably, for example in relation to the effect of cross-linking in stabilizing or locking the RSV F protein in its pre-fusion conformation. These terms do not require 100% stability. Rather these terms denote a degree of improved or increased stability. For example, in some embodiments, when the term "stabilized" is used in relation to a RSV F protein cross-linked in its pre-fusion conformation, the term denotes that the pre-fusion conformation has greater stability than it would have had prior to or without such cross-linking. Stability, and relative stability, may be measured in various ways as described in other sections of this application, for example based on the half-life of the RSV pre-fusion conformation. The improvement or increase in stability may be to any degree that is useful or significant for the intended application. For example, in some embodiments stability may be increased by about 10%, 25%, 50%, 100%, 200% (i.e. 2-fold), 300% (i.e. 3-fold), 400% (i.e. 4-fold), 500% (i.e. 5-fold), 1000% (i.e. 10-fold), or more.

As used herein the term "adjuvant" refers to a substance capable of enhancing, accelerating, or prolonging the body's immune response to an immunogen or immunogenic composition, such as a vaccine As used herein the term "DS-Cav1" refers to the mutant RSV F protein described in McLellan, et al., Science, 342 (6158), 592-598, 2013—which comprises S155C, S290C, S190F, and V207L mutations.

As used herein the term "pre-fusion conformation" refers to a structural conformation of an RSV F molecule that can be specifically bound by a pre-fusion-specific antibody.

As used herein the term "pre-fusion-specific antibody" refers to an antibody that specifically binds to an RSV F molecule in its pre-fusion conformation, but does not bind to the RSV F protein in a post-fusion conformation. Prefusion-specific antibodies include, but are not limited to the D25, AM22, 5C4, and AM14 antibodies.

As used herein the term "AM14" refers to an antibody described in WO 2008/147196 A2.

As used herein the term "AM22" refers to an antibody described in WO 2011/043643 A1.

As used herein the term "D25" refers to an antibody described in WO 2008/147196 A2.

As used herein the term "5C4" refers to an antibody as described in Mclellan et al., 2010, Nat. Struct. Mol. Biol., February 17 (2): 248-50) were mapped. McLellan et al. (Science 340:1113-1117 (2013)).

Mutant RSV F Molecules

The RSV Fusion or "F" protein is an envelope glycoprotein of respiratory syncytial viruses. In nature the RSV F protein is translated as a single precursor polypeptide (designated F0). The F0 precursor polypeptide is generally 574 amino acids in length. Amino acids 1-25 of the F0 precursor generally comprise a signal peptide. The precursor polypeptide F0 forms a precursor trimer, which is typically proteolytically cleaved by one or more cellular proteases at conserved furin consensus cleavage sites to yield a Pep 27 polypeptide, an F1 polypeptide and an F2 polypeptide. The Pep 27 polypeptide (generally amino acids 110-136 of the F0 precursor) is excised and does not form part of the mature RSV F trimer. The F2 polypeptide (which may alternatively be referred to herein as "F2" or the "F2 region") generally consists of amino acid residues 26-109 of the F0 precursor. The F1 polypeptide (which may alternatively be referred to herein as "F1" or the "F1 region") generally consists of amino acid residues 137-574 of the F0 precursor, and comprises an extracellular region (generally residues 137-524), a transmembrane domain (generally residues 525-550), and a cytoplasmic domain (generally residues 551-574). The F1 and F2 polypeptides are linked by disulfide-bonds to form a heterodimer which is referred to as an RSV F "protomer." Three such protomers form the mature RSV F trimer—which is thus a homotrimer of the three protomers. In nature the mature RSV F trimer is generally membrane-bound. However, soluble (i.e. non-membrane bound) versions of the mature RSV F trimer can be made by removing the transmembrane and cytoplasmic regions. For example, conversion to a soluble form can be accomplished by truncating the RSV F protein at amino acid 513 (i.e. by removing amino acids 514 onwards).

In nature the mature RSV F trimer mediates fusion of viral and cellular membranes. The pre-fusion conformation of the mature RSV F trimer (which may be referred to herein as "pre-F") is highly unstable (metastable). However, once the RSV virus docks with the cell membrane, the RSV F protein trimer undergoes a series of conformational changes and transitions to a highly stable post-fusion ("post-F") conformation. The mature RSV F protein is known to induce potent neutralizing antibodies ("nAbs") that correlate with RSV protection. For example, immunization with the RSV F protein induces nAbs that are protective in humans (e.g. Synagis). Several neutralizing epitopes (sites I, II and IV) are present on the post-fusion form of RSV F protein. Recently, however, Magro et al. showed that incubation of human sera with the RSV F protein in its post-fusion conformation failed to deplete the majority of neutralizing activity against the F protein, indicating the presence of neutralizing antigenic sites unique to the pre-fusion conformation (Magro et al. 2012, PNAS 109 (8): 3089). By x-ray crystallography, the epitopes recognized by palivizumab (Synagis), motavizumab (Numax), and that of the more recently discovered 101F monoclonal antibody (McLellan et al., 2010, J. Virol., 84 (23): 12236-441; and Mclellan et al., 2010, Nat. Struct. Mol. Biol., February 17 (2): 248-50) were mapped. McLellan et al. (Science 340:1113-1117 (2013)) solved the structure of the F protein in its pre-fusion conformation, which revealed a novel neutralizing epitope—site ø—that is only displayed in the pre-fusion conformation, and to which a series of antibodies bind, e.g. 5C4, that are up to 50-fold more potently neutralizing than Synagis and Numax. Accordingly, there is mounting evidence that an RSV vaccine immunogen in this pre-fusion conformation and displaying site ø could elicit effective protection. However, the highly unstable (metastable) nature of the pre-fusion conformation of the RSV F protein has proved to be a significant barrier to the development of such a vaccine. Based on a comparison of the pre- and post-fusion RSV F structures of Mclellan et al. there appear to be two regions of the F protein that undergo large conformational changes (>5 Å). These regions are located at the N- and C-termini of the F1 subunit (residues 137-216 and 461-513, respectively). In the crystal structure of the RSV F protein held in its pre-fusion conformation by the D25-antibody bound to the site ø epitope, the C-terminal F1 residues can be stabilized in the pre-fusion conformation by appending a foldon trimerization domain. To stabilize the N-terminal region of F1, Mclellan et al. found that binding of the antibody D25 was sufficient for crystallographic studies. However, for production of a vaccine immunogen alternative stabilization strategies are needed, such as those that do not require the RSV F protein to be bound to a large antibody molecule. One alternative approach that has been attempted involved the introduction of paired cysteine mutations (for disulfide bond formation) and cavity-filling mutations near the F1 N-terminus (see the DS-Cav1 RSV F protein variant described in Mclellan et al. (2013) Science 342:592-598, which is hereby incorporated by reference in its entirety). However, crystallographic analysis of such variants revealed that the structure was only partially in the pre-fusion conformation. Accordingly, additional engineering of the RSV F protein is needed in order to achieve an immunogen for clinical vaccine development.

The present invention provides certain alternative approaches for stabilizing the RSV F protein in its pre-fusion conformation—based on the introduction of one or more "to-tyrosine" mutations and one or one or more DT cross links at specified locations in RSV F molecules.

The amino acid sequences of several exemplary RSV F and mutant RSV F molecules are provided in Table 1 and in the Sequence Listing section of this patent disclosure. Most of the sequences provided in Table 1 are presented as "F0" sequences—i.e. these sequences comprise a signal peptide and a pep27 peptide that is present in F0 precursors but that is not present in mature RSV F proteins. Similarly, several of the sequences provided in Table 1 include native transmembrane and cytoplasmic domains that, in some embodiments, can be removed to form soluble versions of mature RSV trimers. Thus, the final/mature versions of these exemplary mutant RSV molecules (i.e. the versions that may be DT cross linked) typically will not comprise all of the amino acids shown in the sequences in Table 1. However, the final/mature versions of these exemplary mutant RSV molecules will comprise the F2 region and at least a portion of the F1 region of these sequences. Typically, the final/mature versions of these exemplary mutant RSV molecules will comprise amino acid residues 26-109 and amino acid residues 137-513 of these sequences. It should be noted that, in all embodiments herein that refer to an RSV F molecule having a specific exemplary amino acid sequence, either the full F0 sequence or amino acid residues 26-109 and amino acid residues 137-513 therefore are contemplated.

Throughout the present patent disclosure, when specific amino acid positions/residues in an RSV F molecule are referred to by their amino residue number (such as amino acid residue 428 for example), and unless otherwise stated, the amino acid numbering is that used for the RSV F amino acid sequences provided in the Sequence Listing and in Table 1 of the present application (see, e.g., SEQ ID NOs. 1-91). This is the same numbering system that is used routinely in the art when describing RSV F sequences. However, it should be noted, and one of skill in the art will understand, that different numbering systems can be used. For example, if there are additional amino acid residues added or removed as compared to any of SEQ ID NO: 1-91. As such, it is to be understood that when a specific amino acid residue is referred to by its number, the description is not limited to only amino acids located at precisely that numbered position when counting from the beginning of a given amino acid sequence, but rather that the "corresponding" amino acid residue in any and all RSV F sequences is intended—even if that residue is not at the same precise numbered position in a given molecule, for example if the RSV sequence is shorter or longer than SEQ ID NO. 1, or has insertions or deletions as compared to SEQ ID NO. 1. One of skill in the art can readily determine what is the "corresponding" amino acid position to any of the specific numbered residues recited herein, for example by aligning a given RSV F sequence to SEQ ID NO. 1 or to any of the other RSV F amino acid sequences provided herein (i.e.

SEQ ID NOs. 1-91). Such alignments can be readily performed—whether by computer or by eye—given the highly conserved nature of RSV F sequences across RSV subtypes and RSV strains. The amino acid sequences of a large number of WT/native RSV F molecules from different RSV subtypes and strains, as well as nucleic acid sequences encoding such RSV F molecules, are known in the art. Amino acid sequences of several exemplary WT/native RSV F molecules are provided in SEQ ID NOs: 1-20 and 82-85. Other such sequences can be found in public sequence databases. Other such sequences are described in International Patent Application No. PCT/US2014/048086 U.S. Pat. No. 9,738,689, 9,950,058—the contents of each of which are hereby incorporated by reference.

WT/native RSV F molecules exhibit a strikingly high level of sequence conservation—both across RSV subtypes and across RSV strains. See, for example, WO2014/160463. For example, RSV subtypes A and B share 90% sequence identity across the F0 precursor molecule. Within a given RSV subtype (e.g. subtype A or B) the sequence identity across strains is about 98%. Furthermore, nearly all RSV F F0 precursors identified to date consist of 574 amino acids. There can be some minor differences in length—such differences generally occurring in the cytoplasmic domain.

The specific to-tyrosine mutations described herein can be introduced into any suitable RSV F "background" sequence.

In some embodiments such "background" sequences are those of WT/native RSV F molecules (i.e. those that exist in nature). The amino acid and nucleotide sequences of a large number of WT/native RSV F molecules from different RSV subtypes and strains are known in the art. Amino acid sequences of several exemplary WT/native RSV F molecules are provided in SEQ ID NOs: 1-20 and 82-85 (see Table 1 and Sequence Listing). Other such sequences are described in International Patent Application No. PCT/US2014/048086 U.S. Pat. No. 9,738,689, 9,950,058—the contents of each of which are hereby incorporated by reference.

In some embodiments such "background" sequences are those of mutant RSV F molecules—i.e. those that comprise one or more artificially introduced mutations as compared to WT/native RSV F molecules. For example, in some embodiments the "background" RSV F sequence may comprise a "Cav1" mutation, a "DS" mutation, or a combination thereof.

Non-limiting examples of suitable mutant background RSV molecules into which the specific mutations described herein may be introduced include those having the amino acid sequences of any of SEQ ID Nos 86-91, or those comprising amino acids 26-109 (i.e. F2) and amino acids 137-513 (i.e. F1) of any of SEQ ID Nos 86-91 (see Table 1 and Sequence Listing). Other suitable mutant background RSV molecules into which the specific mutations described herein may be introduced include those described in International Patent Application No. PCT/US2014/048086 U.S. Pat. No. 9,738,689, 9,950,058.

In some embodiments the "background" RSV F molecule—into which the specific mutations described herein may be introduced—may be a "full-length" RSV F molecule, i.e.

comprising a transmembrane domain and a cytoplasmic domain. Non-limiting examples of suitable "full length" background RSV molecules into which the specific mutations and cross-links described herein may be introduced include those having the amino acid sequences of any of SEQ ID Nos 1-9, 11-29, 31-49, 51-80, 83, 85, 87, or 89, or those comprising amino acids 26-109 (F2) and amino acids 137-513 (F1) of any of SEQ ID Nos 1-9, 11-29, 31-49, 51-80, 83, 85, 87, or 89 (see Table 1 and Sequence Listing).

In some embodiments the "background" RSV F molecule—into which the specific mutations and cross-links described herein may be introduced—may be a "soluble" RSV F molecule, i.e not. comprising a transmembrane domain and a cytoplasmic domain. Non-limiting examples of suitable "soluble" background RSV molecules into which the specific mutations and cross-links described herein may be introduced include those having the amino acid sequences of any of SEQ ID Nos 10, 30, 50, 81, 82, 84, 86, 88, or 90 or those comprising amino acids 26-109 (i.e. F2) and amino acids 137-513 (i.e. F1) of any of SEQ ID Nos 10, 30, 50, 81, 82, 84, 86, 88, or 90.

Similarly, in some embodiments the soluble "background" RSV F molecule—into which the specific mutations and cross-links described herein may be introduced—may be created by removing the transmembrane domain and cytoplasmic domain of a "full-length" RSV F molecule, for example by removing amino acids 514 onwards of a "full-length" RSV F molecule—such as one of those described above.

In some embodiments the present invention provides mutant RSV F molecules comprising a point mutation to tyrosine at amino acid residue 428 (which may be referred to as a 428Y point mutation), or at an amino acid that corresponds to position 428—for example as determined by alignment to, and/or using the amino acid numbering of, SEQ ID NO.1.

In some embodiments such mutant RSV F molecules comprising a 428Y mutation further comprise a point mutation to tyrosine at amino acid residue 185 (which may be referred to as a 185Y point mutation), or at an amino acid that corresponds to position 185—for example as determined by alignment to, and/or using the amino acid numbering of, SEQ ID NO.1. Such mutants thus comprise both a 428Y mutation and a 185Y mutation.

In some embodiments such mutant RSV F molecules comprising a 428Y mutation further comprise a point mutation to tyrosine at amino acid residue 226 (which may be referred to as a 226Y point mutation), or at an amino acid that corresponds to position 226—for example as determined by alignment to, and/or using the amino acid numbering of, SEQ ID NO.1. Such mutants thus comprise both a 428Y mutation and a 226Y mutation.

In some embodiments such mutant RSV F molecules comprising a 428Y mutation further comprise both (a) a point mutation to tyrosine at amino acid residue 226 (which may be referred to as a 226Y point mutation), or at an amino acid that corresponds to position 226—for example as determined by alignment to, and/or using the amino acid numbering of, SEQ ID NO.1, and (b) a point mutation to tyrosine at amino acid residue 185 (which may be referred to as a 185Y point mutation), or at an amino acid that corresponds to position 185—for example as determined by alignment to, and/or using the amino acid numbering of, SEQ ID NO.1. Such mutants thus comprise a 428Y mutation, a 185Y mutation, and a 226Y mutation.

In some embodiments the mutant RSV F molecule comprises a transmembrane domain and a cytoplasmic domain. In some embodiments the mutant RSV F molecule does not comprise a transmembrane domain and/or a cytoplasmic domain—i.e. it is a soluble (non-membrane bound) RSV F molecule.

In some embodiments the mutant RSV F molecule is RSV type A or RSV type B molecule.

In some embodiments the mutant RSV F molecule is capable of binding to a pre-fusion specific antibody. In some embodiments the mutant RSV F molecule is capable of binding to an antibody that recognizes antigenic site ø—such as one of those described in U.S. Pat. Nos. 9,738, 689, 9,950,058, or Mclellan et al. (2013) Science 342:592-598, each of which is hereby incorporated by reference in its entirety for this purpose. Non-limiting examples of such antibodies include D25, 5C4 and AM22. Other antibodies that recognizes antigenic site ø are disclosed herein or are known in the art.

In some embodiments the mutant RSV F molecule comprises an F2 polypeptide and an F1 polypeptide wherein the C-terminal of the F2 polypeptide is linked to the N-terminal of the F1 polypeptide by a disulfide bond. In some embodiments the mutant RSV F molecule comprises an F2 polypeptide and an F1 polypeptide wherein the C-terminal of the F2 polypeptide is linked to the N-terminal of the F1 polypeptide by an artificially introduced peptide linker.

In some embodiments the mutant RSV F molecule comprises: (a) an F2 polypeptide comprising or consisting of approximately 84 amino acid residues and (b) an F1 polypeptide comprising or consisting of amino acid residues approximately 375 amino acid residues.

In some embodiments the mutant RSV F molecule comprises: (a) an F2 polypeptide comprising or consisting of approximately 74-84 acid residues and (b) an F1 polypeptide comprising or consisting of amino acid residues approximately 365-375 amino acid residues.

In some embodiments the mutant RSV F molecule comprises: (a) an F2 polypeptide comprising or consisting of amino acid residues 26-109 of any of SEQ ID NOs 21-81, and (b) an F1 polypeptide comprising or consisting of amino acid residues 137-513 of any of SEQ ID NOs 21-81.

In some embodiments the mutant RSV F molecule comprises: (a) an F2 polypeptide comprising or consisting of approximately 74-84 amino acids of amino residues 26-109 of any of SEQ ID NOs 21-81, and (b) an F1 polypeptide comprising or consisting of approximately 365-375 amino acids of amino acid residues 137-513 of any of SEQ ID NOs 21-81.

In some embodiments the mutant RSV F molecule comprises (a) an F2 polypeptide comprising or consisting of amino acid residues 26-109 of SEQ ID NO 81, and (b) an F1 polypeptide comprising or consisting of amino acid residues 137-513 of SEQ ID NO. 81.

In some embodiments the mutant RSV F molecule comprises (a) an F2 polypeptide comprising or consisting of approximately 74-84 amino acids of amino acid residues 26-109 of SEQ ID NO 81, and (b) an F1 polypeptide comprising or consisting of approximately 365-375 amino acids of amino acid residues 137-513 of SEQ ID NO. 81.

In some embodiments the mutant RSV F molecule is stabilized in a prefusion conformation by one or more di-tyrosine cross-links.

In some embodiments the mutant RSV F molecule is a mature RSV F trimer. In some such embodiments the RSV F molecule is a mature RSV F trimer stabilized in a prefusion conformation by three or more di-tyrosine cross-links.

In some embodiments the mutant RSV F molecule comprises a di-tyrosine cross-link between a tyrosine at amino acid position 428 (or an amino acid position corresponding thereto—for example as determined by alignment to, and/or using the amino acid numbering of, SEQ ID NO.1) and a tyrosine at amino acid position 185 (or an amino acid position corresponding thereto—for example as determined by alignment to, and/or using the amino acid numbering of, SEQ ID NO.1).

In some embodiments the mutant RSV F molecule comprises a di-tyrosine cross-link between a tyrosine at amino acid position 198 (or an amino acid position corresponding thereto—for example as determined by alignment to, and/or using the amino acid numbering of, SEQ ID NO.1) and a tyrosine at amino acid position 226 (or an amino acid position corresponding thereto—for example as determined by alignment to, and/or using the amino acid numbering of, SEQ ID NO.1).

In some embodiments the mutant RSV F molecule comprises both: (a) a di-tyrosine cross-link between a tyrosine at amino acid position 198 (or an amino acid position corresponding thereto—for example as determined by alignment to, and/or using the amino acid numbering of, SEQ ID NO.1) and a tyrosine at amino acid position 226 (or an amino acid position corresponding thereto—for example as determined by alignment to, and/or using the amino acid numbering of, SEQ ID NO.1), and (b) a di-tyrosine cross-link between a tyrosine at amino acid position 428 (or an amino acid position corresponding thereto—for example as determined by alignment to, and/or using the amino acid numbering of, SEQ ID NO.1) and a tyrosine at amino acid position 185 (or an amino acid position corresponding thereto—for example as determined by alignment to, and/or using the amino acid numbering of, SEQ ID NO.1).

In some embodiments the mutant RSV F molecule is a mature RSV F trimer comprising three di-tyrosine cross-links—each of which is between a tyrosine at an amino acid position 428 (or an amino acid position corresponding thereto—for example as determined by alignment to, and/or using the amino acid numbering of, SEQ ID NO.1) and a tyrosine at an amino acid position 185 (or an amino acid position corresponding thereto—for example as determined by alignment to, and/or using the amino acid numbering of, SEQ ID NO.1).

In some embodiments the mutant RSV F molecule is a mature RSV F trimer comprising three di-tyrosine cross-links—each of which is between a tyrosine at an amino acid position 198 (or an amino acid position corresponding thereto—for example as determined by alignment to, and/or using the amino acid numbering of, SEQ ID NO.1) and a tyrosine at an amino acid position 226 (or an amino acid position corresponding thereto—for example as determined by alignment to, and/or using the amino acid numbering of, SEQ ID NO.1).

In some embodiments the mutant RSV F molecule is a mature RSV F trimer comprising six di-tyrosine cross-links, of which three are between a tyrosine at an amino acid position 198 (or an amino acid position corresponding thereto—for example as determined by alignment to, and/or using the amino acid numbering of, SEQ ID NO.1) and a tyrosine at an amino acid position 226 (or an amino acid position corresponding thereto—for example as determined by alignment to, and/or using the amino acid numbering of, SEQ ID NO.1), and three are between a tyrosine at an amino acid position 428 (or an amino acid position corresponding thereto—for example as determined by alignment to, and/or using the amino acid numbering of, SEQ ID NO.1) and a tyrosine at an amino acid position 185 (or an amino acid position corresponding thereto—for example as determined by alignment to, and/or using the amino acid numbering of, SEQ ID NO.1).

In some embodiments, the mutant RSV F molecules further comprise one or more artificially introduced non-DT cross-links. In some such embodiments such non-DT cross-links are di-sulfide bonds. In some such embodiments such RSV F molecules comprises one-or-more point mutations to cysteine. In some such embodiments one or more of the disulfide bonds is formed between two cysteines—one or both of which has been introduced by point mutation. In some such embodiments the RSV F molecule comprises a point mutation to cysteine at amino acid residue 155 (i.e. a 155C mutation). In some such embodiments the RSV F molecule comprises a point mutation to cysteine at amino acid residue 290 (i.e. a 290C mutation). In some such embodiments the RSV F molecule comprises both a point mutation to cysteine at amino acid residue 155 (i.e. a 155C mutation) and a point mutation to cysteine at amino acid residue 290 (i.e. a 290C mutation). In some such embodiments the RSV F molecule comprises one or more of the point mutations to cysteine disclosed in either U.S. Patent No. 9,738, 689, U.S. Pat. No. 9,950,058, or Mclellan et al. (2013) Science 342:592-598, each of which is hereby incorporated by reference in its entirety for this purpose.

In some embodiments, the mutant RSV F molecules further comprise one or more artificially introduced cavity-filling mutations (e.g. substitutions). In some such embodiments the RSV F molecule comprises a mutation to F at amino acid residue 190 (a 190F mutation). In some such embodiments the RSV F molecule comprises a point mutation to L at amino acid residue 207 (a 207L mutation). In some such embodiments the RSV F molecule comprises both a mutation to F at amino acid residue 190 (a 190F mutation) and a point mutation to L at amino acid residue 207 (a 207L mutation). In some such embodiments the RSV F molecule comprises one or more cavity-filling amino acid substitutions selected from the group consisting of: 58W, 83W, 87F, 90L, 153W, 190F, 203W, 207L, 220L, 260W, 296F, and 298L. In some such embodiments the RSV F molecule comprises one or more of the cavity-filling amino acid substitutions disclosed in either U.S. Patent No. 9,738, 689, U.S. Pat. No. 9,950,058, or Mclellan et al. (2013) Science 342:592-598, each of which is hereby incorporated by reference in its entirety for this purpose.

In some embodiments the mutant RSV F molecules comprise an oligomerization domain, such as a trimerization domain. In one embodiment the trimerization domain is a T4 foldon domain, a GCN4 domain, or a T4 fibrinitin domain. Examples of other trimerization domains that can be used include, but are not limited to, those described in Habazettl et al., 2009 (Habazettl et al., 2009. NMR Structure of a Monomeric Intermediate on the Evolutionarily Optimized Assembly Pathway of a Small Trimerization Domain. J. Mol. Biol. pp. null); Kammerer et al., 2005 (Kammerer et al., 2005. A conserved trimerization motif controls the topology of short coiled coils. Proc Natl Acad Sci USA 102 (39): 13891-13896); Innamorati et al., 2006. (Innamorati et al., 2006. An intracellular role for the C1q-globular domain. Cell signal 18 (6): 761-770); Schelling et al., 2007 (Schelling et al., 2007. The reovirus o-1 aspartic acid sandwich: A trimerization motif poised for conformational change. Biol Chem 282 (15): 11582-11589); Pancera et al., 2005. (Soluble Mimetics of Human Immunodeficiency Virus Type 1 Viral Spikes Produced by Replacement of the Native Trimerization Domain with a Heterologous Trimerization Motif: Characterization and Ligand Binding Analysis. J Virol 79 (15): 9954-9969); Guthe et al., 2004. (Very fast folding and association of a trimerization domain from bacteriophage T4 fibritin. J. Mol. Biol. v337 pp. 905-15); and Papanikolopoulou et al., 2008 (Creation of hybrid nanorods from sequences of natural trimeric fibrous proteins using the fibritin trimerization motif. Methods Mol Biol 474:15-33).

In some embodiments, the mutant RSV F molecules comprise the foldon domain of SEQ ID NO. 93.

In some embodiments, the mutant RSV F molecules further comprise one or more tags useful for detection and/or purification of the RSV F molecules (e.g. C-terminal tags). Exemplary tags include, but are not limited to, Strep tags, Strep II tags, FLAG tags, glutathione S-transferase (GST) tags, green fluorescent protein (GFP) tags, hemagglutinin A (HA) tags, histidine (His) tags, luciferase tags, maltose-binding protein (MBP) tags, c-Myc tags, protein A tags, protein G tags, and the like. In some such embodiments such RSV F molecules comprise the His tag of SEQ ID NO. 95. In some such embodiments such RSV F molecules comprise the Strep II tag of SEQ ID NO. 96. In some such embodiments such tags are cleavable tag—i.e. they can be cleaved/removed from the mutant RSV F molecule if desired. In some such embodiments such tags are located adjacent to (e.g. C-terminal to) a proteolytic cleavage site—such that a protease can be used to remove the tag. In some such embodiments such RSV F molecules comprise the thrombin cleavage site of SEQ ID NO. 94.

In some embodiments, the mutant RSV F molecules further comprise one or more peptide "linker" sequences. Suitable linker sequences include, but are not limited to, G, GG, GGG, GS, and SAIG (amino acids 1-4 of SEQ ID NO. 92) linker sequences. Such linkers may be provided; between the C-terminal end of F2 and the N-terminal end of F1, between the C-terminal end of F1 and the N-terminal end of any artificial trimerization domains, and/or between any other artificially introduced sequences—such as trimerization domains, proteolytic cleavage domains, and tags useful for detection and/or purification.

In some embodiments the mutant RSV F molecules comprise one or more leader sequences, precursor polypeptide sequences, secretion signals, and/or localization signals.

In those embodiments of the present invention that relate to specific exemplary amino acid sequences of mutant RSV F molecules (e.g. those of SEQ ID Nos 21-81) or of "background" RSV F molecules (e.g. those of SEQ ID Nos 1-20 or 82-91), or that related to specific regions of such sequences (e.g. F1 and/or F2 regions thereof) variant forms of such amino acid sequences that are equivalent thereto can also be used. For example, in some embodiments amino acid sequences that have at least 90%, 95%, 96%, 97%, 98%, or 99% sequence identity any of the RSV F amino acid sequences described herein across their F1 and F2 regions (specifically across amino acid residues 26-109 (F2) and 137-513 (part of F1 excluding the transmembrane and cytoplasmic domains) can be used. In some embodiments amino acid sequences that have at least about 80% or at least 85% sequence identity to such amino acid sequences across these F1 and F2 regions can be used. Such variant forms may have amino acids added, removed, or substituted as compared to one or more of the specific amino acid sequences provided herein. Thus they can be longer or shorter in length than the specified sequences.

Similarly, amino acid residues 514 onwards of each of the exemplary RSV F amino acid sequences provided herein may be removed or varied. For example, in several of the amino acid sequences provided herein amino acid residues 514 onwards comprise native RSV F transmembrane and cytoplasmic domains. In some embodiments these native RSV F transmembrane and cytoplasmic domains can be removed to generate a soluble (i.e. non-membrane bound)

version of the RSV F molecule, or can be replaced with different transmembrane and/or cytoplasmic domains. Similarly, in several of the amino acid sequences provided herein amino acid residues 514 onwards comprise a combination of various artificially added C-terminal sequences—such as the artificial C-terminal sequence provided in SEQ ID NO. 92, which comprises a foldon domain (SEQ ID NO. 93), a thrombin cleavage site (SEQ ID NO. 94), a Histidine tag (SEQ ID NO. 95), a Strep II tag (SEQ ID NO. 96), and various linkers. In some embodiments such artificial C-terminal sequences can be removed, modified, rearranged or replaced—as needed. For example, in some embodiments different trimerization domains may be used, and/or different cleavage sites may be used, and/or different epitope tags may be used.

In some embodiments one or more amino acid residues within one or the specific mutant RSV F molecules described herein can be substituted with another amino acid. In some embodiments, one or more amino acid residues can be substituted by another amino acid having a similar polarity and that may act as a functional equivalent, resulting in a silent alteration. In some embodiments substitutions for an amino acid within the sequence may be selected from other members of the class to which the amino acid belongs e.g. to create a conservative substitution. For examnple, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In some embodiments artificial, synthetic, or non-classical amino acids or chemical amino acid analogs can be used to make the mutant RSV F molecules described herein. Non-classical amino acids include, but are not limited to, the D-isomers of the common amino acids, fluoro-amino acids, and “designer” amino acids such as β-methyl amino acids, Cγ-methyl amino acids, Nγ-methyl amino acids, and amino acid analogs in general. Additional non-limiting examples of non-classical amino acids include, but are not limited to: α-aminocaprylic acid, Acpa; (S)-2-aminoethyl-L-cysteine/HCl, Aecys; aminophenylacetate, Afa; 6-amino hexanoic acid, Ahx; γ-amino isobutyric acid and α-aminoisobytyric acid, Aiba; alloisoleucine, Aile; L-allylglycine, Alg; 2-amino butyric acid, 4-aminobutyric acid, and α-aminobutyric acid, Aba; p-aminophenylalanine, Aphe; b-alanine, Bal; p-bromophenylalaine, Brphe; cyclohexylalanine, Cha; citrulline, Cit; β-chloroalanine, Clala; cycloleucine, Cle; p-cholorphenylalanine, Clphe; cysteic acid, Cya; 2,4-diaminobutyric acid, Dab; 3-amino propionic acid and 2,3-diaminopropionic acid, Dap; 3,4-dehydroproline, Dhp; 3,4-dihydroxylphenylalanine, Dhphe; p-flurophenylalanine, Fphe; D-glucoseaminic acid, Gaa; homoarginine, Hag; δ-hydroxylysine/HCl, Hlys; DL-β-hydroxynorvaline, Hnvl; homoglutamine, Hog; homophenylalanine, Hoph; homoserine, Hos; hydroxyproline, Hpr; p-iodophenylalanine, Iphe; isoserine, Ise; α-methylleucine, Mle; DL-methionine-S-methylsulfoniumchloide, Msmet; 3-(1-naphthyl) alanine, 1Nala; 3-(2-naphthyl) alanine, 2Nala; norleucine, Nle; N-methylalanine, Nmala; Norvaline, Nva; O-benzylserine, Obser; O-benzyltyrosine, Obtyr; O-ethyltyrosine, Oetyr; O-methylserine, Omser; O-methylthreonine, Omthr; O-methyltyrosine, Omtyr; Ornithine, Orn; phenylglycine; penicillamine, Pen; pyroglutamic acid, Pga; pipecolic acid, Pip; sarcosine, Sar; t-butylglycine; t-butylalanine; 3,3,3-trifluroalanine, Tfa; 6-hydroxydopa, Thphe; L-vinylglycine, Vig; (−)-(2R)-2-amino-3-(2-aminoethylsulfonyl) propanoic acid dihydroxochloride, Aaspa; (2S)-2-amino-9-hydroxy-4,7-dioxanonanoic acid, Ahdna; (2S)-2-amino-6-hydroxy-4-oxahexanoic acid, Ahoha; (−)-(2R)-2-amino-3-(2-hydroxyethylsulfonyl) propanoic acid, Ahsopa; (−)-(2R)-2-amino-3-(2-hydroxyethylsulfanyl) propanoic acid, Ahspa; (2S)-2-amino-12-hydroxy-4,7,10-trioxadodecanoic acid, Ahtda; (2S)-2,9-diamino-4,7-dioxanonanoic acid, Dadna; (2S)-2,12-diamino-4,7,10-trioxadodecanoic acid, Datda; (S)-5,5-difluoronorleucine, Dfnl; (S)-4,4-difluoronorvaline, Dfnv; (3R)-1-1-dioxo-[1,4]thiaziane-3-carboxylic acid, Dtca; (S)-4,4,5,5,6,6,6-heptafluoronorleucine, Hfnl; (S)-5,5,6,6,6-pentafluoronorleucine, Pfnl; (S)-4,4,5,5,5-pentafluoronorvaline, Pfnv; and (3R)-1,4-thiazinane-3-carboxylic acid, Tca. Furthermore, the amino acid can be D (dextrorotary) or L (levorotary). For a review of classical and non-classical amino acids, see Sandberg et al., 1998 (Sandberg et al., 1998. New chemical descriptors relevant for the design of biologically active peptides. A multivariate characterization of 87 amino acids. J Med Chem 41 (14): pp. 2481-91).

Properties of Mutant RSV F Molecules

The mutant RSV F molecules of the present invention-including those comprising an amino acid sequence of one of the exemplary amino acid sequences provided herein (e.g. SEQ ID Nos. 21-81), and those comprising residues 26-109 and/or 137-513 of one of such exemplary amino acid sequences, and those comprising an F1 and/or F2 polypeptide of one of such exemplary amino acid sequences, and variant forms of such specific amino sequences—should: (a) comprise an F1 polypeptide and an F2 polypeptide, and (b) be capable of forming, or being processed (e.g. from a precursor such as F0) to form, a mature RSV F trimer capable of adopting a pre-fusion conformation (as described/defined herein). The mutant RSV F molecules of the present invention may, in some embodiments, also have one or more of the following properties: (1) binding to a pre-F specific antibody, (2) binding to an antibody that binds to site ø, (3) binding to a neutralizing antibody, (4) binding to a broadly neutralizing antibody, (5) binding to an antibody selected from the group consisting of D25, AM22, 5C4, 101F, (6) binding to palivizumab (Synagis), (7) binding to and/or activating a B cell receptor, (8) eliciting an anti-RSV antibody response in an animal, (9) eliciting a protective anti-RSV antibody response in an animal, (10) eliciting production of anti-RSV neutralizing antibodies in an animal, (11) eliciting production of anti-RSV broadly neutralizing antibodies in an animal, (12) eliciting production of anti-RSV antibodies that recognize quaternary neutralizing epitopes (QNEs) in an animal, and/or (13) eliciting an anti-RSV protective immune response in an animal.

DT Cross-Linking

In some embodiments the present invention provides mutant RSV F molecules that comprise at least one artificially-introduced DT cross-link. Such DT cross links serve to stabilize the mutant RSV F molecules described herein in their pre-fusion conformation.

In some embodiments such DT cross-links may be introduced between two endogenous tyrosine residues, between two artificially-introduced tyrosine residues (i.e. originating from “to-tyrosine” mutations), or between an artificially-introduced tyrosine residue and an endogenous tyrosine residue.

In some embodiments at least one tyrosine of the at least one DT cross-link derives from (i.e. was introduced by) a point-mutation to tyrosine. In some embodiments the present invention provides a mutant trimeric RSV F molecule comprising at least three DT cross-links, wherein at least one tyrosine of each of the at least three DT cross-links derives from (i.e. was introduced by) a point-mutation to tyrosine.

For example, in some embodiments the present invention provides mutant RSV F molecules comprising a DT cross-link between a tyrosine at residue 198 (typically a naturally occurring tyrosine) and an introduced tyrosine at residue 226 (i.e. resulting from a 226Y mutation)—i.e. an intramolecular 198Y-226Y DT crosslink. In embodiments where the mutant RSV F molecule is a trimer, the trimer thus comprises three intramolecular 198Y-226Y DT cross-links.

In some embodiments the present invention provides mutant RSV F molecules comprising a DT cross-link between an introduced tyrosine at residue185 (i.e. resulting from a185Y mutation) and an introduced tyrosine at residue 428 (i.e. resulting from a 428Y mutation)—i.e. a 185Y-428Y intermolecular DT crosslink. In embodiments where the mutant RSV F molecule is a trimer, the trimer thus comprises three intermolecular 185Y-428Y DT cross-links.

And in some embodiments the present invention provides mutant RSV F molecules comprising both a 198Y-226Y intramolecular DT cross link and a 185Y-428Y intermolecular DT crosslink. In embodiments where the mutant RSV F molecule is a trimer, the trimer thus comprises six DT cross links—three intramolecular 198Y-226Y DT cross-links and three intermolecular 185Y-428Y DT cross-links.

As described above, each protomer of the mature RSV F trimer comprises two distinct polypeptides-termed F1 and F2—which associate non-covalently to form a protomer. A bond between a F1 polypeptide and a F2 polypeptide within the same protomer is an example of an inter-molecular bond and an intra-protomer bond. The 185Y-428Y DT cross-link is designed to hold two protomers of the trimer together—i.e. it is an inter-molecular, inter-protomer bond. The tyrosine at position 185 on one protomer forms a di-tyrosine bond with a tyrosine at position 428 on a different protomer.

Exemplary methods of performing a DT cross-linking reaction are provided in the Examples section of this patent disclosure. Furthermore, methods of performing DT cross-linking are known in the art and are described in, for example, Marshall et al. U.S. Pat. Nos. 7,037,894 and 7,445,912—the contents of which are hereby incorporated by reference. Di-tyrosine cross-linking introduces covalent carbon-carbon bonds that are minimally altering and zero-length. DT cross-links are not hydrolyzed under physiological conditions. Di-tyrosine cross-links are known to be safe, as they form naturally in vivo, and as they are present in large quantities in common foods. For example DT bonds form the structure of wheat gluten. Di-tyrosine bonds do not form spontaneously in vitro. Rather, an enzymatic cross-linking reaction must be performed in which proteins with tyrosyl side chains are subjected to reaction conditions that lead to the formation of DT bonds. Such conditions are, or become, oxidative reaction conditions, as the DT bond formation reaction is an oxidative cross-linking reaction. In some embodiments the DT cross-linking reaction conditions yield proteins that are otherwise not, or not detectably, modified. Such conditions may be obtained by use of enzymes that catalyze the formation of $H_2O_2$, such as peroxidases. DT bond formation may be monitored by spectrophotometry with an excitation wavelength of around 320 nm, and fluorescence measured at a wavelength of around 400 nm (see, for example, FIG. 34), and loss of tyrosyl fluorescence may be monitored by standard procedures. When loss of tyrosyl florescence is no longer stoichiometric with DT bond formation, the reaction may be stopped by any methods known to one skilled in the art, such as, for example, by the addition of a reducing agent and subsequent cooling (on ice) or freezing of the sample. Further details of suitable DT cross-linking methods are described in US Patent Nos. U.S. Pat. Nos. 7,037,894, 7,445,912 and also in the Examples section of this patent disclosure.

Nucleic Acid Molecules

In some embodiments the present invention provides nucleic acid molecules that encode the mutant RSV F molecules described herein, as well vectors comprising such nucleic acid molecules. One of ordinary skill in the art can readily determine the nucleic acid sequence of a nucleic acid molecule that encodes any one of the mutant RSV F molecules described herein—given the universally known and understood nature of the genetic code amongst those of ordinary skill in the art.

In some embodiments, the nucleic acid molecule encodes a precursor F0 polypeptide that, when expressed in an appropriate cell, will be correctly processed to generate a mature RSV F molecule. For example, in some embodiments the nucleic acid molecule may encode one of the precursor (F0) polypeptides for which the amino acid sequences are provided in Table 1 and in the Sequence Listing. In some embodiments, the nucleic acid molecules may encode only a F2 polypeptide or only a F1 polypeptide.

Nucleic acid molecules that encode the mutant RSV F molecules described herein can be obtained or made using any suitable method known in the art. For example, nucleic acid molecules encoding the mutant RSV F molecules may be obtained from cloned DNA or made by chemical synthesis. In some embodiments the nucleic acid molecules may be obtained by reverse transcribing RNA prepared by any of the methods known to one of ordinary skill in the art. Point mutations, or any of the other modifications described herein (e.g. removing C-terminal sequences, substituting C-terminal sequences, etc.), can be made by standard recombinant DNA methodologies that are well known and understood to those of ordinary skill in the art. For example, one of ordinary skill in the art can readily make a "to-tyrosine" mutation as described herein by locating the nucleotide codon that encodes the specific amino acid residue to be mutated to tyrosine (e.g. that encodes amino acid residue 185, 226, or 428), and mutating the nucleotides of that codon as necessary to generate a tyrosine-encoding codon.

Whatever the source, a nucleic acid molecule encoding a mutant RSV F molecule of the present invention can be cloned into any suitable vector, such as those to be used for propagation of the nucleic acid molecule or those to be used for expression of the nucleic acid molecule. In embodiments requiring expression, the nucleic acid can be operatively linked to a promoter suitable for directing expression in the desired cell type, such as a mammalian cell or an insect cell, and may be incorporated into any suitable expression vector, such as a mammalian or insect expression vector.

In some embodiments nucleic acid molecules encoding the mutant RSV F molecules of the present invention can be codon optimized for expression in cells of a particular organism or species. For example, International Patent Application No. PCT/US2014/048086 provides nucleotide sequences of RSV F molecules that have been codon-optimized for expression in human, hamster, mouse, and insect cells. Such codon-optimized nucleotide sequences encoding the RSV F protein can be used as "background" sequences for introduction of any of the specific mutations described herein.

Methods of Manufacture

The mutant RSV F molecules of the invention can be made by any suitable means known in the art. Generally, the mutant RSV F molecules are made using standard methods used for the production of recombinant proteins. For example, nucleic acid molecules encoding a mutant RSV F molecule of the invention can be expressed in any suitable cell type, including, but not limited to mammalian cells and insect cells (such as SF9 or Hi5 cells, e.g. using a baculovirus expression system). Methods for expressing proteins from nucleic acid molecules are routine and well known in the art, and any suitable methods, vectors, systems, and cell types known in the art can be used. For example, typically nucleic acid molecules encoding the mutant RSV F molecules of the invention will be placed into a suitable expression construct containing a suitable promoter, which will then be delivered to cells for expression.

In some embodiments the mutant RSV F molecules of the invention are mature RSV F trimers stabilized in the pre-F conformation. In such embodiments typically nucleic acid molecules encoding the mutant RSV F molecules are expressed in cells in soluble form, and then allowed to assemble into the normal trimeric pre-F conformation before subjecting the molecules to the enzymatic DT cross-linking reaction. In some embodiments, prior to and/or during the enzymatic cross-linking reaction, the mutant RSV F molecules may be obtained in (and/or maintained in) the pre-F conformation, for example while cross-linking is performed. In some embodiments the mutant RSV F molecules may be produced and/or isolated in such a way that most, or substantially all, of the mutant RSV F molecules are present in the pre-F conformation. In some embodiments mutant RSV F molecules in the pre-F conformation may be separated from a mixed population of RSV F protein molecules comprising some that are in the pre-F conformation and some that are in other conformations. In some embodiments, the RSV F protein is expressed in cells (for example as its membrane bound or soluble form) and spontaneously assembles into its normal pre-F conformation. In some embodiments no additional stabilization is necessary to retain the mutant RSV F molecule in its pre-F form prior to DT cross-linking. In some embodiments the mutant RSV F molecule may be kept under particular conditions, or in particular compositions, that favor formation and/or maintenance of the pre-F conformation. For example, in some embodiments the mutant RSVF molecule in its pre-F conformation may be maintained in the absence of cells—contact with which might otherwise trigger a switch to the post-F conformation. The mutant RSV F molecules may be obtained and/or isolated and/or maintained in the pre-F conformation using any suitable method known in the art, including, but not limited to, standard protein purification methods, such as ion exchange chromatography, size exclusion chromatography, and/or affinity chromatography methods. In some embodiments the mutant RSV F molecules may be expressed in the presence of, co-expressed with, or contacted with, molecules that bind to the RSV F protein and stabilize it in its pre-F conformation, including, but not limited to, antibodies, small molecules, peptides, and/or peptidomimetics. Non-limiting examples of antibodies that bind to the pre-fusion RSV F protein include the 5C4, AM22, and D25 antibodies (see Mclellan et al. (2013) Science 342:592-598, which is hereby incorporated by reference in its entirety). In some embodiments, the mutant RSV F molecule may be obtained, isolated, or maintained in its pre-F conformation by controlling the ionic strength of the media/buffer in which the protein is present (such as by using high or low ionic strength media). In some embodiments the mutant RSV F molecules may be obtained, isolated, or maintained at one or more temperatures that favor preservation of the pre-F conformation. In some embodiments the mutant RSV F molecules may be obtained, isolated, or maintained over a period of time that diminishes the degree to which the pre-F conformation is lost.

In some embodiments analysis may be performed to confirm that the desired conformation, such as the pre-F conformation, has been formed and/or maintained in the mutant RSV F molecules. Such analysis may be performed prior to cross-linking, during the cross-linking process, after the cross-linking process, or at any combination of such stages. Such analysis may comprise any suitable methods known in the art for assessing the 3-dimensional structure of a protein or protein complex, including functional analysis, crystallographic analysis, and the like. In some embodiments such analysis may include assessing binding of the mutant RSV F molecules to certain antibodies, such as those that are specific to the pre-F conformation and/or those that are known to bind to the ø site, as described elsewhere herein, including, but not limited to the 5C4, AM22, and D25 antibodies.

In some embodiments the mutant RSV F molecules of the invention may be purified before, during, or after, one or more steps in the manufacturing process. For example, in some embodiments the mutant RSV F molecules may be purified after completion of all of the manufacturing steps. In some embodiments the mutant RSV F molecules may be purified before commencing the cross-linking process, or after one or more of the intermediate method steps in the process, for example: after expression of the mutant RSV F molecule, after assembly of the mutant RSV F molecule into a mature trimer, after obtaining the mutant RSV F molecule in its pre-F conformation, or during or after performing a DT cross-linking reaction. The mutant RSV F molecules of the invention may be isolated or purified using any suitable method known in the art. Such methods include, but are not limited to, chromatography (e.g. ion exchange, affinity, and/or sizing column chromatography), ammonium sulfate precipitation, centrifugation, differential solubility, or by any other technique for the purification of proteins known to one of ordinary skill in the art. In specific embodiments it may be necessary to separate DT cross-linked mature trimeric mutant RSV F molecules from those that were not sufficiently cross-linked, or those in which the pre-F conformation was not sufficiently stabilized. This can be done using any suitable system known in the art. For example, mutant RSV F molecules in the pre-F conformation can be separated from those that are not in the pre-F conformation using antibody-based separation methods using pre-F or post-F specific antibodies. The mutant RSV F molecules of the invention may be purified from any source used to produce them. The degree of purity may vary, but in various embodiments, the purified mutant RSV F molecules of the invention are provided in a form in which is they comprise more than about 10%, 20%, 50%, 70%, 75%, 80%, 85%, 90%, 95%, 98%, 99%, or 99.9% of the total protein in the final composition. In some embodiments the mutant RSV F molecules of the invention may be isolated and purified from other proteins, or any other undesirable products (such as non-cross-linked or non-pre-F RSV F), by standard methods including, but not limited to, chromatography, glycerol gradients, affinity chromatography, centrifugation, ion exchange chromatography, size exclusion chromatography, and affinity chromatography, or by any other standard technique for the purification of proteins known in the art. The mutant RSV F molecules to be isolated may be expressed in high or low ionic media, or isolated in high or low ionic buffers or solutions. The mutant RSV F molecules of the invention may also be isolated at one or more temperatures that favor preservation of the desired conformation. They may also be isolated over a period of time that diminishes the degree to which a preparation would have lost the desired conformation. The degree to which a preparation of proteins retains one or more desired conformations (such as the pre-F conformation) may be assayed by any suitable method known in the art, including, for example, but not limited to, biochemical, biophysical, immunologic, and virologic analyses. Such assays include, for example, but are not limited to, immunoprecipitation, enzyme-linked immunosorbent assays (ELISAs), or enzyme-linked immunosorbent spot (ELISPOT) assays, crystallographic analysis (including co-crystallization with antibodies), sedimentation, analytical ultracentrifugation, dynamic light scattering (DLS), electron microscopy (EM), cryo-EM tomography, calorimetry, surface plasmon resonance (SPR), fluorescence resonance energy transfer (FRET), circular dichroism analysis, and small angle x-ray scattering, neutralization assays, antibody-dependent cellular cytotoxicity assays, and/or virologic challenge studies in vivo.

The yield of the mutant RSV F molecules of the invention can be determined by any means known in the art, for example, by comparing the amount of the final engineered proteins (such as cross-linked pre-F RSV) as compared to the amount of the starting material, or as compared to the amount of the materials present in any preceding step of the production methods. Protein concentrations can be determined by standard procedures, such as, for example, Bradford or Lowrie protein assays. The Bradford assay is compatible with reducing agents and denaturing agents (Bradford, M, 1976. Anal. Biochem. 72:248). The Lowry assay has better compatibility with detergents and the reaction is more linear with respect to protein concentrations and read-out (Lowry, O J, 1951. Biol. Chem. 193:265).

Assays for Properties

In some embodiments the mutant RSV F molecules of the invention, or any intermediates in their manufacture, may be analyzed to confirm that they have desired properties, such as one or more of the properties listed above or identified elsewhere in this patent specification. For example, in some embodiments in vitro or in vivo assays can be performed to assess the RSV F protein's conformational structure, stability (e.g. thermostability), half-life (e.g. inside the body of a subject), aggregation in solution, binding to an antibody (such as a neutralizing antibody, broadly neutralizing antibody; pre-F-specific antibody; antibody that recognizes site ø, conformationally-specific antibody, antibody that recognizes a metastable epitope, D25, AM22, 5C4, 101F or palivizumab), binding to a B cell receptor, activation of a B Cell receptor, antigenicity, immunogenicity, ability to elicit an antibody response, ability to elicit a protective antibody/immune response, ability to elicit production of neutralizing antibodies, or ability to elicit aproduction of broadly neutralizing antibodies. In embodiments where the mutant RSV F molecules of the invention are tested in an animal in vivo, the animal may be any suitable animal species, including, but not limited to a mammal (such as a rodent species (e.g. a mouse or rat), a rabbit, a ferret, a porcine species, a bovine species, an equine species, an ovine species, or a primate species (e.g. a human or a non-human primate), or an avian species (such as a chicken).

Assays for assessing a protein's conformational structure are well known in the art and any suitable assay can be used, including, but not limited to, crystallographic analysis (e.g. X-ray crystallography or electron crystallography), sedimentation analysis, analytical ultracentrifugation, electron microscopy (EM), cryo-electron microscopy (cryo-EM), cryo-EM tomography, nuclear magnetic resonance (NMR), small angle x-ray scattering, fluorescence resonance energy transfer (FRET) assays, and the like.

Assays for assessing a protein's stability are well known in the art and any suitable assay can be used, including, but not limited to, denaturing and non-denaturing electrophoresis, isothermal titration calorimetry, and time-course experiments in which proteins are incubated and analyzed over time at varying protein concentrations, temperatures, pHs or redox conditions. Proteins may also be analyzed for susceptibility to proteolytic degradation.

Assays for assessing binding of proteins to antibodies are well known in the art, and any suitable assay can be used, including, but not limited to, immunoprecipation assays, enzyme-linked immunosorbent assays (ELISAs), enzyme-linked immunosorbent spot assays (ELISPOTs), crystallographic assays (including co-crystallization with antibodies), surface plasmon resonance (SPR) assays, fluorescence resonance energy transfer (FRET) assays, and the like.

Assays for assessing neutralization activity are well known in the art, and any suitable assay can be used. For example, assays can be performed to determine the neutralizing activity of antibodies or antisera generated by vaccination/immunization of animals with the RSV F polypeptides, proteins, and/or protein complexes of the invention. Neutralization assays known in the art include, but are not limited to, those described by Dey et al. 2007 (Dey et al., 2007, Characterization of Human Immunodeficiency Virus Type 1 Monomeric and Trimeric gp120 Glycoproteins Stabilized in the CD4-Bound State: Antigenicity, Biophysics, and Immunogenicity. J Virol 81 (11): 5579-5593) and Beddows et al., 2006 (Beddows et al., 2007, A comparative immunogenicity study in rabbits of disulfide-stabilized proteolytically cleaved, soluble trimeric human immunodeficiency virus type 1 gp140, trimeric cleavage-defective gp140 and momomeric gp120. Virol 360:329-340).

Assays for assessing whether a vaccine immunogen is capable of eliciting an immune response and/or proving protective immunity are well known in the art, and any suitable assay can be used. For example, assays can be performed to determine whether vaccination/immunization of animals with the RSV F polypeptides, proteins, and/or protein complexes of the invention provide an immune response and/or protective immunity against infection with RSV. In some embodiments comparisons may be made between placebo and test vaccinated groups with regard to their rates of infection or sero-conversion or viral loads.

Assays for assessing a protein's pharmacokinetics and bio-distribution are also well known in the art, and any suitable assay can be used to assess these properties of the the RSV F polypeptides, proteins, and/or protein complexes of the invention.

Compositions

In some embodiments the present invention provides compositions comprising one or more of the mutant RSV F molecules described herein. In some embodiments such compositions may be pharmaceutical compositions—i.e. comprising components that are suitable for administration to living subjects.

In some embodiments the mutant RSV F molecules of the invention may be provided in a composition that comprises one or more additional active components, such as one or more additional vaccine immunogens or therapeutic agents.

In some embodiments the mutant RSV F molecules of the invention may be provided in a composition, such as a pharmaceutical composition, that comprises one or more other components, including, but not limited to, pharmaceutically acceptable carriers, adjuvants, immunostimulatory agents, wetting or emulsifying agents, pH buffering agents, preservatives, and/or any other components suitable for the intended use of the compositions. Such compositions can take the form of solutions, suspensions, emulsions and the like. The term "pharmaceutically acceptable carrier" includes various diluents, excipients and/or vehicles in which, or with which, the mutant RSV F molecules of the invention can be provided and includes, but is not limited to, carriers known to be safe for delivery to human and/or other animal subjects, and/or approved by a regulatory agency of the Federal or a state government, and/or listed in the U.S. Pharmacopeia, and/or other generally recognized pharmacopeia, and/or receiving specific or individual approval from one or more generally recognized regulatory agencies for use in humans and/or other animals. Such pharmaceutically acceptable carriers, include, but are not limited to, water, aqueous solutions (such as saline solutions, buffers, and the like), organic solvents (such as certain alcohols and oils, including those of petroleum, animal, vegetable or synthetic origin, such as peanut oil, soybean oil, mineral oil, sesame oil), and the like. In some embodiments the compositions of the invention also comprise one or more adjuvants. Exemplary adjuvants include, but are not limited to, alum adjuvants, inorganic or organic adjuvants, oil-based adjuvants, virosomes, liposomes, lipopolysaccharide (LPS), molecular cages for antigens (such as immune-stimulating complexes ("ISCOMS")), Ag-modified saponin/cholesterol micelles that form stable cage-like structures that are transported to the draining lymph nodes), components of bacterial cell walls, endocytosed nucleic acids (such as double-stranded RNA (dsRNA), single-stranded DNA (ssDNA), and unmethylated CpG dinucleotide-containing DNA), AUM, aluminum phosphate, aluminum hydroxide, and Squalene. In some embodiments virosomes are used as the adjuvant. Additional commercially available adjuvants that can be used in accordance with the present invention include, but are not limited to, the Ribi Adjuvant System (RAS, an oil-in-water emulsion containing detoxified endotoxin (MPL) and mycobacterial cell wall components in 2% squalene (Sigma M6536)), TiterMax (a stable, metabolizable water-in-oil adjuvant (CytRx Corporation 150 Technology Parkway Technology Park/Atlanta Norcross, Georgia 30092)), Syntex Adjuvant Formulation (SAF, an oil-in-water emulsion stabilized by Tween 80 and pluronic polyoxyethlene/polyoxypropylene block copolymer L121 (Chiron Corporation, Emeryville, CA)), Freund's Complete Adjuvant, Freund's Incomplete Adjuvant, ALUM—aluminum hydroxide, Al(OH)3 (available as Alhydrogel, Accurate Chemical & Scientific Co, Westbury, NY), SuperCarrier (Syntex Research 3401 Hillview Ave. P.O. Box 10850 Palo Alto, CA 94303), Elvax 40W1,2 (an ethylene-vinyl acetate copolymer (DuPont Chemical Co. Wilmington, DE)), L-tyrosine co-precipitated with the antigen (available from numerous chemical companies); Montanide (a manide-oleate, ISA Seppic Fairfield, NJ)), AdjuPrime (a carbohydrate polymer), Nitrocellulose-absorbed protein, Gerbu adjuvant (C-C Biotech, Poway, CA), and the like.

In some embodiments the mutant RSV F molecules of the invention may be provided in a composition that comprises a sugar. In some embodiments the RSV F polypeptides, proteins, and/or protein complexes of the invention may be provided in a composition that comprises sucrose. In some embodiments the RSV F polypeptides, proteins, and/or protein complexes of the invention may be provided in a composition that comprises about 5% sucrose. In some embodiments the RSV F polypeptides, proteins, and/or protein complexes of the invention may be provided in a composition that comprises about 10% sucrose. In some embodiments the RSV F polypeptides, proteins, and/or protein complexes of the invention may be provided in a composition that comprises about 15% sucrose. In some embodiments the RSV F polypeptides, proteins, and/or protein complexes of the invention may be provided in a composition that comprises about 20% sucrose. In some embodiments the RSV F polypeptides, proteins, and/or protein complexes of the invention may be provided in a composition that comprises about 25% sucrose. Importantly, it has been found that inclusion of sucrose reduces the formation of aggregates in compositions of the RSV F polypeptides, proteins, and/or protein complexes of the invention.

In some embodiments the present invention provides compositions that comprise an "effective amount" of a mutant RSV F molecule of the invention. Similarly, in some embodiments the present invention provides methods that involve administering an "effective amount" of a mutant RSV F molecule, or a composition comprising a mutant RSV F, to a subject. An "effective amount" is an amount required to achieve a desired end result.

Examples of desired end results include, but are not limited to, the generation of a humoral immune response against RSV, the generation of a neutralizing antibody response against RSV, the generation of a broadly neutralizing antibody response against RSV, the generation of protective immunity against RSV, inhibition or RSV viral replication, and improvement in one or more symptoms of an RSV infection. The amount of a mutant RSV F molecule of the invention, or composition comprising such a molecule, that is effective to achieve the desired end result may depend on variety of factors including, but not limited to, the type, subtype and strain of the RSV virus, the species of the subject (e.g. whether a human or some other animal species), the age of the subject, the sex of the subject, the weight of the subject, the planned route of administration, the planned dosing regimen, the severity of any ongoing RSV infection (e.g. in the case of therapeutic uses), and the like. The effective amount—which may be a range of effective amounts—can be determined by standard techniques without any undue experimentation, for example using in vitro assays and/or in vivo assays in the intended subject species or any suitable animal model species. Suitable assays include, but are not limited to, those that involve extrapolation from dose-response curves and/or other data derived from in vitro and/or in vivo model systems. In some embodiments the effective amount may be determined according to the judgment of a medical or veterinary practitioner based on the specific circumstances.

Uses of Mutant RSV F Molecules

In some embodiments, the mutant RSV F molecules of the invention may be useful as research tools, as diagnostic tools, as therapeutic agents, as targets for the production of antibody reagents or therapeutic antibodies, and/or as vaccines or components of vaccine compositions. For example, in some embodiments the mutant RSV F molecules of the invention are useful as vaccine immunogens in animal subjects, such as mammalian subjectS, including humans. These and other uses of the mutant RSV F molecules of the invention are described more fully below. Those of skill in the art will appreciate that the mutant RSV F molecules of the invention may be useful for a variety of other applications also, and all such applications and uses are intended to fall within the scope of this invention.

Tools for Studying RSV F Antibodies

In one embodiment, the mutant RSV F molecules of the invention may be useful as analytes for assaying and/or measuring binding of, and/or titers of, anti-RSV F antibodies, for example in ELISA assays, Biacore/SPR binding assays, and/or any other assays for antibody binding known in the art. For example, the mutant RSV F molecules of the invention could be used to analyze, and/or compare the efficacy of anti-RSV F antibodies.

Tools for Generation of Antibodies

The mutant RSV F molecules of the invention may also be useful for the generation of therapeutic antibodies and/or antibodies that can be used as research tools or for any other desired use. For example, the mutant RSV F molecules of the invention can be used for immunizations to obtain antibodies to the RSV F protein for use as research tools and/or as therapeutics. In some embodiments the mutant RSV F molecules of the invention can be used to immunize a non-human animal, such as a vertebrate, including, but not limited to, a mouse, rat, guinea pig, rabbit, goat, non-human primate, etc. in order to generate antibodies. Such antibodies, which may be monoclonal or polyclonal, and/or cells that produce such antibodies, can then be obtained from the animal. For example, in some embodiments mutant RSV F molecules of the invention may be used to immunize a mouse and to produce and obtain monoclonal antibodies, and/or hybridomas that produce such monoclonal antibodies. Such methods can be carried out using standard methods known in the art for the production of mouse monoclonal antibodies, including standard methods for hybridoma production. In some embodiments mutant RSV F molecules of the invention may be used for the production of a chimeric (e.g. part-human), humanized, or fully-human antibody, for example using any of the methods currently known in the art for production of chimeric, humanized and fully human antibodies, including, but not limited to, CDR grafting methods, phage-display methods, transgenic mouse methods (e.g. using a mouse that has been genetically altered to allow for the production of fully human antibodies, such as the Xenomouse) and/or any other suitable method known in the art. Antibodies to the mutant RSV F molecules of the invention made using such systems can be characterized antigenically using one or a set of several antigens, preferably including the mutant RSV F molecules of the invention themselves. Additional characterization of such antibodies may be carried out by any standard methods known to one of ordinary skill in the art, including, but not limited to, ELISA-based methods, SPR-based methods, biochemical methods (such as, but not limited to, iso-electric point determination), and methods known in the art for studying biodistribution, safety, and efficacy of antibodies—for example in preclinical and clinical studies.

Administration to Subjects

In some embodiments, the present invention provides methods that comprise administering the mutant RSV F molecules of the invention, or compositions comprising such mutant RSV F molecules, to subjects. Such methods may comprise methods for treating individuals having RSV (i.e. therapeutic methods) and/or methods for protecting individuals against future RSV infection (i.e. prophylactic methods).

Subjects to which the mutant RSV F molecules of the invention, or compositions comprising such RSV F polypeptides, proteins and/or protein complexes, can be administered (for example in the course of a method of treatment or a method of vaccination) include any and all animal species, including, in particular, those that are susceptible to RSV infection or that can provide model animal systems for the study of RSV infection. In some embodiments, the subjects are mammalian species. In some embodiments, the subjects are avian species. Mammalian subjects include, but are not limited to, humans, non-human primates, rodents, rabbits, and ferrets. Avian subjects include, but are not limited to chickens, such as those on poultry farms. In some embodiments the subjects to which the mutant RSV F molecules of the invention, or compositions comprising such mutant RSV F molecules are administered, either have RSV, or are at risk of RSV infection. In some embodiments, the subjects are immuno-compromised. In some embodiments, the subjects have a heart disease or disorder. In some embodiments, the subject is a human of greater than about 50 years in age, or greater than about 55 years in age, or greater than about 60 years in age, or greater than about 65 years in age, or greater than about 70 years in age, or greater than about 75 years in age, or greater than about 80 years in age, or greater than about 85 years in age, or greater than about 90 years in age. In some embodiments, the subject is a human of less than about 1 month in age, or less than about 2 months in age, or less than about 3 months in age, or less than about 4 months in age, or less than about 5 months in age, or less than about 6 months in age, or less than about 7 months in age, or less than about 8 months in age, or less than about 9 months in age, or less than about 10 months in age, or less than about 11 months in age, or less than about 12 months in age, or less than about 13 months in age, or less than about 14 months in age, or less than about 15 months in age, or less than about 16 months in age, or less than about 17 months in age, or less than about 18 months in age, or less than about 19 months in age, or less than about 20 months in age, or less than about 21 months in age, or less than about 22 months in age, or less than about 23 months in age, or less than about 24 months in age.

Various delivery systems are known in the art and any suitable delivery systems can be used to administer the compositions of the present invention to subjects. Such delivery systems include, but are not limited to, intradermal, intramuscular, intraperitoneal, intravenous, subcutaneous, intranasal, epidural, and oral delivery systems. The compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In some embodiments it may be desirable to administer the pharmaceutical compositions of the invention locally to a tissue in which the mutant RSV F molecules may be most effective in generating a desirable outcome. This may be achieved by, for example, local infusion, injection, delivery using a catheter, or by means of an implant, such as a porous, non-porous, or gelatinous implant or an implant comprising one or more membranes (such as sialastic membranes) or fibers from or through which the protein or protein complexes may be released locally. In some embodiments a controlled release system may be used. In some embodiments a pump may be used (see Langer, supra; Sefton, 1987. CRC Crit. Ref. Biomed. Eng. 14:201; Buchwald et al., 1980. Surgery 88:507; Saudek et al., 1989. N. Engl. J. Med. 321:574). In some embodiments polymeric materials may be used to facilitate and/or control release of the mutant RSV F molecules of the invention (see Medical Applications of Controlled Release, Langer and Wise (eds.), 1974. CRC Pres., Boca Raton, Florida; Controlled Drug Bioavailability, 1984. Drug Product Design and Performance, Smolen and Ball (eds.), Wiley, New York; Ranger & Peppas, 1983 Macromol. Sci. Rev. Macromol. Chem. 23:61; see also Levy et al., 1985. Science 228:190; During et al, 1989. Ann. Neurol. 25:351; Howard et al., 1989. J. Neurosurg 71:105). In some embodiments a controlled release system can be placed in proximity to the tissue/organ to which the RSV prefusion F protein or polypeptide is to be delivered (see, e.g., Goodson, 1984. Medical Applications of Controlled Release, supra, vol. 2:115-138). Some suitable controlled release systems that may be used in conjunction with the present invention are described Langer, 1990, Science; vol. 249: pp. 527-1533

In some embodiments, administration of the compositions of the invention can be performed in conjunction with administration of one or more immunostimulatory agents. Non-limiting examples of such immunostimulatory agents include various cytokines, lymphokines and chemokines with immunostimulatory, immuno-potentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory agents, such as macrophage inflammatory factor, Flt3 ligand, B7.1; B7.2. The immunostimulatory agents can be administered in the same formulation as the mutant RSV F molecules, or can be administered separately.

In some embodiments, the mutant RSV F molecules of the invention, or compositions comprising them, can be administered to subjects in a variety of different RSV vaccination methods or regimens. In some such embodiments, administration of a single dose is performed. However, in other embodiments, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against RSV infection. Similarly, adults who are particularly susceptible to RSV infection, such as, for example, the elderly and immunocompromised individuals, may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

In some embodiments, dosing regimens may comprise a single administration/immunization. In other embodiments, dosing regimens may comprise multiple administrations/immunizations. For example, vaccines may be given as a primary immunization followed by one or more boosters. In some embodiments of the present invention such a "prime-boost" vaccination regimen may be used. For example, in some such prime-boost regimens a composition comprising a mutant RSV F molecule as described herein may be administered to an individual on multiple occasions (such as two, three, or even more occasions) separated in time, with the first administration being the "priming" administration and subsequent administrations being "booster" administrations. In other such prime-boost regimens a composition comprising a mutant RSV F molecules as described herein may be administered to an individual after first administering to the individual a composition comprising a viral or DNA vector encoding an RSV polypeptide, protein or protein complex as a "priming" administration, with one or more subsequent "booster" administrations of a composition comprising a RSV F polypeptide, protein or protein complex as described herein. Boosters may be delivered via the same and/or different route as the primary immunization. Boosters are generally administered after a time period after the primary immunization or the previously administered booster. For example, a booster can be given about two weeks or more after a primary immunization, and/or a second booster can be given about two weeks or more after the first boosters. Boosters may be given repeatedly at time periods, for example, about two weeks or greater throughout up through the entirety of a subject's life. Boosters may be spaced, for example, about two weeks, about three weeks, about four weeks, about one month, about two months, about three months, about four months, about five months, about six months, about seven months, about eight months, about nine months, about ten months, about eleven months, about one year, about one and a half years, about two years, about two and a half years, about three years, about three and a half years, about four years, about four and a half years, about five years, or more after a primary immunization or after a previous booster.

In some embodiments the pharmaceutical compositions of the invention may be conveniently provided in unit dosage forms. Unit dosage forms are those containing a single dose or unit (e.g. an effective amount), or an appropriate fraction thereof, of the mutant RSV F molecules of the invention. The unit dosage forms may be presented in single-dose or multi-dose containers.

In some embodiments the compositions of the invention may be provided in sealed ampoules or vials, and may be stored in a freeze-dried (lyophilized) condition requiring only the addition of a sterile liquid carrier (e.g. water) immediately prior to use.

Kits

The present invention further provides kits comprising mutant RSV F molecules of the invention, or compositions containing such mutant RSV F molecules. To facilitate use of the methods and compositions of the invention, any of the components and/or compositions described herein, and additional components useful for experimental or therapeutic or vaccine purposes, can be packaged in the form of a kit. Typically, the kit contains, in addition to the above components, additional materials which can include, e.g., instructions for using the components, packaging material, a container, and/or a delivery device.

TABLE 1

| Exemplary Amino Acid Sequences | | | |
|---|---|---|---|
| SEQ ID | Background Sequence | Introduced Mutations | Amino Acid Sequence |
| 1 | RSV A: A2 (138251) | None (WT) | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPPTN<br>NRARRELPRFMNYTLNNAKKTNVTLSKKRKRRFLGFLLGVGSAIASGVAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEINLCNVDIFNPKYDCKIMTSKTDVSSSVITSLGAIVSC<br>YGKTKCTASNKNRGIIKTFSNGCDYVSNKGMDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 2 | RSV A: *Homo sapiens*/USA/ LA2_55/2013 (AHX57020.1) | None (WT) | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>SRARRELPRFMNYTLNNTKNTNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSSNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLALIAVGLLLYCKARSTPVILSNDQLSGINNIAF*<br>*SN* |
| 3 | RSV A: A/WI/629-4071/98 (AEQ63520) | None (WT) | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNTNVTVSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 4 | RSV A: TX-79223 (AGG39418) | None (WT) | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNTNVTVSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 5 | RSV A: BE08-5146 (AFM55563) | None (WT) | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTQAAN<br>SRARRELPRFMNYTLNNTKNTNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 6 | RSV A: Tracy (AGG39397) | None (WT) | MELPIIKANAITTILIAVTFCFASSQNITEEFYQSTCSAVSKGYLSALRTGW<br>YTSVITIELSNIKENKCNGTDAKVKLIKQELDKYKNAVTELQLLMQSTTAAN<br>NRARRELPRFMNYTLNNAKKTNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQADTCKVQSNR |

TABLE 1-continued

Exemplary Amino Acid Sequences

| SEQ ID | Background Sequence | Introduced Mutations | Amino Acid Sequence |
|---|---|---|---|
| | | | VFCDTMNSLTLPSEVNLCNIDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 7 | RSV A:<br>RSV-4<br>(AEO45850) | None (WT) | MELPILKTNAITTILTAVTFCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNNNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNVGK*<br>*STTNIMITTIIIVIIVILLLLIAVGLLLYCKARSTPVTLSNDQLSGINNIAF*<br>*SN* |
| 8 | RSV A: 06-<br>000827<br>(AFM55442) | None (WT) | MELPILKTNAITTIFAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNNNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNVGK*<br>*STTNIMITTIIIVIIVILLLLIAVGLFLYCKARSTPVTLSKEQLSGINNIAF*<br>*SN* |
| 9 | RSV A:<br>RSVA/*Homo*<br>*sapiens*/USA/<br>901-<br>226A-<br>01/1990<br>(AHY21463) | None (WT) | MELPILKTNAITTIFAAVTLCFASSQNITEEFYQSTCSAVSKGYLSALRTGW<br>YTSVITVELSNIKENKCNGTDAKVKLIKQELDKYKNAVTELQLLMQSTPAAN<br>NRARRELPRFMNYTLNNTKNTNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSKDQLSGINNIAF*<br>*SN* |
| 10 | RSV A:<br>RSV/A2<br>5W23_A | None (WT) | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*SAIGGYI*<br>*PEAPRDGQAYVRKDGEWVLLSTFLGGLVPRGSHHHHHHSAWSHPQFEK* |
| 11 | RSV B:<br>18537<br>(138250) | None (WT) | MELLIHRSSAIFLTLAVNALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNGVSVLTSKVLDLKNYINNRLLPIVN<br>QQSCRISNIETVIEFQQMNSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNKNRGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITTIIIVIIVVLLSLIAIGLLLYCKAKNTPVTLSKDQLSGINNIAF*<br>*SK* |

TABLE 1-continued

Exemplary Amino Acid Sequences

| SEQ ID | Background Sequence | Introduced Mutations | Amino Acid Sequence |
|---|---|---|---|
| 12 | RSV B: RSVB/*Homo sapiens*/PER/FPP00592/2011 (AHV80758) | None (WT) | MELLIHRSSAIFLTLAINALYLTSSQNITEEFYQSTCSAVSRGYFSALRTGWYTSVITIELSNIKETKCNGTDTKVKLIKQELDKYKNAVTELQLLMQNTPAANNRARREAPQYMNYTINTTKNLNVSISKKRKRRFLGFLLGVGSAIASGIAVSKVLHLEGEVNKIKNALLSTNKAVVSLSNGVSVLTSKVLDLKNYINNQLLPIVNQQSCRISNIETVIEFQQKNSRLLEITREFSVNAGVTTPLSTYMLTNSELLSLINDMPITNDQKKLMSSNVQIVRQQSYSIMSIIKEEVLAYVVQLPIYGVIDTPCWKLHTSPLCTTNIKEGSNICLTRTDRGWYCDNAGSVSFFPQADTCKVQSNRVFCDTMNSLTLPSEVSLCNTDIFNSKYDCKIMTSKTDISSSVITSLGAIVSCYGKTKCTASNKNRGIIKTFSNGCDYVSNKGVDTVSVGNTLYYVNKLEGKNLYVKGEPIINYYDPLVFPSDEFDASISQVNEKINQSLAFIRRSDELL*HNVNTGKSTTNIMITAIIIVIIVVLLSLIAIGLLLYCKAKNTPVTLSKDQLSGINNIAFSK* |
| 13 | RSV B: NH1144 (AFD34260) | None (WT) | MELLIHRSSAIFLTLAINALYLTSSQNITEEFYQSTCSAVSRGYFSALRTGWYTSVITIELSNIKETKCNGTDTKVKLIKQELDKYKNAVTELQLLMQNTPAANNRARREAPQYMNYTINTTKNLNVSISKKRKRRFLGFLLGVGSAIASGIAVSKVLHLEGEVNKIKNALLSTNKAVVSLSNGVSVLTSKVLDLKNYINNQLLPIVNKQSCRISNIETVIEFQQKNSRLLEITREFSVNAGVTTPLSTYMLTNSELLSLINDMPITNDQKKLMSSNVQIVRQQSYSIMSIIKEEVLAYVVQLPIYGVIDTPCWKLHTSPLCTTNIKEGSNICLTRTDRGWYCDNAGSVSFFPQADTCKVQSNRVFCDTMNSLTLPSEVSLCNTDIFNSKYDCKIMTSKTDVSSSVITSLGAIVSCYGKTKCTASNKNRGIIKTFSNGCDYVSNKGVDTVSVGNTLYYVNKLEGKNLYVKGEPIINYYDPLVFPSDEFDASISQVNEKINQSLAFIRRSDELL*HNVNTGKSTTNIMITAIIIVIIVVLLSLIAIGLLLYCKAKNTPVTLSKDQLSGINNIAFSK* |
| 14 | RSV B: TX-79247 (AGG39514) | None (WT) | MELLIHRSSAIFLTLAINALYLTSSQNITEEFYQSTCSAVSRGYLSALRTGWYTSVITIELSNIKETKCNGTDTKVKLIKQELDKYKNAVTELQLLMQNTPVANNRARREAPQYMNYTINTTKNLNVSISKKRKRRFLGFLLGVGSAIASGIAVSKVLHLEGEVNKIKNALLSTNKAVVSLSNGVSVLTSKVLDLKNYINNQLLPIVNQQSCRISNIETVIEFQQKNSRLLEITREFSVNAGVTTPLSTYMLTNSELLSLINDMPITNDQKKLMSSNVQIVRQQSYSIMSIIKEEVLAYVVQLPIYGVIDTPCWKLHTSPLCTTNTKEGSNICLTRTDRGWYCDNAGSVSFFPQADTCKVQSNRVFCDTMYSLTLPSEVSLCNTDIFNSKYDCKIMTSKTDISSSVITSLGAIVSCYGKTKCTASNKNRGIIKTFSNGCDYVSNKGVDTVSVGNTLYYVNKLEGKNLYVKGEPIINYYDPLVFPSDEFDASISQVNEKINQSLAFIRRSDELL*HNVNTGKSTTNIMITAIIIVIIVVLLSLIAIGLLLYCKAKNTPVTLSKDQLSGINNIAFSK* |
| 15 | RSV B: CH-18537 (AGG39487) | None (WT) | MELLIHRSSAIFLTLAVNALYLTSSQNITEEFYQSTCSAVSRGYFSALRTGWYTSVITIELSNIKETKCNGTDTKVKLIKQELDKYKNAVTELQLLMQNTPAANNRARREAPQYMNYTINTTKNLNVSISKKRKRRFLGFLLGVGSAIASGMAVSKVLHLEGEVNKIKNALLSTNKAVVSLSNGISVLTSKVLDLKNYINNRLLPIVNQQSCRISNIETVIEFQQKNSRLLEITREFSVNAGVTTPLSTYMLTNSELLSLINDMPITNDQKKLMSSNVQIVRQQSYSIMSIIKEEVLAYVVQLPIYGVIDTPCWKLHTSPLCTTNIKEGSNICLTRTDRGWYCDNAGSVSFFPQADTCKVQSNRVFCDTMNSLTLPSEVSLCNTDIFNSKYDCKIMTSKTDISSSVITSLGAIVSCYGKTKCTASNKNRGIIKTFSNGCDYVSNKGVDTVSVGNTLYYVNKLEGKNLYVKGEPIINYYDPLVFPSDEFDASISQVNEKINQSLAFIRRSDEL*LHNVNTGKSTTNIMITTIIIVIIVVLLSLIAIGLLLYCKAKNTPVTLSKDQLSGINNIAFSK* |
| 16 | RSV B: NH1125 (AF125251) | None (WT) | MELLIHRSSAIFLTLAINALYLTSSQNITEEFYQSTCSAVSRGYFSALRTGWYTSVITIELSNIKETKCNGTDTKVKLIKQELDKYKNAVTELQLLMQNTPAANNRARREAPQYMNYTINTTKNLNVSISKKRKRRFLGFLLGVGSAIASGIAVSKVLHLEGEVNKIKNALLSTNKAVVSLSNGVSVLTSKVLDLKNYINNQLLPIVNQQSCRISNIETVIEFQQKNSRLLEITREFSVNAGVTTPLSTYMLTNSELLSLINDMPITNDQKKLMSSNVQIVRQQSYSIMSIMKEEVLAYVVQLPIYGVIDTPCWKLHTSPLCTTNIKEGSNICLTRTDRGWYCDNAGSVSFFPQADTCKVQSNRVFCDTMNSLTLPSEVSLCNTDIFNSKYDCKIMTSKTDISSSVITSLGAIVSCYGKTKCTASNKNRGIIKTFSNGCDYVSNKGVDTVSVGNTLYYVNKLEGKNLYVKGEPIINYYDPLVFPSDEFDASISQVNEKINQSLAFIRRSDELL*HNVNTGKSTTNIMITVIIIVIIVVLLSLIAIGLLLYCKAKNTPVTLSKDQLSGINNIAFSK* |
| 17 | RSV B: TX-79222 (AGG39523) | None (WT) | MELLIHRSIAIFLTLAINALYLTSSQNITEEFYQSTCSAVSRGYFSALRTGWYTSVITIELSNITETKCNGTDTKVKLIKQELDKYKNAVTELQLLMQNTPAANNRARREAPQYMNYTINTTKNLNVSISKKRKRRFLGFLLGVGSAIASGIAVSKVLHLEGEVNKIKNALLSTNKAVVSLSNGVSVLTSKVLDLKNYINNQLLPIVNQQSCRISNIETVIEFQQKNSRLLEITREFSVNAGVTTPLSTYMLTNSELLSLINDMPITNDQKKLMSSNVQIVRQQSYSIMSIIKEEVLAYVVQLPIYGVIDTPCWKLHTSPLCTTNIKEGSNICLTRTDRGWYCDNAGSVSFFPQADTCKVQSNRVFCDTMNSLTLPSEVSLCNTDIFNSKYDCKIMTSKTDISSSVITSLGAIVSC |

TABLE 1-continued

| Exemplary Amino Acid Sequences | | | |
|---|---|---|---|
| SEQ ID | Background Sequence | Introduced Mutations | Amino Acid Sequence |
| | | | YGKTKCTASNKNRGIIKTFSNGCDYVSNKGVDTVSVGNTLYYVNKLEGKNLY<br>VKGEPIINYYDPLVFPSDEFDASISQVNEKINQSLAFIRRSDELL*HNVNVGK*<br>*STTNIMITAIIIVIIVVLLSLIAIGLLLYCKAKNTPVTLSKDQLSGINNIAF*<br>*SK* |
| 18 | RSV B: TX-60567 (AGG39502) | None (WT) | MELLVHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTNNLNVSISKKRKRRFLGFLLGVGSAIASGIAVSK<br>VLHLEGEVNKIKNALLSTNKAVVSLSNGVSVLTSKVLDLKNYINNQLLPIVN<br>QQSCRISNIETVIEFQQKNSRLLEIAREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNKNRGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 19 | RSV B: 138250 (BAA00240.1) | None (WT) | MELLIHRSSAIFLTLAVNALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNGVSVLTSKVLDLKNYINNRLLPIVN<br>QQSCRISNIETVIEFQQMNSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNKNRGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITTIIIVIIVVLLSLIAIGLLLYCKAKNTPVTLSKDQLSGINNIAF*<br>*SK* |
| 20 | RSV B: (AHJ60043.1) | None (WT) | MELLIHRSSAIFLTLAINALYLTSSQNITEEFYQSTCSAVSRGYFSALRTGW<br>YTSVITIELSNITETKCNGTDTKVKLIKQELDKYKNAVTELQLLMQNTPAAN<br>NRARREAPQHMNYTINTTKNLNVSISKKRKRRFLGFLLGVGSAIASGIAVSK<br>VLHLEGEVNKIKNALLSTNKAVVSLSNGVSVLTSKVLDLKNYINNQLLPIVN<br>QQSCRIFNIETVIEFQQKNSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNKNRGIIKTFSNGCDYVSNKGVDTVSVGNTLYYVNKLEGKNLY<br>VKGEPIINYYDPLVFPSDEFDASISQVNEKINQSLAFIRKSDELL*HNVNTGK*<br>*STTNIMITTIIIVIIVVLLSLIAIGLLLYCKAKNTPVTLSKDQLSGINNIAF*<br>*SK* |
| 21 | RSV A: A2 (138251) | 428Y | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPPTN<br>NRARRELPRFMNYTLNNAKKTNVTLSKKRKRRFLGFLLGVGSAIASGVAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEINLCNVDIFNPKYDCKIMTSKTDVSSSVITSLGAIVSC<br>YGKTKCTASNK**Y**RGIIKTFSNGCDYVSNKGMDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSKDQLSGINNIAF*<br>*SN* |
| 22 | RSV A: *Homo sapiens*/USA/LA2_55/2013 (AHX57020.1) | 428Y | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>SRARRELPRFMNYTLNNTKNTNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSSNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLALIAVGLLLYCKARSTPVILSKDQLSGINNIAF*<br>*SN* |
| 23 | RSV A: A/WI/629-4071/98 (AEQ63520) | 428Y | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNTNVTVSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL |

TABLE 1-continued

Exemplary Amino Acid Sequences

| SEQ ID | Background Sequence | Introduced Mutations | Amino Acid Sequence |
|---|---|---|---|
| | | | INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSKDQLSGINNIAF*<br>*SN* |
| 24 | RSV A: TX-79223 (AGG39418) | 428Y | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNTNVTVSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 25 | RSV A: BE08-5146 (AFM55563) | 428Y | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTQAAN<br>SRARRELPRFMNYTLNNTKNTNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 26 | RSV A: Tracy (AGG39397) | 428Y | MELPIIKANAITTILIAVTFCFASSQNITEEFYQSTCSAVSKGYLSALRTGW<br>YTSVITIELSNIKENKCNGTDAKVKLIKQELDKYKNAVTELQLLMQSTTAAN<br>NRARRELPRFMNYTLNNAKKTNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQADTCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 27 | RSV A: RSV-4 (AEO45850) | 428Y | MELPILKTNAITTILTAVTFCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNNNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNVGK*<br>*STTNIMITTIIIVIIVILLLLIAVGLLLYCKARSTPVTLSNDQLSGINNIAF*<br>*SN* |
| 28 | RSV A: 06-000827 (AFM55442) | 428Y | MELPILKTNAITTIFAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNNNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNVGK*<br>*STTNIMITTIIIVIIVILLLLIAVGLFLYCKARSTPVTLSKEQLSGINNIAF*<br>*SN* |

TABLE 1-continued

Exemplary Amino Acid Sequences

| SEQ ID | Background Sequence | Introduced Mutations | Amino Acid Sequence |
|---|---|---|---|
| 29 | RSV A: RSVA/*Homo sapiens*/USA/ 901- 226A- 01/1990 (AHY21463) | 428Y | MELPILKTNAITTIFAAVTLCFASSQNITEEFYQSTCSAVSKGYLSALRTGW<br>YTSVITVELSNIKENKCNGTDAKVKLIKQELDKYKNAVTELQLLMQSTPAAN<br>NRARRELPRFMNYTLNNTKNTNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 30 | RSV A: RSV/A2 5W23_A | 428Y | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*SAIGGYI*<br>*PEAPRDGQAYVRKDGEWVLLSTFLGGLVPRGSHHHHHHSAWSHPQFEK* |
| 31 | RSV B: 18537 (138250) | 428Y | MELPILKTNAITTIFAAVTLCFASSQNITEEFYQSTCSAVSKGYLSALRTGW<br>YTSVITVELSNIKENKCNGTDAKVKLIKQELDKYKNAVTELQLLMQSTPAAN<br>NRARRELPRFMNYTLNNTKNTNVTLSKKRKRRFLGFLLGVGSAIASGIAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSKDQLSGINNIAF*<br>*SN* |
| 32 | RSV B: RSVB/*Homo sapiens*/PER/ FPP00592/ 2011 (AHV80758) | 428Y | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNGVSVLTSKVLDLKNYINNQLLPIVN<br>QQSCRISNIETVIEFQQKNSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 33 | RSV B: NH1144 (AFD34260) | 428Y | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNGVSVLTSKVLDLKNYINNQLLPIVN<br>KQSCRISNIETVIEFQQKNSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDVSSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*S* |
| 34 | RSV B: TX- 79247 (AGG39514) | 428Y | MELLIHRSSAIFLTLAINALYLTSSQNITEEFYQSTCSAVSRGYLSALRTGW<br>YTSVITIELSNIKETKCNGTDTKVKLIKQELDKYKNAVTELQLLMQNTPVAN<br>NRARREAPQYMNYTINTTKNLNVSISKKRKRRFLGFLLGVGSAIASGIAVSK<br>VLHLEGEVNKIKNALLSTNKAVVSLSNGVSVLTSKVLDLKNYINNQLLPIVN<br>QQSCRISNIETVIEFQQKNSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNTKEGSNICLTRTDRGWYCDNAGSVSFFPQADTCKVQSNR<br>VFCDTMYSLTLPSEVSLCNTDIFNSKYDCKIMTSKTDISSSVITSLGAIVSC |

TABLE 1-continued

| Exemplary Amino Acid Sequences | | | |
|---|---|---|---|
| SEQ ID | Background Sequence | Introduced Mutations | Amino Acid Sequence |
| | | | YGKTKCTASNKYRGIIKTFSNGCDYVSNKGVDTVSVGNTLYYVNKLEGKNLY<br>VKGEPIINYYDPLVFPSDEFDASISQVNEKINQSLAFIRRSDELLHNVNTGK<br>STTNIMITAIIIVIIVVLLSLIAIGLLLYCKAKNTPVTLSKDQLSGINNIAF<br>SK |
| 35 | RSV B: CH-18537 (AGG39487) | 428Y | MELLIHRSSAIFLTLAINALYLTSSQNITEEFYQSTCSAVSRGYLSALRTGW<br>YTSVITIELSNIKETKCNGTDTKVKLIKQELDKYKNAVTELQLLMQNTPVAN<br>NRARREAPQYMNYTINTTKNLNVSISKKRKRRFLGFLLGVGSAIASGIAVSK<br>VLHLEGEVNKIKNALLSTNKAVVSLSNGVSVLTSKVLDLKNYINNQLLPIVN<br>QQSCRISNIETVIEFQQKNSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNTKEGSNICLTRTDRGWYCDNAGSVSFFPQADTCKVQSNR<br>VFCDTMYSLTLPSEVSLCNTDIFNSKYDCKIMTSKTDISSSVITSLGAIVSC<br>YGKTKCTASNKYRGIIKTFSNGCDYVSNKGVDTVSVGNTLYYVNKLEGKNLY<br>VKGEPIINYYDPLVFPSDEFDASISQVNEKINQSLAFIRRSDELLHNVNTGK<br>STTNIMITAIIIVIIVVLLSLIAIGLLLYCKAKNTPVTLSKDQLSGINNIAF<br>SK |
| 36 | RSV B: NH1125 (AF125251) | 428Y | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNGVSVLTSKVLDLKNYINNQLLPIVN<br>QQSCRISNIETVIEFQQKNSRLLEITREFSVNAGVTTPLSTYMLTNSELLSL<br>INDMPITNDQKKLMSSNVQIVRQQSYSIMSIMKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNKYRGIIKTFSNGCDYVSNKGVDTVSVGNTLYYVNKLEGKNLY<br>VKGEPIINYYDPLVFPSDEFDASISQVNEKINQSLAFIRRSDELLHNVNTGK<br>STTNIMITVIIIVIIVVLLSLIAIGLLLYCKAKNTPVTLSKDQLSGINNIAF<br>SK |
| 37 | RSV B: TX-79222 (AGG39523) | 428Y | MELLIHRSIAIFLTLAINALYLTSSQNITEEFYQSTCSAVSRGYFSALRTGW<br>YTSVITIELSNITETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNGVSVLTSKVLDLKNYINNQLLPIVN<br>QQSCRISNIETVIEFQQKNSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNKYRGIIKTFSNGCDYVSNKGVDTVSVGNTLYYVNKLEGKNLY<br>VKGEPIINYYDPLVFPSDEFDASISQVNEKINQSLAFIRRSDELLHNVNVGK<br>STTNIMITAIIIVIIVVLLSLIAIGLLLYCKAKNTPVTLSKDQLSGINNIAF<br>SK |
| 38 | RSV B: TX-60567 (AGG39502) | 428Y | MELLVHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTNNLNVSISKKRKRRFLGFLLGVGSAIASGIAVSK<br>VLHLEGEVNKIKNALLSTNKAVVSLSNGVSVLTSKVLDLKNYINNQLLPIVN<br>QQSCRISNIETVIEFQQKNSRLLEIAREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNKYRGIIKTFSNGCDYVSNKGVDTVSVGNTLYYVNKLEGKNLY<br>VKGEPIINYYDPLVFPSDEFDASISQVNEKINQSLAFIRRSDELLHNVNTGK<br>STTNIMITAIIIVIIVVLLSLIAIGLLLYCKAKNTPVTLSKDQLSGINNIAF<br>SK |
| 39 | RSV B: 138250 (BAA00240.1) | 428Y | MELLIHRSSAIFLTLAVNALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNGVSVLTSKVLDLKNYINNRLLPIVN<br>QQSCRISNIETVIEFQQMNSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNKYRGIIKTFSNGCDYVSNKGVDTVSVGNTLYYVNKLEGKNLY<br>VKGEPIINYYDPLVFPSDEFDASISQVNEKINQSLAFIRRSDELLHNVNTGK<br>STTNIMITTIIIVIIVVLLSLIAIGLLLYCKAKNTPVTLSKDQLSGINNIAF<br>SK |
| 40 | RSV B: (AHJ60043.1) | 428Y | MELLIHRSSAIFLTLAINALYLTSSQNITEEFYQSTCSAVSRGYFSALRTGW<br>YTSVITIELSNITETKCNGTDTKVKLIKQELDKYKNAVTELQLLMQNTPAAN<br>NRARREAPQHMNYTINTTKNLNVSISKKRKRRFLGFLLGVGSAIASGIAVSK<br>VLHLEGEVNKIKNALLSTNKAVVSLSNGVSVLTSKVLDLKNYINNQLLPIVN<br>QQSCRIFNIETVIEFQQKNSRLLEITREFSVNAGVTTPLSTYMLTNSELLSL |

TABLE 1-continued

| Exemplary Amino Acid Sequences | | | |
|---|---|---|---|
| SEQ ID | Background Sequence | Introduced Mutations | Amino Acid Sequence |
| | | | INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRKSDELL*HNVNTGK*<br>*STTNIMITTIIIVIIVVLLSLIAIGLLLYCKAKNTPVTLSKDQLSGINNIAF*<br>*SK* |
| 41 | RSV A: A2 (138251) | 185Y<br>226Y<br>428Y | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPPTN<br>NRARRELPRFMNYTLNNAKKTNVTLSKKRKRRFLGFLLGVGSAIASGVAVSK<br>VLHLEGEVNKIKSALLSTNKAVVSLSNG**Y**SVLTSKVLDLKNYIDKQLLPIVN<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEINLCNVDIFNPKYDCKIMTSKTDVSSSVITSLGAIVSC<br>YGKTKCTASNK**Y**RGIIKTFSNGCDYVSNKGMDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 42 | RSV A: *Homo sapiens*/USA/ LA2_55/2013 (AHX57020.1) | 185Y<br>226Y<br>428Y | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>SRARRELPRFMNYTLNNTKNTNVTLSKKRKRRFLGFLLGVGSAIASGIAVSK<br>VLHLEGEVNKIKSALLSTNKAVVSLSNG**Y**SVLTSKVLDLKNYIDKQLLPIVN<br>KQSCSISNIETVIEFQQ**Y**NNRLLEITREFSVNAGVTTPVSTYMLTNSELLSL<br>INDMPITNDQKKLMSSNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLALIAVGLLLYCKARSTPVILSNDQLSGINNIAF*<br>*SN* |
| 43 | RSV A: A/WI/629-4071/98 (AEQ63520) | 185Y<br>226Y<br>428Y | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNTNVTVSKKRKRRFLGFLLGVGSAIASGIAVSK<br>VLHLEGEVNKIKSALLSTNKAVVSLSNG**Y**SVLTSKVLDLKNYIDKQLLPIVN<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |
| 44 | RSV A: TX-79223 (AGG39418) | 185Y<br>226Y<br>428Y | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKTTNVTLSKKRKRRFLGFLLGVGSAIASGIAVSK<br>VLHLEGEVNKIKSALLSTNKAVVSLSNG**Y**SVLTSKVLDLKNYIDKQLLPIVN<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNTDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SS* |
| 45 | RSV A: BE08-5146 (AFM55563) | 185Y<br>226Y<br>428Y | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTQAAN<br>SRARRELPRFMNYTLNNTKNTNVTLSKKRKRRFLGFLLGVGSAIASGIAVSK<br>VLHLEGEVNKIKSALLSTNKAVVSLSNG**Y**SVLTSKVLDLKNYIDKQLLPIVN<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSNDQLSGINNIAF*<br>*SN* |

TABLE 1-continued

| Exemplary Amino Acid Sequences | | | |
|---|---|---|---|
| SEQ ID | Background Sequence | Introduced Mutations | Amino Acid Sequence |
| 46 | RSV A: Tracy (AGG39397) | 185Y<br>226Y<br>428Y | MELLVHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTNNLNVSISKKRKRRFLGFLLGVGSAIASGIAVSK<br>VLHLEGEVNKIKNALLSTNKAVVSLSNG**Y**SVLTSKVLDLKNYINNQLLPIVN<br>QQSCRISNIETVIEFQQ**Y**NSRLLEIAREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 47 | RSV A: RSV-4 (AEO45850) | 185Y<br>226Y<br>428Y | MELPILKTNAITTILTAVTFCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNNNVTLSKKRKRRFLGFLLGVGSAIASGIAVSK<br>VLHLEGEVNKIKSALLSTNKAVVSLSNG**Y**SVLTSKVLDLKNYIDKQLLPIVN<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNVGK*<br>*STTNIMITTIIIVIIVILLLLIAVGLLLYCKARSTPVTLSKDQLSGINNIAF*<br>*SN* |
| 48 | RSV A: 06-000827 (AFM55442) | 185Y<br>226Y<br>428Y | MELPILKTNAITTIFAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNNNVTLSKKRKRRFLGFLLGVGSAIASGIAVSK<br>VLHLEGEVNKIKSALLSTNKAVVSLSNG**Y**SVLTSKVLDLKNYIDKQLLPIVN<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNVGK*<br>*STTNIMITTIIIVIIVILLLLIAVGLFLYCKARSTPVTLSKEQLSGINNIAF*<br>*SN* |
| 49 | RSV A: RSVA/*Homo sapiens*/USA/901-226A-01/1990 (AHY21463) | 185Y<br>226Y<br>428Y | MELPILKTNAITTIFAAVTLCFASSQNITEEFYQSTCSAVSKGYLSALRTGW<br>YTSVITVELSNIKENKCNGTDAKVKLIKQELDKYKNAVTELQLLMQSTPAAN<br>NRARRELPRFMNYTLNNTKNTNVTLSKKRKRRFLGFLLGVGSAIASGIAVSK<br>VLHLEGEVNKIKSALLSTNKAVVSLSNG**Y**SVLTSKVLDLKNYIDKQLLPIVN<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSKDQLSGINNIAF*<br>*SN* |
| 50 | RSV A: RSV/A2 5W23_A | 185Y<br>226Y<br>428Y | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVSK<br>VLHLEGEVNKIKSALLSTNKAVVSLSNG**Y**SVLTSKVLDLKNYIDKQLLPIVN<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*SAIGGYI*<br>*PEAPRDGQAYVRKDGEWVLLSTFLGGLVPRGSHHHHHHSAWSHPQFEK* |
| 51 | RSV B: 18537 (138250) | 185Y<br>226Y<br>428Y | MELLIHRSSAIFLTLAVNALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNG**Y**SVLTSKVLDLKNYINNRLLPIVN<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC |

TABLE 1-continued

| SEQ ID | Background Sequence | Introduced Mutations | Amino Acid Sequence |
|---|---|---|---|
| Exemplary Amino Acid Sequences | | | |
| | | | YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITTIIIVIIVVLLSLIAIGLLLYCKAKNTPVTLSKDQLSGINNIAF*<br>*SK* |
| 52 | RSV B: RSVB/*Homo sapiens*/PER/ FPP00592/ 2011 (AHV80758) | 185Y<br>226Y<br>428Y | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNG**Y**SVLTSKVLDLKNYINNQLLPIVN<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 53 | RSV B: NH1144 (AFD34260) | 185Y<br>226Y<br>428Y | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNG**Y**SVLTSKVLDLKNYINNQLLPIVN<br>KQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDVSSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*S* |
| 54 | RSV B: TX-79247 (AGG39514) | 185Y<br>226Y<br>428Y | MELLIHRSSAIFLTLAINALYLTSSQNITEEFYQSTCSAVSRGYLSALRTGW<br>YTSVITIELSNIKETKCNGTDTKVKLIKQELDKYKNAVTELQLLMQNTPVAN<br>NRARREAPQYMNYTINTTKNLNVSISKKRKRRFLGFLLGVGSAIASGIAVSK<br>VLHLEGEVNKIKNALLSTNKAVVSLSNG**Y**SVLTSKVLDLKNYINNQLLPIVN<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNTKEGSNICLTRTDRGWYCDNAGSVSFFPQADTCKVQSNR<br>VFCDTMYSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 55 | RSV B: CH-18537 (AGG39487) | 185Y<br>226Y<br>428Y | MELLIHRSSAIFLTLAVNALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGMAVSK<br>VLHLEGEVNKIKNALLSTNKAVVSLSNG**Y**SVLTSKVLDLKNYINNRLLPIVN<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITTIIIVIIVVLLSLIAIGLLLYCKAKNTPVTLSKDQLSGINNIAF*<br>*SK* |
| 56 | RSV B: NH1125 (AF125251) | 185Y<br>226Y<br>428Y | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNG**Y**SVLTSKVLDLKNYINNQLLPIVN<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 57 | RSV B: TX-79222 (AGG39523) | 185Y<br>226Y<br>428Y | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNG**Y**SVLTSKVLDLKNYINNQLLPIVN<br>KQSCRISNIETVIEFQQ**Y**NSRLLEITREFSVNAGVTTPLSTYMLTNSELLSL |

TABLE 1-continued

| SEQ ID | Background Sequence | Introduced Mutations | Amino Acid Sequence |
|---|---|---|---|
| | | | INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDVSSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*S* |
| 58 | RSV B: TX-60567 (AGG39502) | 185Y<br>226Y<br>428Y | MELLIHRSSAIFLTLAINALYLTSSQNITEEFYQSTCSAVSRGYLSALRTGW<br>YTSVITIELSNIKETKCNGTDTKVKLIKQELDKYKNAVTELQLLMQNTPVAN<br>NRARREAPQYMNYTINTTKNLNVSISKKRKRRFLGFLLGVGSAIASGIAVSK<br>VLHLEGEVNKIKNALLSTNKAVVSLSNG**Y**SVLTSKVLDLKNYINNQLLPIVN<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNTKEGSNICLTRTDRGWYCDNAGSVSFFPQADTCKVQSNR<br>VFCDTMYSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 59 | RSV B: 138250 (BAA00240.1) | 185Y<br>226Y<br>428Y | MELLIHRSSAIFLTLAVNALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGMAVSK<br>VLHLEGEVNKIKNALLSTNKAVVSLSNG**Y**SVLTSKVLDLKNYINNRLLPIVN<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITTIIIVIIVVLLSLIAIGLLLYCKAKNTPVTLSKDQLSGINNIAF*<br>*SK* |
| 60 | RSV B: (AHJ60043.1) | 185Y<br>226Y<br>428Y | MELLIHRSSAIFLTLAINALYLTSSQNITEEFYQSTCSAVSRGYFSALRTGW<br>YTSVITIELSNITETKCNGTDTKVKLIKQELDKYKNAVTELQLLMQNTPAAN<br>NRARREAPQHMNYTINTTKNLNVSISKKRKRRFLGFLLGVGSAIASGIAVSK<br>VLHLEGEVNKIKNALLSTNKAVVSLSNG**Y**SVLTSKVLDLKNYINNQLLPIVN<br>QQSCRIFNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRKSDELL*HNVNTGK*<br>*STTNIMITTIIIVIIVVLLSLIAIGLLLYCKAKNTPVTLSKDQLSGINNIAF*<br>*SK* |
| 61 | RSV A: A2 (138251) | 185Y<br>226Y<br>428Y<br>190F<br>207L | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPPTN<br>NRARRELPRFMNYTLNNAKKTNVTLSKKRKRRFLGFLLGVGSAIASGVAVSK<br>VLHLEGEVNKIKSALLSTNKAVVSLSNG**Y**SVLT**F**KVLDLKNYIDKQLLPI**L**N<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEINLCNVDIFNPKYDCKIMTSKTDVSSSVITSLGAIVSC<br>YGKTKCTASNK**Y**RGIIKTFSNGCDYVSNKGMDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSKDQLSGINNIAF*<br>*SN* |
| 62 | RSV A: *Homo sapiens*/USA/ LA2_55/2013 (AHX57020.1) | 185Y<br>226Y<br>428Y<br>190F<br>207L | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>SRARRELPRFMNYTLNNTKNTNVTLSKKRKRRFLGFLLGVGSAIASGIAVSK<br>VLHLEGEVNKIKSALLSTNKAVVSLSNG**Y**SVLT**F**KVLDLKNYIDKQLLPI**L**N<br>KQSCSISNIETVIEFQQ**Y**NNRLLEITREFSVNAGVTTPVSTYMLTNSELLSL<br>INDMPITNDQKKLMSSNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLALIAVGLLLYCKARSTPVILSKDQLSGINNIAF*<br>*SN* |
| 63 | RSV A: A/WI/629- | 185Y<br>226Y | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN |

TABLE 1-continued

Exemplary Amino Acid Sequences

| SEQ ID | Background Sequence | Introduced Mutations | Amino Acid Sequence |
|---|---|---|---|
| | 4071/98<br>(AEQ63520) | 428Y<br>190F<br>207L | NRARRELPRFMNYTLNNTKNTNVTVSKKRKRRFLGFLLGVGSAIASGIAVSK<br>VLHLEGEVNKIKSALLSTNKAVVSLSNG**Y**SVLT**F**KVLDLKNYIDKQLLPI**L**N<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSKDQLSGINNIAF*<br>*SN* |
| 64 | RSV A: TX-79223<br>(AGG39418) | 185Y<br>226Y<br>428Y<br>190F<br>207L | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKTTNVTLSKKRKRRFLGFLLGVGSAIASGIAVSK<br>VLHLEGEVNKIKSALLSTNKAVVSLSNG**Y**SVLT**F**KVLDLKNYIDKQLLPI**L**N<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNTDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSKDQLSGINNIAF*<br>*SS* |
| 65 | RSV A:<br>BE08-5146<br>(AFM55563) | 185Y<br>226Y<br>428Y<br>190F<br>207L | MELPILKTNAITTILAAVTLCFASSQNITEEFYQSTCSAVSKGYLSALRTGW<br>YTSVITIELSNIKENKCNGTDAKVKLIKQELDKYKNAVTELQLLMQSTQAAN<br>SRARRELPRFMNYTLNNTKNTNVTLSKKRKRRFLGFLLGVGSAIASGIAVSK<br>VLHLEGEVNKIKSALLSTNKAVVSLSNG**Y**SVLT**F**KVLDLKNYIDKQLLPI**L**N<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSKDQLSGINNIAF*<br>*SN* |
| 66 | RSV A:<br>Tracy<br>(AGG39397) | 185Y<br>226Y<br>428Y<br>190F<br>207L | MELLVHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTNNLNVSISKKRKRRFLGFLLGVGSAIASGIAVSK<br>VLHLEGEVNKIKNALLSTNKAVVSLSNG**Y**SVLT**F**KVLDLKNYINNQLLPI**L**N<br>QQSCRISNIETVIEFQQ**Y**NSRLLEIAREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 67 | RSV A:<br>RSV-4<br>(AEO45850) | 185Y<br>226Y<br>428Y<br>190F<br>207L | MELPILKTNAITTILTAVTFCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNNNVTLSKKRKRRFLGFLLGVGSAIASGIAVSK<br>VLHLEGEVNKIKSALLSTNKAVVSLSNG**Y**SVLT**F**KVLDLKNYIDKQLLPI**L**N<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNVGK*<br>*STTNIMITTIIIVIIVILLLLIAVGLLLYCKARSTPVTLSKDQLSGINNIAF*<br>*SN* |
| 68 | RSV A: 06-000827<br>(AFM55442) | 185Y<br>226Y<br>428Y<br>190F<br>207L | MELPILKTNAITTIFAAVTLCFASSQNITEEFYQSTCSAVSKGYLSALRTGW<br>YTSVITIELSNIKENKCNGTDAKVKLIKQELDKYKNAVTELQLLMQSTPAAN<br>NRARRELPRFMNYTLNNTKNNNVTLSKKRKRRFLGFLLGVGSAIASGIAVSK<br>VLHLEGEVNKIKSALLSTNKAVVSLSNG**Y**SVLT**F**KVLDLKNYIDKQLLPI**L**N<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNVGK*<br>*STTNIMITTIIIVIIVILLLLIAVGLFLYCKARSTPVTLSKEQLSGINNIAF*<br>*SN* |

TABLE 1-continued

| Exemplary Amino Acid Sequences | | | |
|---|---|---|---|
| SEQ ID | Background Sequence | Introduced Mutations | Amino Acid Sequence |
| 69 | RSV A: RSVA/*Homo sapiens*/ USA/901- 226A- 01/1990 (AHY21463) | 185Y<br>226Y<br>428Y<br>190F<br>207L | MELPILKTNAITTIFAAVTLCFASSQNITEEFYQSTCSAVSKGYLSALRTGW<br>YTSVITVELSNIKENKCNGTDAKVKLIKQELDKYKNAVTELQLLMQSTPAAN<br>NRARRELPRFMNYTLNNTKNTNVTLSKKRKRRFLGFLLGVGSAIASGIAVSK<br>VLHLEGEVNKIKSALLSTNKAVVSLSNG**Y**SVLT**F**KVLDLKNYIDKQLLPI**L**N<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNIDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*HNVNAGK*<br>*STTNIMITTIIIVIIVILLSLIAVGLLLYCKARSTPVTLSKDQLSGINNIAF*<br>*SN* |
| 70 | RSV A: RSV/A2 5W23_A | 185Y<br>226Y<br>428Y<br>190F<br>207L | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVSK<br>VLHLEGEVNKIKSALLSTNKAVVSLSNG**Y**SVLT**F**KVLDLKNYIDKQLLPI**L**N<br>KQSCSISNIETVIEFQQ**Y**NNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVFPSDEFDASISQVNEKINQSLAFIRKSDELL*SAIGGYI*<br>*PEAPRDGQAYVRKDGEWVLLSTFLGGLVPRGSHHHHHHSAWSHPQFEK* |
| 71 | RSV B: 18537 (138250) | 185Y<br>226Y<br>428Y<br>190F<br>207L | MELLIHRSSAIFLTLAVNALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNG**Y**SVLT**F**KVLDLKNYINNRLLPI**L**N<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITTIIIVIIVVLLSLIAIGLLLYCKAKNTPVTLSKDQLSGINNIAF*<br>*SK* |
| 72 | RSV B: RSVB/*Homo sapiens*/PER/ FPP00592/ 2011 (AHV80758) | 185Y<br>226Y<br>428Y<br>190F<br>207L | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNG**Y**SVLT**F**KVLDLKNYINNQLLPI**L**N<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 73 | RSV B: NH1144 (AFD34260) | 185Y<br>226Y<br>428Y<br>190F<br>207L | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNG**Y**SVLT**F**KVLDLKNYINNQLLPI**L**N<br>KQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDVSSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*S* |
| 74 | RSV B: TX- 79247 (AGG39514) | 185Y<br>226Y<br>428Y | MELLIHRSSAIFLTLAINALYLTSSQNITEEFYQSTCSAVSRGYLSALRTGW<br>YTSVITIELSNIKETKCNGTDTKVKLIKQELDKYKNAVTELQLLMQNTPVAN<br>NRARREAPQYMNYTINTTKNLNVSISKKRKRRFLGFLLGVGSAIASGIAVSK<br>VLHLEGEVNKIKNALLSTNKAVVSLSNG**Y**SVLT**F**KVLDLKNYINNQLLPI**L**N<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNTKEGSNICLTRTDRGWYCDNAGSVSFFPQADTCKVQSNR<br>VFCDTMYSLTLPSEVSLCNTDIFNSKYDCKIMTSKTDISSSVITSLGAIVSC |

TABLE 1-continued

| Exemplary Amino Acid Sequences | | | |
|---|---|---|---|
| SEQ ID | Background Sequence | Introduced Mutations | Amino Acid Sequence |
| | | | YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 75 | RSV B: CH-<br>18537<br>(AGG39487) | 185Y<br>226Y<br>428Y<br>190F<br>207L | MELLIHRSSAIFLTLAVNALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGMAVSK<br>VLHLEGEVNKIKNALLSTNKAVVSLSNG**Y**SVLT**F**KVLDLKNYINNRLLPI**L**N<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITTIIIVIIVVLLSLIAIGLLLYCKAKNTPVTLSKDQLSGINNIAF*<br>*SK* |
| 76 | RSV B:<br>NH1125<br>(AF125251) | 185Y<br>226Y<br>428Y<br>190F<br>207L | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNG**Y**SVLT**F**KVLDLKNYINNQLLPI**L**N<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 77 | RSV B: TX-<br>79222<br>(AGG39523) | 185Y<br>226Y<br>428Y | MELLIHRSSAIFLTLAINALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGIAVSK<br>VLHLEGEVNKIKNALLSTNKAVVSLSNG**Y**SVLT**F**KVLDLKNYINNQLLPI**L**N<br>KQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDVSSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*S* |
| 78 | RSV B: TX-<br>60567<br>(AGG39502) | 185Y<br>226Y<br>428Y<br>190F<br>207L | MELLIHRSSAIFLTLAINALYLTSSQNITEEFYQSTCSAVSRGYLSALRTGW<br>YTSVITIELSNIKETKCNGTDTKVKLIKQELDKYKNAVTELQLLMQNTPVAN<br>NRARREAPQYMNYTINTTKNLNVSISKKRKRRFLGFLLGVGSAIASGIAVSK<br>VLHLEGEVNKIKNALLSTNKAVVSLSNG**Y**SVLT**F**KVLDLKNYINNQLLPI**L**N<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNTKEGSNICLTRTDRGWYCDNAGSVSFFPQADTCKVQSNR<br>VFCDTMYSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITAIIIVIIVVLLSLIAIGLLLYCKAKNTPVTLSKDQLSGINNIAF*<br>*SK* |
| 79 | RSV B:<br>138250<br>(BAA00240.1) | 185Y<br>226Y<br>428Y<br>190F<br>207L | MELLIHRSSAIFLTLAVNALYLTSSQNITEEFYQSTCSAVSRGYFSALRTGW<br>YTSVITIELSNIKETKCNGTDTKVKLIKQELDKYKNAVTELQLLMQNTPAAN<br>NRARREAPQYMNYTINTTKNLNVSISKKRKRRFLGFLLGVGSAIASGMAVSK<br>VLHLEGEVNKIKNALLSTNKAVVSLSNG**Y**SVLT**F**KVLDLKNYINNRLLPI**L**N<br>QQSCRISNIETVIEFQQ**Y**NSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRRSDELL*HNVNTGK*<br>*STTNIMITTIIIVIIVVLLSLIAIGLLLYCKAKNTPVTLSKDQLSGINNIAF*<br>*SK* |
| 80 | RSV B:<br>(AHJ60043.1) | 185Y<br>226Y<br>428Y<br>190F<br>207L | MELLIHRSSAIFLTLAINALYLTSSQNITEEFYQSTCSAVSRGYFSALRTGW<br>YTSVITIELSNITETKCNGTDTKVKLIKQELDKYKNAVTELQLLMQNTPAAN<br>NRARREAPQHMNYTINTTKNLNVSISKKRKRRFLGFLLGVGSAIASGIAVSK<br>VLHLEGEVNKIKNALLSTNKAVVSLSNG**Y**SVLT**F**KVLDLKNYINNQLLPI**L**N<br>QQSCRIFNIETVIEFQQ**Y**NSRLLEITREFSVNAGVTTPLSTYMLTNSELLSL |

TABLE 1-continued

| Exemplary Amino Acid Sequences | | | |
|---|---|---|---|
| SEQ ID | Background Sequence | Introduced Mutations | Amino Acid Sequence |
| | | | INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNK**Y**RGIIKTFSNGCDYVSNKGVDTVSVGNTLYYVNKLEGKNLY<br>VKGEPIINYYDPLVFPSDEFDASISQVNEKINQSLAFIRKSDELL*HNVNTGK*<br>*STTNIMITTIIIVIIVVLLSLIAIGLLLYCKAKNTPVTLSKDQLSGINNIAF*<br>*SK* |
| 81 | AVR02 | 185Y<br>226Y<br>428Y<br>190F<br>207L | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVSK<br>VLHLEGEVNKIKSALLSTNKAVVSLSNG**Y**SVLTFKVLDLKNYIDKQLLPILN<br>KQSCSISNIETVIEFQQYNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNK**Y**RGIIKTFSNGCDYVSNKGVDTVSVGNTLYYVNKQEGKSLY<br>VKGEPIINFYDPLVEPSDEFDASISQVNEKINQSLAFIRKSDEVV*SAIGGFI*<br>*PEAPRDGQAYVRKDGEWVLLSTFLGGLVPRGSHHHHHHSAWSHPQFEK* |
| 82 | RSV A soluble | | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVEPSDEFDASISQVNEKINQSLAFIRKSDELL*SAIGGYI*<br>*PEAPRDGQAYVRKDGEWVLLSTFLGGLVPRGSHHHHHHSAWSHPQFEK* |
| 83 | RSV A full length (AHL84194) | (None) WT | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVSK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVEPSDEFDASISQVNEKINQSLAFIRKSDELL*HNVNTGK*<br>*STTNIMITTIIIVIIVVLLSLIAIGLLLYCKAKNTPVTLSKDQLSGINNIAF*<br>*SK* |
| 84 | RSV B soluble | | MELLIHRSSAIFLTLAINALYLTSSQNITEEFYQSTCSAVSRGYFSALRTGW<br>YTSVITIELSNITETKCNGTDTKVKLIKQELDKYKNAVTELQLLMQNTPAAN<br>NRARREAPQHMNYTINTTKNLNVSISKKRKRRFLGFLLGVGSAIASGIAVSK<br>VLHLEGEVNKIKNALLSTNKAVVSLSNGVSVLTSKVLDLKNYINNQLLPIVN<br>QQ<br>SCRIFNIETVIEFQQKNSRLLEITREFSVNAGVTTPLSTYMLTNSELLSLIN<br>DMPITNDQKKLMSSNVQIVRQQSYSIMSIIKEEVLAYVVQLPIYGVIDTPCW<br>KLHTSPLCTTNIKEGSNICLTRTDRGWYCDNAGSVSFFPQADTCKVQSNRVF<br>CDTMNSLTLPSEVSLCNTDIFNSKYDCKIMTSKTDISSSVITSLGAIVSCYG<br>KTKCTASNKNRGIIKTFSNGCDYVSNKGVDTVSVGNTLYYVNKLEGKNLYVK<br>GEPIINYYDPLVFPSDEFDASISQVNEKINQSLAFIRKSDELL*SAIGGYIPE*<br>*APRDGQAYVRKDGEWVLLSTFLGGLVPRGSHHHHHHSAWSHPQFEK* |
| 85 | RSV B full length (AHJ60043.1) | (None) WT | MELLIHRSSAIFLTLAINALYLTSSQNITEEFYQSTCSAVSRGYFSALRTGW<br>YTSVITIELSNITETKCNGTDTKVKLIKQELDKYKNAVTELQLLMQNTPAAN<br>NRARREAPQHMNYTINTTKNLNVSISKKRKRRFLGFLLGVGSAIASGIAVSK<br>VLHLEGEVNKIKNALLSTNKAVVSLSNGVSVLTSKVLDLKNYINNQLLPIVN<br>QQSCRIFNIETVIEFQQKNSRLLEITREFSVNAGVTTPLSTYMLTNSELLSL<br>INDMPITNDQKKLMSSNVQIVRQQSYSIMSIIKEEVLAYVVQLPIYGVIDTP<br>CWKLHTSPLCTTNIKEGSNICLTRTDRGWYCDNAGSVSFFPQADTCKVQSNR<br>VFCDTMNSLTLPSEVSLCNTDIFNSKYDCKIMTSKTDISSSVITSLGAIVSC<br>YGKTKCTASNKNRGIIKTFSNGCDYVSNKGVDTVSVGNTLYYVNKLEGKNLY<br>VKGEPIINYYDPLVFPSDEFDASISQVNEKINQSLAFIRKSDELL*HNVNTGK*<br>*STTNIMITTIIIVIIVVLLSLIAIGLLLYCKAKNTPVTLSKDQLSGINNIAF*<br>*SK* |
| 86 | DSCav1 soluble | DS Cav1 | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVCK<br>VLHLEGEVNKIKSALLSTNKAVVSLSNGVSVLTFKVLDLKNYIDKQLLPILN |

TABLE 1-continued

Exemplary Amino Acid Sequences

| SEQ ID | Background Sequence | Introduced Mutations | Amino Acid Sequence |
| --- | --- | --- | --- |
| | | | KQSCSISNIETVIEFQQKNNRLLEITREFSVNAGVTTPVSTYMLTNSELLSL<br>INDMPITNDQKKLMSNNVQIVRQQSYSIMCIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*SAIGGYI*<br>*PEAPRDGQAYVRKDGEWVLLSTFLGGLVPRGSHHHHHHSAWSHPQFEK* |
| 87 | DSCav1 full length | DS Cav1 | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVCK<br>VLHLEGEVNKIKSALLSTNKAVVSLSNGVSVLTFKVLDLKNYIDKQLLPILN<br>KQSCSISNIETVIEFQQKNNRLLEITREFSVNAGVTTPVSTYMLTNSELLSL<br>INDMPITNDQKKLMSNNVQIVRQQSYSIMCIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNTGK*<br>*STTNIMITTIIIVIIVVLLSLIAIGLLLYCKAKNTPVTLSKDQLSGINNIAF*<br>*SK* |
| 88 | Cav1 soluble | Cav1 | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVSK<br>VLHLEGEVNKIKSALLSTNKAVVSLSNGVSVLTFKVLDLKNYIDKQLLPILN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*SAIGGYI*<br>*PEAPRDGQAYVRKDGEWVLLSTFLGGLVPRGSHHHHHHSAWSHPQFEK* |
| 89 | Cav1 full length | Cav1 | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVSK<br>VLHLEGEVNKIKSALLSTNKAVVSLSNGVSVLTFKVLDLKNYIDKQLLPILN<br>KQSCSISNIETVIEFQQKNNRLLEITREFSVNAGVTTPVSTYMLTNSELLSL<br>INDMPITNDQKKLMSNNVQIVRQQSYSIMSIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNTGK*<br>*STTNIMITTIIIVIIVVLLSLIAIGLLLYCKAKNTPVTLSKDQLSGINNIAF*<br>*SK* |
| 90 | DS soluble | DS | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVCK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMCIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*SAIGGYI*<br>*PEAPRDGQAYVRKDGEWVLLSTFLGGLVPRGSHHHHHHSAWSHPQFEK* |
| 91 | DS full length | DS | MELLILKANAITTILTAVTFCFASGQNITEEFYQSTCSAVSKGYLSALRTGW<br>YTSVITIELSNIKENKCNGTDAKVKLIKQELDKYKNAVTELQLLMQSTPATN<br>NRARRELPRFMNYTLNNAKKTNVTLSKKRKRRFLGFLLGVGSAIASGVAVCK<br>VLHLEGEVNKIKSALLSTNKAVVSLSNGVSVLTSKVLDLKNYIDKQLLPIVN<br>KQSCSISNIETVIEFQQKNNRLLEITREFSVNAGVTTPVSTYMLTNSELLSL<br>INDMPITNDQKKLMSNNVQIVRQQSYSIMCIIKEEVLAYVVQLPLYGVIDTP<br>CWKLHTSPLCTTNTKEGSNICLTRTDRGWYCDNAGSVSFFPQAETCKVQSNR<br>VFCDTMNSLTLPSEVNLCNVDIFNPKYDCKIMTSKTDVSSSVITSLGAIVSC<br>YGKTKCTASNKNRGIIKTFSNGCDYVSNKGVDTVSVGNTLYYVNKQEGKSLY<br>VKGEPIINFYDPLVFPSDEFDASISQVNEKINQSLAFIRKSDELL*HNVNTGK*<br>*STTNIMITTIIIVIIVVLLSLIAIGLLLYCRAKNTPVTLSKDQLSGINNIAF*<br>*SK* |

TABLE 1-continued

| Exemplary Amino Acid Sequences | | | |
|---|---|---|---|
| SEQ ID | Background Sequence | Introduced Mutations | Amino Acid Sequence |
| 92 | Foldon domain plus thrombin cleavge site and tags and linkers. | N/A | SAIGGYIPEAPRDGQAYVRKDGEWVLLSTFLGGLVPRGSHHHHHHSAWSHPQFEK |
| 93 | Foldon domain | N/A | GYIPEAPRDGQAYVRKDGEWVLLSTFL |
| 94 | Thrombin Cleavage site | | LVPRGS |
| 95 | His Tag | N/A | HHHHHH |
| 96 | Strep II Tag | N/A | WSHPQFEK |

In Table 1 SEQ ID NOs 1-91 are exemplary WT and mutant RSV F amino acid sequences and SEQ ID Nos 92-96 are exemplary artificial sequences that can be introduced at the C-terminal of an RSV F molecule. For SEQ ID NOs 1-91 underlined residues are F1 and F2 polypeptides, residues in bold font are introduced mutations, residues in italics are residues that may be removed or replaced in some embodiments, and double-underlined residues are artificially introduced C-terminal sequences.

TABLE 2

| Summary of Exemplary RSV F Amino Acid Sequences | |
|---|---|
| SEQ ID NOs. | RSV F Molecules/Sequences |
| 1-20<br>82-91 | "Background" Sequences |
| 1-20<br>82-85 | WT "Background" Sequences |
| 1-10<br>82-83 | WT RSV A "Background" Sequences |
| 11-20<br>84-85 | WT RSV B "Background" Sequences |
| 21-81 | 428Y Mutants |
| 41-81 | 185Y, 226Y, 428Y Mutants |
| 61-81 | 185Y, 226Y, 428Y, 190F, 207L Mutants |

Various embodiments of the present invention may also be further described by the following non-limiting examples:

Example 1

Selected Materials & Methods

Mutant RSV F proteins were expressed in human cells and modified by the introduction of di-tyrosine bonds as described below.

cDNA encoding mutant RSV F molecules was cloned into the pCDNA3.1/zeo+ expression vector (Invitrogen) via 5' BamHI and 3'Xhol restriction endonuclease sites using standard methods (See FIG. 1).

HEK 293 cells (ATCC) were grown in Dulbecco's Modification of Eagle's Medium (DMEM, Invitrogen) supplemented with 10% Fetal Bovine Serum and 50 μg/ml gentamycin. Cells were seeded into 6-well tissue culture plates (Corning) and grown till 80% confluent (~24h). Cells were transfected with 2 μg (micrograms) of each RSV F expression plasmid per well using a 1:4 ratio (M/V) of DNA to polyethylenimine (25 kDa, linear). 16 h post-transfection, media was removed and replaced with 2 ml/well of serum-free Freestyle-293 expression media (Invitrogen). Cells were cultured at 37 degrees C. for an additional 48 h-72 h in 5% $CO_2$ prior to collection and analysis.

Detection of RSV-F in Cell Supernatants by ELISA. After collection, total RSV F protein was directly captured from cell supernatants for 1 h at room temperature in EIA/RIA high-bind 96-well plates (Corning). Protein-containing and control wells were subsequently blocked with 4% nonfat milk in PBS-tween20 (0.05%) for 1 h at room temperature. Plates were washed 3X with PBS-T (400 μl/well). Total RSV F was detected for 1 h using a high-affinity human anti-hRSV antibody (100 ng/ml in PBS) that recognizes both pre- and post-fusion forms of RSV F. Prefusion F was detected using a pre-F specific human monoclonal antibody (2 μg/ml in PBS) that recognizes site ø. Wells were again washed 3X in PBS-T followed by a 1 h room temperature incubation with an HRP-conjugated goat anti-human F(ab)2 (Jackson Immunoresearch) at a 1:5000 dilution in PBS. Wells were washed 6X with PBS-T and total RSV-F was detected and quantified using 100 μl 3,3',5,5'-tetramethylbenzidine (TMB) to produce a colorimetric signal. The colorimetric reaction was stopped by the addition of equal volume 4N sulfuric acid. Final Optical Density readings were taking at 450 nm using a BioRad Benchmark Plus microplate absorbance spectrophotometer. A 2X serial dilution series for each supernatant was used to determine the linear range of detectable signal for each sample allowing accurate comparison of the relative amount of RSV-F between samples.

Di-tyrosine Cross-linking in Cell Supernatants. Immediately following collection, 100 μl of transfected and control cell supernatants were transferred to wells of black, flat-bottom, non-binding 96-well FIA plates (Greiner bio-one). 300 ng of *Arthromyces ramosus* peroxidase was added to each sample to be cross-linked. 1 μl of 1.2 mM $H_2O_2$ was then added to both control and DT reactions for a final reaction concentration of 120 μM $H_2O_2$. Reactions were allowed to proceed for 20 minutes at room temperature followed by alkalization of the reactions by addition of an equal volume of sodium phosphate buffer at pH 10. Di-tyrosine specific fluorescence was read at an excitation wavelength of 320 nm and emission wavelength of 405 nm using a Thermo Scientific Fluoroskan Ascent FL.

72 h post transfection, supernatants were cross-linked (DT) or left uncross-linked and total protein was measured by ELISA using a high-affinity human anti-hRSV antibody (100 ng/ml in PBS) that recognizes both pre- and post-fusion forms of RSV-F. In some experiments, following storage at 4 degrees C. for 16 days, presentation of site ø was measured by ELISA using a preF specific human monoclonal antibody (2 μg/ml in PBS) that recognizes site ø.

Example 2

Figure 2:
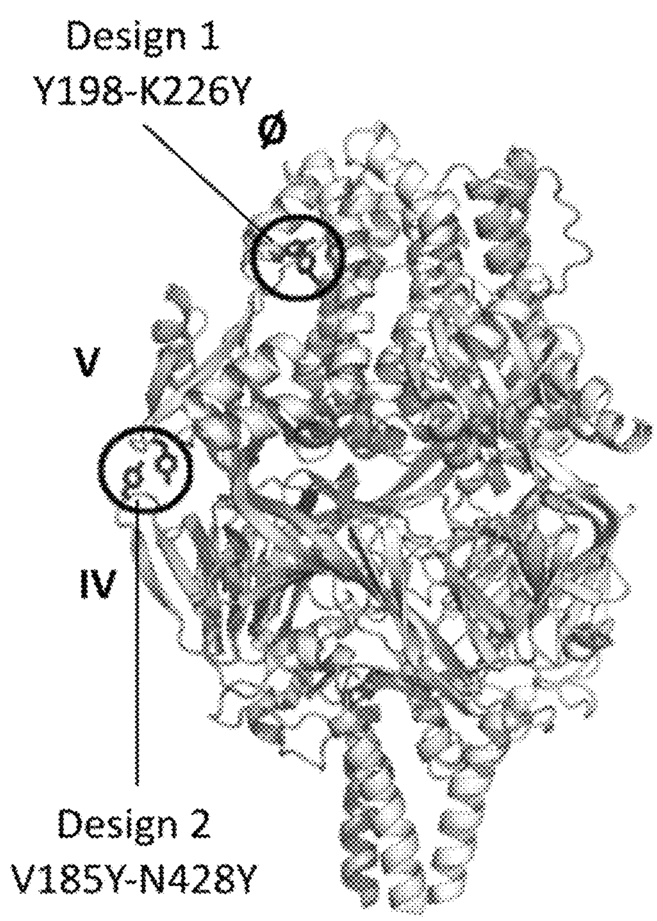
FIG. 2. Schematic representation of a mutant RSV F molecule comprising a 198Y-226Y DT cross link ("Design 1") and a 185Y-428Y DT cross link (Design 2). Antigenic sites Ø, IV, and V are indicated in relation to the structure of the molecule.

Production & In Vitro Characterization of a 428Y, 185Y, 226Y Mutant RSV F Molecule FIG. 2 provides a schematic representation of an exemplary mutant RSV F molecule comprising three-to-tyrosine mutations—a 428Y mutations, a 185Y mutation, and a 226Y mutation. This exemplary mutant RSV F molecule is referred to as "AVR02." The F0 precursor form of AVR02 has the amino acid sequence of SEQ ID NO. 81. The mature AVR02 molecule (formed after transfection and expression in cells of a nucleic acid molecule that encodes SEQ ID NO. 81) comprises amino acid residues 26-109 and 137-568 of SEQ ID No. 81—where amino acid residues 26-109 are RSV F F2 residues, amino acid residues 137-513 are RSV F F1 residues, and amino acid residues 514-568 are heterologous sequences and includes a foldon domain, a His tag, a StrepII tag, and a thrombin cleavage site. The signal peptides from amino acids 1-25 and the pep27 peptide from amino acids 100-136 are not present in the final mature trimeric AVR02 molecule.

Figure 4:
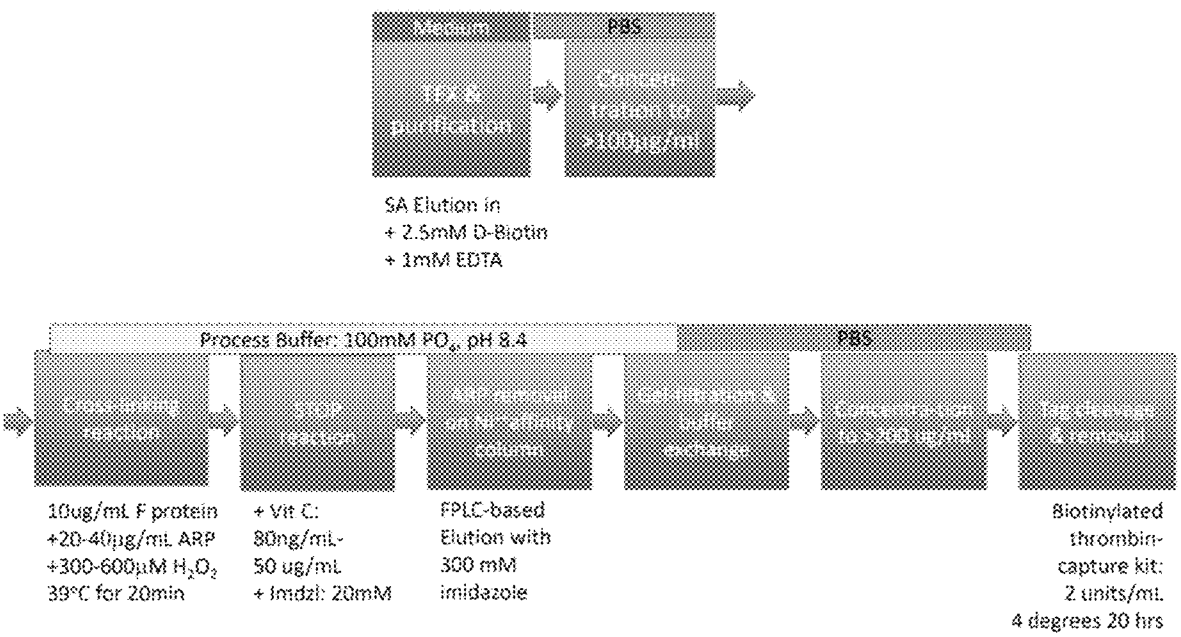
FIG. 4. A schematic of an exemplary protocol for production of DT-cross-linked AVR02.

FIG. 4 provides a schematic representation of a method of production of DT cross-linked AVR02 (referred to as "DT-AVR02"). Non-crosslinked AVR02 is transiently transfected into 293 Freestyle cells (Invitrogen), by standard methods using PEI and is expressed as a secreted/soluble form for 5 days. On day 5, cells are harvested and pelleted by a low speed centrifugation spin in a swinging bucket rotor (1000×g×10 min), decanted into a second tube and spun at a higher speed to clarify (3000×g×15 min), transferred again and passed through a 70 uM cell strainer prior to purification. AVR02 is purified using Streptactin resin (IBA Lifesciences) according to the manufacturer's instructions. AVR02 is eluted using a PBS-based elution buffer containing 1 mM EDTA and 2.5 mM Desthiobiotin, and concentrated using tangential flow filtration (Pall Corporation) and clarified by a final centrifugation step (>20,000×g×5 min at 4 degrees).

The crosslinking reaction is carried out in a phosphate containing buffer including 150 mM NaCl using the peroxidase enzyme from *arthromyces ramosus* at 20-40 μg/mL and AVR02 at a concentration of 10-20 μg/mL. The reaction is initiated by the addition of 300-600 μM $H_2O_2$ at 39 degrees Celsius for 20 minutes and quenched by the addition of ascorbic acid (80 ng/mL-50 μg/mL) and imidazole is added at this time to 20 mM. The AVR02 protein is then purified using FPLC over IMAC chromatography columns (Ni-NTA) in order to eliminate the peroxidase, followed by size exclusion chromatography (Superdex 200 pg) using PBS as the eluent. Fractions containing A VR02 are then pooled, concentrated to 500 μg/mL and cleaved using 2 units/mL Biotinylated thrombin (Millipore) overnight at 4 degrees Celsius (20 hrs). The thrombin is then eliminated according to the manufacturer's instructions, and any uncleaved AVR02 protein is eliminated by a 30 minute incubation with Streptactin beads at RT in a batch format. The protein is then passed through a spin filter in order to eliminate the beads and spun a final time at 4 degrees Celsius prior to final assay for protein quantification. Final protein assay is a ninhydrin-based protein assay according to the method of Starcher, B. (Analytical Biochemistry 292:125-129 (2001). The protein is flash frozen in liquid $N_2$ and stored at −80 degrees Celsius prior to use.

Figure 3:
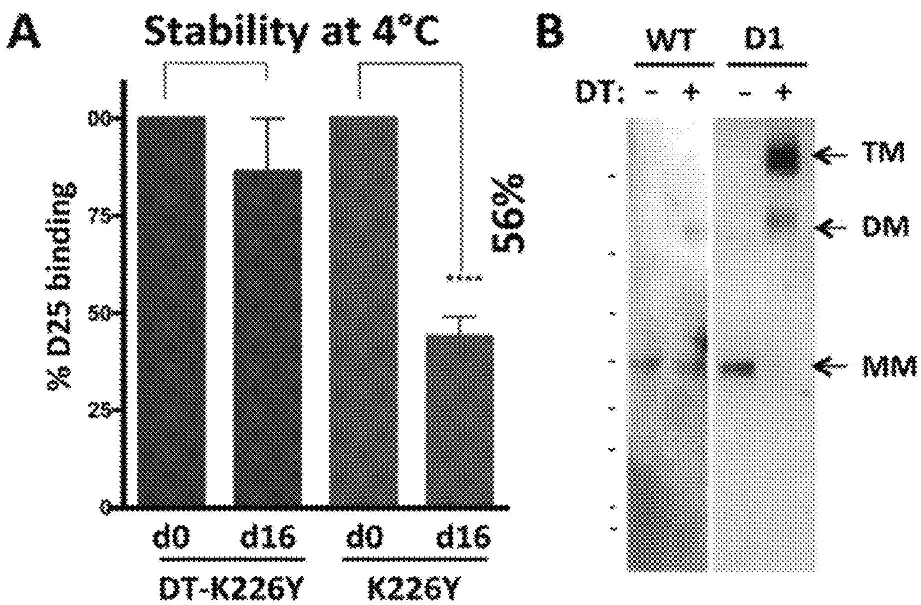
FIGS. 3A-B.

FIG. 3 provides data showing that each of the two "designs" incorporated into AVR02 form dityrosine bonds. FIG. 3A—After applying the crosslinking reaction, stability introduced by the intramolecular crosslink between 198Y and 226Y (Design 1) was measured at 4° C. over 2 weeks by ELISA using D25, a prefusion-specific mAb that binds site Ø. FIG. 3B—The intermolecular DT bond formation between 185Y and 428Y (Design 2) was assayed by Western blotting, by comparison to WT (Motavizumab is primary Ab). The $F_1$ protein shifts to the size of a trimer (TM).

FIGS. 5A-B provides data showing the conformational integrity of AVR02 and DT-cross-linked AVR02 as compared to the RSV mutant referred to as DS-Cav1 (which is described in McLellan et al. (2013) Science 342:592-598, and which comprises S155C, S290C, S190F, and V207L mutations) as determined based on binding of a site IV/V antibody (FIG. 5A) and a site Ø antibody (FIG. 5B).

FIGS. 6A-B provides data showing the temperature stability of DT-AVR02. FIG. 6C provides data showing that AVR02 exhibited no loss in binding to the a Ø specific mAb (5C4) after storage for 5 weeks at 4° C.

Example 3

In Vivo Testing of a 428Y, 185Y, 226Y Mutant RSV F Molecule in Mice

Studies were performed to test the immunogenicity of DT cross-linked AVR02 (DT-AVR02) as compared to DS-Cav1. The details of the AVR02 and DT-AVR02 molecules are described above. The DS-Cav1 mutant is described in Mclellan et al. (2013) Science 342:592-598, and comprises S155C, S290C, S190F, and V207L mutations. Two groups of 10, 6-8 week old, female, pathogen-free balb/c mice (Jackson Labs) were immunized by intramuscular injection in a prime (Day 0)—Boost (Day21) regimen: Group 1 with 10 μg (micrograms) of alum-adjuvanted DT-AVR02 per animal per dose, and Group 2 with 10 ug (micrograms) of alum-adjuvanted DS-Cav1 per animal per dose. Serum was drawn at time on day 35, two weeks after the second immunization (boost).

Heat inactivated serum was diluted to 1:800 in phenol-free MEM supplemented with glutamax, 5% FBS, and Penicillin/Streptomycin and serially diluted in a 4-fold series (50 uL final volume). RSV-Renilla Luciferase virus was then diluted in the same medium as above to $2\times10^4$ pfu/mL and 50 uL was added to each well (10,000 pfu/well) with virus only and Motavizumab controls. Virus and serum was incubated at 37 degrees Celsius, 5% $CO_2$, for 2 hrs. Hep-2 cells (ATCC) were then trypsinized, counted, and diluted to $1\times10^6$ cells/mL in the same medium and 25 μL was added to each well ($2.5\times10^4$ cells/well). The cells were then incubated at 37 degrees Celsius, 5% $CO_2$ for 60-72 hrs and luciferase activity was quantified using the Renilla-glo luciferase assay system (Promega) according to the manufacturer's instructions. Data was analyzed using nonlinear regression in order to calculate $IC_{50}$ concentrations of each serum dilution (Graphpad Prism).

Figure 7:
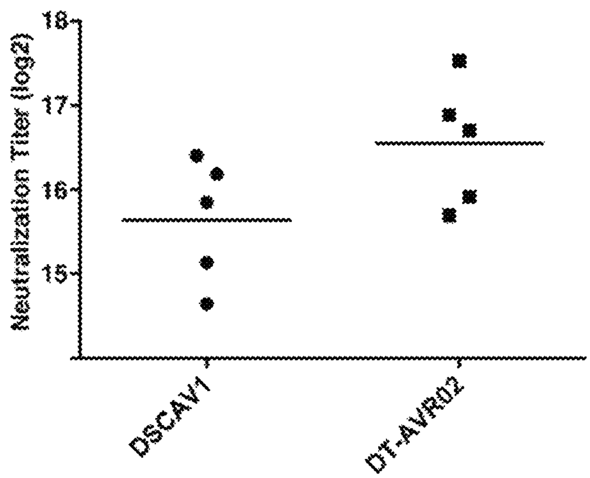
FIG. 7. Efficacy of a DT cross-linked 428Y RSV F mutant (DT-AVR02 or DT-preF) in vivo in mice. Neutralization titers. RSV-RenillaLuc neutralization titers from animals vaccinated with either DSCAV1 or DT-AVR02 on alum.

FIG. 7 provides the results of this study—showing the RSV-RenillaLuc neutralization titers from animals vaccinated with either DS-Cav1 or DT-AVR02 on alum.

Example 4

In Vivo Testing of a 428Y, 185Y, 226Y Mutant RSV F Molecule in Cotton Rats

As used in this Example, and the accompanying Figures, the term "DT-preF" refers to the molecule referred to in the previous examples "DT-AVR02," and the term DT-preF may be used interchangeably with the term DT-AVR02. Details of the structure of the DT-AVR02 molecule and its production are provided above.

Summary/Overview

The goal of this experiment was to evaluate the efficacy and safety of the DT-AVR02 for protection against RSV in cotton rats (CR). The effect of adding an adjuvant (2% Alhydrogel (ALH) at 4 mg/CR), was also was evaluated. A prime-boost strategy was used and vaccine was administered by intramuscular injection. On day +39 following RSV/A/Tracy challenge (day +35), lung lavage fluids from the two (2) of the larger lobes of the right lung and nasal wash fluids were obtained and RSV titers were determined by plaque assay. One (1) lobe of the right lung was flash-frozen in liquid $N_2$ and stored at −80° C. Serum samples were obtained throughout the experiment and used to measure neutralizing antibody activities against RSV/A/Tracy and RSV/B/18537.

Both 2 and 10 μg doses of DT-AVR02 protein/cotton rat were very effective in reducing RSV/A/Tracy in the lungs by approximately 4 $\log_{10}$ PFU/g lung and nose by approximately 1.5 $\log_{10}$ total PFU compared to the saline control. All of the vaccines generated a RSV/A/Tracy-specific neutralizing antibody response following a second (boost) vaccination in these naïve cotton rats and which was greater than that generated by live RSV/A/Tracy infection on day 0.

The DT-AVR02 (DT-preF) adjuvanted vaccines administered at either the 2 μg or 10 μg dose using a two-dose regimen, provided a robust immune response in RSV naïve cotton rats. Both the 2 μg and 10 μg dose provided excellent protection against RSV/A/Tracy replication in the lungs and a significant but moderate reduction in the nose and elicited RSV/A/Tracy-specific and RSV/B/18537-specific serum neutralizing antibodies. The data suggests that these vaccines should be particularly effective in RSV pre-immune populations, such as, for example, the elderly adult population.

Details of Experimental Design, Results & Conclusions

We designed and tested a series of RSV F mutants with tyrosine substitutions enabling the introduction of targeted dityrosine (DT) crosslinks to conformationally lock the RSV F protein in its prefusion conformation. One such molecule is referred to herein as DT-AVR02 (also referred to herein as DT-preF). The details of the structure and production of this molecule are described above in other Examples. Preliminary studies in mice (see prior Example) showed that DT-AVR02 is immunogenically at least equivalent to DS-Cav1, one of the two current "best-in-breed," partially-stabilized, preF designs (DS-Cav1 and SC-DM)—while having dramatically improved thermostability. Although DS-Cav1 and SC-DM have shown promise as preF antigens, the proteins are still relatively unstable and lose antigenicity after only a few weeks at 4° C. Our in vitro stability assays indicate that DT-AVR02 is more thermo-stable than DS-Cav1 and SC-DM, and that it retains preF antigenicity for at least 100 hours at 37° C. This indicates that DT-AVR02 is likely to be both sufficiently stable for clinical development and that its improved stability should also improve vaccine exposure and efficacy in vivo.

The goal of the experiments described in this Example was to evaluate the DT-AVR02/DT-preF RSV prefusion F protein vaccine in vivo in cotton rats at two doses (2 or 10 μg/CR). The effect of adding an adjuvant, 2% Alhydrogel (ALH), to the formulation was also evaluated. A prime-boost strategy was used, and vaccine was administered by intramuscular injections. On day +39 following RSV/A/Tracy challenge (day +35), lung lavage fluids from two (2) of the larger lobes of the right lung and nasal wash fluids were obtained and RSV titers determined by plaque assay. Serum samples were obtained throughout the experiment and used to measure neutralizing antibody activities against RSV/A/Tracy and RSV/B/18537.

Figure 8:
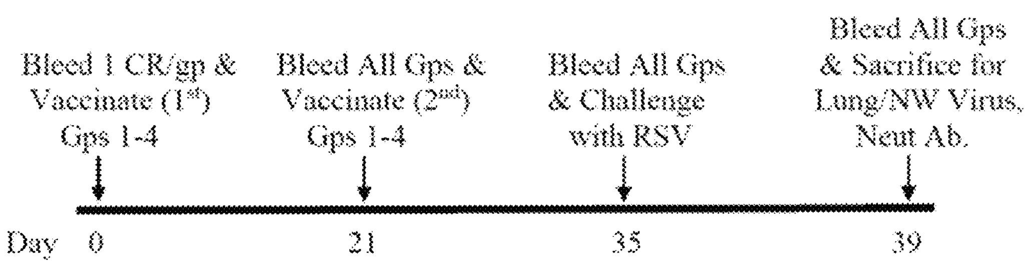
FIG. 8. A schematic of an exemplary vaccination schedule.

Vaccination (IM) was performed using the vaccination schedule illustrated in FIG. 8—in which vaccination was performed on day 0 with a boost at 21 days and virus challenge 14 days later.

All animals were challenged with live RSV/A/Tracy on Day +35. Group 1 had 5 cotton rats (CR) injected IM with Saline (as a positive virus infection control). Group 2 had 5 CR infected with live RSV/A/Tracy on Day 0 (the "gold standard"). Group 3 had 5 CR injected IM with 2 μg DT-preF and adjuvanted with 100 μg of 2% ALH/CR. Group 4-5 had CR injected IM with 10 μg DT-preF and adjuvanted with 100 μg of 2% ALH/CR.

The cotton rats used had body weights in the range ~75-150 g (as determined by age at start). Body weight was also determined at the end of the experiment. Animal body weight, age and sex distribution was similar across all groups at the start. Experiments were performed utilizing NIH and United States Department of Agriculture guidelines, The Public Health Service Policy on Humane Care and Use of Laboratory Animals, and experimental protocols were approved by an Investigational Animal Care and Use Committee (IACUC).

RSV/A/Tracy (RSV/A/Tracy) (P3 w.p. Mar. 13, 2015) at $1.21\times10^5$ PFU was administered intranasally (100 μL) to cotton rats lightly anesthetized with isoflurane. After inoculation on days 0 (group 2) and day 35 (all groups) virus inoculum was back-titered to confirm initial concentration ($\log_{10}$ $TCID_{50}$/mL).

Alhydrogel (Aluminium hydroxide gel; ALH) was stored at RT [21° C.]. DT-AVR02 stock protein concentration was 160 μg/mL in PBS (stored at −80° C.). All steps were performed under a sterile hood. An Alhydrogel 2% formulation was used at a dose of 100 μL per animal for 7 doses (700 μL total).

Protein samples were thawed on wet ice. For the 10 μg dose, protein was diluted to a concentration of 105.26 ug/mL in PBS (665 uL total, 437 μL DT-PreF, 228 μL PBS). For the 2 μg dose, protein was diluted to a concentration of 21.05 μg/mL in PBS (665 total, 87.4 μL DT-PreF, 577.6 μL PBS). Protein samples were inverted to mix. Alhydrogel (2%, Brenntag) was thoroughly mixed by inversion. The Alhydrogel bottle was opened and 35 μL was pipetted into each dose, mixing thoroughly by hand to make a homogeneous suspension. Before vaccination, formulated solutions were mixed several times and the mixing was repeated before every injection to ensure a homogeneous solution.

DT-AVR02 plus adjuvant (100 μL of DT-AVR02 plus ALH (groups 3, 4)) was injected (tuberculin syringe) into the area of the left tibialis anterior (TA) muscle (IM). The alternate leg was used for the second vaccination (day+21 boost). On day 0, blood was obtained from the orbital plexus of one cotton rat in each group. On all other indicated days, blood was obtained from all of the cotton rats (5 CR/group; 4 groups). Following euthanasia with $CO_2$, the right lung was tied off. Two lobes from the right lung were removed and rinsed in sterile water to remove external blood contamination and weighed. The same two right lobes were transpleurally lavaged using 3 mL of Iscove's media with 15% glycerin mixed with 2% FBS-MEM (1:1, v:v) in a 3 mL syringe with a 26G3/8 needle and injecting at multiple sites to totally inflate the lobe. Lavage fluid was recovered by gently pressing one inflated lobe flat and used to transpleurally lavage the other lobe following the same technique. The lavage fluid was collected and stored on ice until titered. For nasal washes of the upper respiratory tract, the jaws were disarticulated. The head was removed and 1 mL of Iscove's media with 15% glycerin mixed with 2% FBS-MEM (1:1, v:v) was pushed through each naris (total of 2 mL). The effluent was collected from the posterior opening of the pallet and stored on ice until titered. Samples were not frozen before titration, which occurred at the end of sample collection. An aliquot of the serum samples was saved for antibody analysis. RSV Tracy lung lavage titers (PFU/g lung) and nasal wash titers (total PFU) were determined as follows. Plaque assays were performed using 24-well tissue cultures plates containing nearly confluent monolayers (~2×$10^5$ cells/well) of HEp-2 cells prepared in 10% FBS 24 h prior to start of assay. At the start of each assay, dilutions (usually serial $log_{10}$) were made of the test samples. A 0.2 mL sample of each was then added to wells in duplicate and allowed to adsorb for 90 min with occasional gentle agitation. After the inoculum was removed, the monolayers were then overlayed with 0.75% methylcellulose in MEM containing antibiotics, vitamins and other nutrients. Tissue culture and positive virus controls were included in each assay. The plates were placed in a 36° C., 5% $CO_2$ incubator. On day 6 (+/−1 day), plates were stained with 0.01% crystal violet/10% formalin solution (~1.5 mL/well) and allowed to sit for 24-48 h at room temperature. Wells were rinsed with water. Plaques when present were easily visible (clear circles on a very dark blue background). All of the plaques in wells containing between ~20 and 100 plaques were enumerated, averaged and the virus titers calculated as total $log_{10}$ PFU for nasal wash fluid or $log_{10}$ PFU/g of tissue for lungs or other organs. The lower limit of detection by this method is 0.70 $log_{10}$ total PFU or approximately 1.4 $log_{10}$ PFU/g lung tissue, respectively.

Tests for anti-RSV neutralizing antibody on days 0, 21, 35, and 39 were performed as follows. Tests for serum neutralizing antibodies to RSV/A/Tracy and RSV/B/18537 were performed in 96-well microtiter plates with HEp-2 cells. The plaque purified RSV virus was used in a microneutralization (Nt) assay. Samples were heat inactivated at 56° C. for 30 min. Serial two-fold dilutions in duplicates starting at 3 $log_2$ were performed to determine the neutralizing antibody (Ab) titer for each sample. The neutralizing antibody titer was defined as the serum dilution at which ≥50% reduction in viral cytopathic effect (CPE) was observed. CPE was defined as tissue destruction and was determined visually after the wells were fixed with 10% neutral buffered formalin and stained with crystal violet. Neutralizing antibody (NtAb) titers were provided as categorical log numbers and not continuous values. The lowest detectable NtAb titer was 2.5 $log_2$. Samples with non-detectable Nt Ab titers were assigned a value of 2 $log_2$. Nt Ab titers were reported in multiples of 0.5 $log_2$ (e.g., 2.5, 3.0, 3.5, 4.0, etc.). If a sample had an NtAb titer that was equal to or exceeded the upper limit of the test (>14 $log_2$), that sample was retested so that the NtAb titer could be determined by extending the dilutions to 26 $log_2$. As an internal standard palivizumab was included at 40 μg/mL. RSV-specific antibody titers were determined by ELISA. Serum samples were stored at −20° C. prior to performing ELISA assays. Initially, viral load or RSV-specific neutralizing antibody levels between controls and vaccine groups was analyzed with $log_{10}$-transformed viral titers or with $log_2$-transformed antibody titers using Excel's Student t test, two-tailed (Microsoft Office 2013). Additional comparisons can be analyzed by ANOVA using InStat3 (GraphPad) with post-hoc Tukey comparisons.

Further details of the experimental design are shown in Table A. The results are summarized above. Further details of the results are provided below, including in Tables B-L.

TABLE A

| Group[1] | Vaccine[2] | Volume (mL) | F Protein (μg/CR) | Adjuvant Dose (mg/CR) | Schedule (days) | Challenge[3]/ Harvest | Endpoints |
|---|---|---|---|---|---|---|---|
| 1 | Saline | 0.100 | 0 | 0 | 0, +21 | Day | Virus titer in |
| 2 | Live RSV/ A/Tracy Day 0 | — | — | — | | +35/+39 | lung lavage and nasal wash fluids by PFU: |
| 3 | DT-preF + ALH | 0.100 | 2 | 0.1 | | | Serum Nt antibody levels: |
| 4 | DT-preF + ALH | 0.100 | 10 | 0.1 | | | |

Abbreviations: ALH, 2% Brenntag Alhydrogel; PFU, plaque forming units; Nt, neutralizing.

[1]N = 5 animals/group; 30 animals total.

[2]IM route of administration.

[3]All animals to be challenged i.n. (100 μL) with RSV/A/Tracy.

TABLE B

| Group Lung and Body Weights on Day +39 | | | |
|---|---|---|---|
| Group | Vaccine | Lung Lobe Weight Used (g)[1] Mean ± SD | Body Weight (g)[2] Mean ± SD |
| 1 | Saline | 0.24 ± 0.03 | 179.0 ± 14.9 |
| 2 | Live RSV/A/ Tracy Day 0 | 0.24 ± 0.04 | 186.7 ± 13.6 |
| 3 | DT-preF (2 μg) + ALH | 0.25 ± 0.05 | 171.4 ± 53.3 |
| 4 | DT-preF (10 μg) + ALH | 0.21 ± 0.07 | 185.7 ± 15.4 |

[1]There was no statistically significant difference between the groups (Student t test, two-tailed).
[2]There was no statistically significant difference between the groups (Student t test, two-tailed).

TABLE C

| RSV/A/Tracy Titers in Nasal Wash Fluids on Day +39 | | | | | | | | | | |
|---|---|---|---|---|---|---|---|---|---|---|
| | | RSV/A/Tracy Titer ($log_{10}$ total PFU) in Cotton Rat | | | | | | | Change | T test/ |
| Group | Vaccine | A | B | C | D | E | Mean | SD | ($log_{10}$) | 2 v. Gp 1* |
| 1 | Saline | 4.93 | 4.87 | 5.20 | 5.30 | 4.91 | 5.04 | 0.20 | — | — |
| 2 | Live RSV/A/Tracy Day 0 | 1.30 | d | 0.40 | 0.40 | 0.40 | 0.62 | 0.45 | −4.42 | <0.00001 |
| 3 | DT-preF (2 μg) + ALH | 3.79 | 3.15 | 3.99 | 3.24 | 2.93 | 3.42 | 0.45 | −1.62 | 0.000078 |
| 4 | DT-preF (10 μg) + ALH | 2.41 | 2.73 | 3.60 | 3.89 | 3.73 | 3.27 | 0.66 | −1.77 | 0.00024 |

*Minimum detection = 0.70 $log_{10}$ total PFU. d, died. For statistical analysis (Student t test, two-tailed), 0 plaques in an undiluted sample would have been counted as 0.40 $log_{10}$ total PFU. There were additional significant P values: Group 2 v 3, 4; P = 0.00004, 0.00024, respectively (Student t test, two-tailed).

TABLE D

| RSV/A/Tracy Titers in Lung Lavage Fluids on Day +39 | | | | | | | | | | |
|---|---|---|---|---|---|---|---|---|---|---|
| | | RSV/A/Tracy Titer ($log_{10}$ PFU/g lung) in Cotton Rat | | | | | | | Change | T test/ |
| Group | Vaccine | A | B | C | D | E | Mean | SD | ($log_{10}$) | 2 v. Gp 1* |
| 1 | Saline | 5.25 | 5.25 | 5.39 | 5.38 | 5.26 | 5.31 | 0.07 | — | — |
| 2 | Live RSV/A/Tracy Day 0 | 1.23 | d | 1.27 | 1.41 | 1.19 | 1.28 | 0.10 | −4.03 | <0.00001 |
| 3 | DT-preF (2 μg) + ALH | 1.23 | 1.11 | 1.08 | 1.27 | 1.18 | 1.18 | 0.08 | −4.13 | <0.00001 |
| 4 | DT-preF (10 μg) + ALH | 1.34 | 1.10 | 1.27 | 1.16 | 1.46 | 1.27 | 0.14 | −4.04 | <0.00001 |

*Minimum detection ~1.4 $log_{10}$ PFU/g lung. d, died. For statistical analysis (Student t test, two-tailed), 0 plaques in an undiluted sample would have been in the range of 0.90-1.04 $log_{10}$ PFU/g lung. There were no additional significant P values (Student t test, two-tailed).

TABLE E

| RSV/A/Tracy Serum Neutralizing Titer on Day 0 | | | | | | | | | |
|---|---|---|---|---|---|---|---|---|---|
| | | RSV/A Neutralizing Titer ($log_2$) in Cotton Rat | | | | | | | T test/ 2 v. |
| Group | Vaccine | A | B | C | D | E | Mean | SD | Gp 1* |
| 1 | Saline | 2 | | | | | 2 | | |
| 2 | Live RSV/A/Tracy Day 0 | 2 | | | | | 2 | | |
| 3 | DT-preF (2 μg) + ALH | 2 | | | | | 2 | | |
| 4 | DT-preF (10 μg) + ALH | 2 | | | | | 2 | | |

*Student t test, two-tailed. Minimal detection = 2.5; for statistical analysis a value of <2.5 was counted as 2.

TABLE F

| RSV/A/Tracy Serum Neutralizing Titer on Day +21 | | | | | | | | | |
|---|---|---|---|---|---|---|---|---|---|
| | | RSV/A Neutralizing Titer ($log_2$) in Cotton Rat | | | | | | | T test/ |
| Group | Vaccine | A | B | C | D | E | Mean | SD | 2 v. Gp 1* |
| 1 | Saline | 2 | 2 | 2 | 2 | 2 | 2 | 0 | — |
| 2 | Live RSV/A/Tracy Day 0 | 6.5 | d | 5.0 | 5.0 | 5.5 | 5.5 | 0.7 | 0.0000097 |
| 3 | DT-preF (2 μg) + ALH | 2 | 2.5 | 2 | 4.0 | 4.0 | 2.9 | 1.0 | 0.085 |
| 4 | DT-preF (10 μg) + ALH | 3.0 | 2.5 | 4.0 | 2 | 2 | 2.7 | 0.8 | 0.098 |

*Student t test, two-tailed. Minimal detection = 2.5; for statistical analysis a value of <2.5 was counted as 2. Additional significant P values (Student t test, two-tailed): Group 2 v 3, 4, P ≤ 0.0036. d, died.

TABLE G

| RSV/A/Tracy Serum Neutralizing Titer on Day +35 | | | | | | | | | |
|---|---|---|---|---|---|---|---|---|---|
| | | RSV/A Neutralizing Titer ($log_2$) in Cotton Rat | | | | | | | T test/ |
| Group | Vaccine | A | B | C | D | E | Mean | SD | 2 v. Gp 1* |
| 1 | Saline | 2 | 2 | 2 | 2 | 2 | 2 | 0 | — |
| 2 | Live RSV/A/Tracy Day 0 | 6.0 | d | 6.0 | 4.5 | 6.0 | 5.6 | 0.8 | 0.000011 |
| 3 | DT-preF (2 μg) + ALH | 8.5 | 8.5 | 8.0 | 9.0 | 9.5 | 8.7 | 0.6 | <0.00001 |
| 4 | DT-preF (10 μg) + ALH | 9.0 | 9.0 | 9.0 | 8.5 | 9.5 | 9.0 | 0.4 | <0.00001 |

*Student t test, two-tailed. Minimal detection = 2.5; for statistical analysis a value of <2.5 was counted as 2. Additional significant P values (Student t test, two-tailed): Group 2 v 3, 4, P < 0.044; d, died.

TABLE H

| RSV/A/Tracy Serum Neutralizing Titer on Day +39 | | | | | | | | | |
|---|---|---|---|---|---|---|---|---|---|
| | | RSV/A Neutralizing Titer ($log_2$) in Cotton Rat | | | | | | | T test/ |
| Group | Vaccine | A | B | C | D | E | Mean | SD | 2 v. Gp 1* |
| 1 | Saline | 2 | 2 | 2 | 2 | 2 | 2 | 0 | — |
| 2 | Live RSV/A/Tracy Day 0 | 5.0 | d | 6.5 | 5.5 | 6.0 | 5.8 | 0.6 | <0.00001 |
| 3 | DT-preF (2 μg) + ALH | 8.0 | 8.0 | 7.0 | 9.0 | 10.0 | 8.4 | 1.1 | <0.00001 |
| 4 | DT-preF (10 μg) + ALH | 9.0 | 9.0 | 8.5 | 9.0 | 7.5 | 8.6 | 0.7 | <0.00001 |

*Student t test, two-tailed. Minimal detection = 2.5; for statistical analysis a value of <2.5 was counted as 2. Additional significant P values (Student t test, two-tailed): Group 2 v 3, 4, P ≤ 0.0045;. d, died.

TABLE I

| RSV/B/18537 Serum Neutralizing Titer on Day 0 | | | | | | | | | |
|---|---|---|---|---|---|---|---|---|---|
| | | RSV/B Neutralizing Titer ($log_2$) in Cotton Rat | | | | | | | T test/ 2 v. |
| Group | Vaccine | A | B | C | D | E | Mean | SD | Gp 1* |
| 1 | Saline | 2 | | | | | 2 | | |
| 2 | Live RSV/A/Tracy Day 0 | 2 | | | | | 2 | | |
| 3 | DT-preF (2 μg) + ALH | 2 | | | | | 2 | | |
| 4 | DT-preF (10 μg) + ALH | 2 | | | | | 2 | | |

*Student t test, two-tailed. Minimal detection = 2.5; for statistical analysis a value of <2.5 was counted as 2.

TABLE J

| RSV/B/18537 Serum Neutralizing Titer on Day +21 | | | | | | | | | |
|---|---|---|---|---|---|---|---|---|---|
| | | RSV/B Neutralizing Titer ($log_2$) in Cotton Rat | | | | | | | T test/2 v. |
| Group | Vaccine | A | B | C | D | E | Mean | SD | Gp 1* |
| 1 | Saline | 2 | 2 | 2 | 2 | 2 | 2 | 0 | — |
| 2 | Live RSV/A/Tracy Day 0 | 5.0 | d | 3.0 | 3.0 | 2 | 3.3 | 1.3 | 0.058 |
| 3 | DT-preF (2 μg) + ALH | 2 | 2 | 2 | 4.0 | 3.5 | 2.7 | 1.0 | 0.147 |
| 4 | DT-preF (10 μg) + ALH | 2 | 2 | 2 | 2 | 2 | 2 | 0 | — |

*Student t test, two-tailed. Minimal detection = 2.5; for statistical analysis a value of <2.5 was counted as 2. There were no additional significant P values (Student t test, two-tailed).

TABLE K

| RSV/B/18537 Serum Neutralizing Titer on Day +35 | | | | | | | | | |
|---|---|---|---|---|---|---|---|---|---|
| | | RSV/B Neutralizing Titer ($log_2$) in Cotton Rat | | | | | | | T test/2 v. |
| Group | Vaccine | A | B | C | D | E | Mean | SD | Gp 1* |
| 1 | Saline | 2 | 2 | 2 | 2 | 2 | 2 | 0 | — |
| 2 | Live RSV/A/ Tracy Day 0 | 5.0 | d | 3.0 | 2.5 | 2 | 3.1 | 1.3 | 0.092 |
| 3 | DT-preF (2 μg) + ALH | 8.0 | 7.0 | 7.0 | 9.0 | 8.0 | 7.8 | 0.8 | <0.00001 |
| 4 | DT-preF (10 μg) + ALH | 8.0 | 8.5 | 7.5 | 7.5 | 4.0 | 7.1 | 1.8 | 0.00021 |

*Student t test, two-tailed. Minimal detection = 2.5; for statistical analysis a value of <2.5 was counted as 2. Additional significant P values (Student t test, two-tailed): Group 2 v 3, 4, P ≤ 0.015.

TABLE L

| RSV/B/18537 Serum Neutralizing Titer on Day +39 | | | | | | | | | |
|---|---|---|---|---|---|---|---|---|---|
| | | RSV/B Neutralizing Titer ($log_2$) in Cotton Rat | | | | | | | T test/2v. |
| Group | Vaccine | A | B | C | D | E | Mean | SD | Gp 1* |
| 1 | Saline | 2 | 2 | 2 | 2 | 2 | 2 | 0 | — |
| 2 | Live RSV/A/Tracy Day 0 | 5.0 | d | 3.0 | 3.5 | 3.0 | 3.6 | 0.9 | 0.0058 |
| 3 | DT-preF (2 μg) + ALH | 8.0 | 7.0 | 7.0 | 8.5 | 8.0 | 7.7 | 0.7 | <0.00001 |
| 4 | DT-preF (10 μg) + ALH | 8.0 | 8.0 | 7.0 | 5.0 | 7.0 | 7.0 | 1.2 | 0.000017 |

*Student t test, two-tailed. Minimal detection = 2.5; for statistical analysis a value of <2.5 was counted as 2. Additional significant P values (Student t test, two-tailed): Group 2 v 3, 4, P < 0.013.

Cotton rat 2B was found dead in its cage on day 9. Cause of death is unknown.

Figure 9:
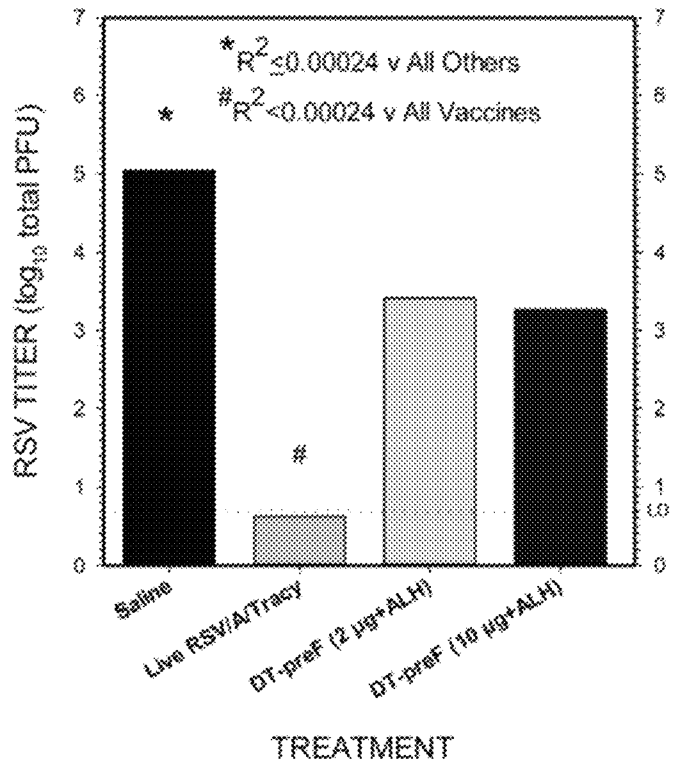
FIG. 9. Efficacy of a DT cross-linked 428Y RSV F mutant (referred to as DT-AVR02 or DT-preF) in vivo in cotton rats. Effect of the DT cross-linked 428Y RSV F mutant adjuvanted with Alhydrogel 2% on RSV/A/Tracy titers in nasal wash fluids at day +39. RSV titers are shown for each of the indicated control and treatment groups.

Effect of DT-preF/DT-AVR02 adjuvanted with Alhydrogel 2% on RSV/A/Tracy titers in nasal wash fluids: Compared to saline controls (group 1) infection with live RSV/A/Tracy on day 0 (group 2) reduced titers by 4.42 $\log_{10}$ total PFU (P<0.00001; Student t test, two-tailed) (FIG. 9, Table B). All of the vaccine combinations reduced virus titers by 1.37 to 1.77 $\log_{10}$ total PFU (P≤0.00024; Student t test, two-tailed). There were no statistical differences between the vaccine combinations.

Figure 10:
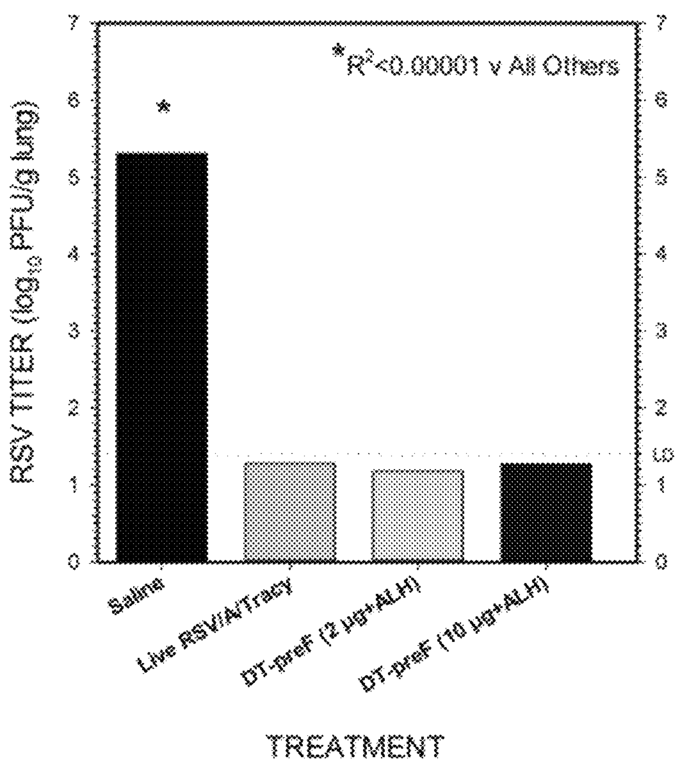
FIG. 10. Efficacy of a DT cross-linked 428Y RSV F mutant (DT-AVR02/DT-preF) in vivo in cotton rats. the DT cross-linked 428Y RSV F mutant adjuvanted with Alhydrogel 2% on RSV/A/Tracy titers in lung lavage fluids at day +39. RSV titers are shown for each of the indicated control and treatment groups.

Effect of DT-preF/DT-AVR02 adjuvanted with Alhydrogel 2% on RSV/A/Tracy titers in lung lavage fluids: Compared to saline controls (group 1) infection with live RSV/A/Tracy on day 0 (group 2) reduced titers to below the limit of detection (4.03 $\log_{10}$ PFU/g lung; P<0.00001; Student t test, two-tailed) (FIG. 10, Table C). Vaccine combinations for groups 3 and 4 RSV titers were reduced to below the limit of detection (4.04-4.13 $\log_{10}$ PFU/g lung; P<0.00001; Student t test, two-tailed). There were no statistical differences between the vaccine combinations.

Figure 11:
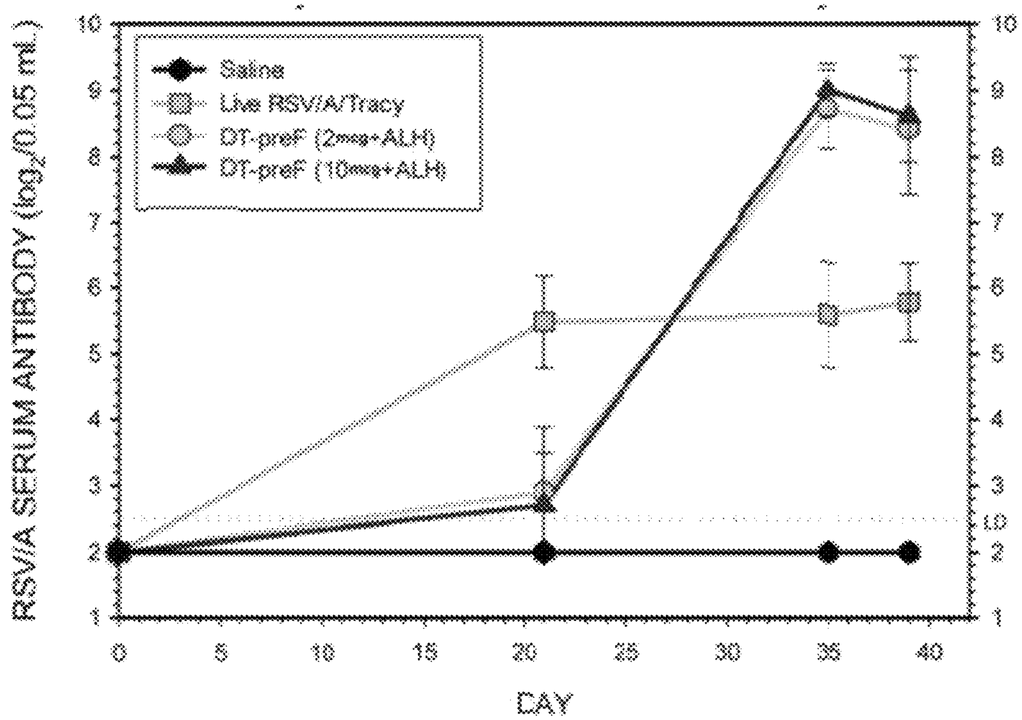
FIG. 11. Efficacy of a DT cross-linked 428Y RSV F mutant (DT-AVR02/DT-preF) in vivo in cotton rats. Effect of DT-preF adjuvanted with Alhydrogel 2% on generation of RSV/A/Tracy serum neutralizing antibodies.

Effect of DT-preF/DT-AVR02 adjuvanted with Alhydrogel 2% on generation of RSV/A/Tracy- or RSV/B/18537-specific neutralizing antibody: For RSV/A/Tracy-specific neutralizing antibody (NtAb) natural infection with live RSV/A/Tracy (group 2) generated NtAb by day 21 (ca. 5.5 $\log_2$/0.05 mL) and remained at that level through day 39 (FIG. 11; Tables D-G). This was statistically different than any of the DT-AVR02 vaccines at day 21 (P≤0.0036; Student t test, two-tailed). However, following the second vaccination on day 21, there was a robust NtAb response with all of the vaccines which was greater than the live RSV/A/Tracy infection.

Figure 12:
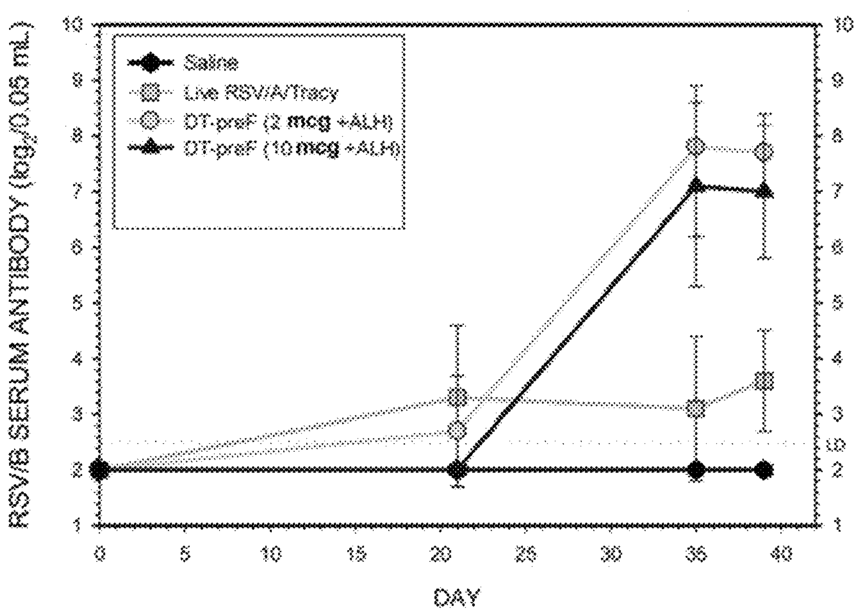
FIG. 12. Efficacy of a DT cross-linked 428Y RSV F mutant (DT-AVR02/DT-preF) in vivo in cotton rats. Effect of DT-preF adjuvanted with Alhydrogel 2% on generation of RSV/B/1853 cross-reacting neutralizing antibodies.

RSV/B/1853 cross-reacting NtAb were generated by live RSV/A/Tracy infection and by the 2vaccines (FIG. 12; Tables H-L). The pattern of the NtAb response for the 2 vaccines was similar to that for RSV/A/Tracy but 1-2 $\log_2$ levels lower.

Example 5

Comparison of 428Y and 427Y Mutant RSV F Molecules In Vitro & In Vivo

Two DT cross linked mutant RSV F molecules stabilized in the pre-F conformation were generated—using the methods described in the previous Examples. The two mutants differed only in that one had a to-tyrosine point mutation at amino acid 428 (a 428Y mutation) and the other had a to-tyrosine point mutation at amino acid 427 (a 427Y mutation). Both molecules comprised S190F and V207L mutations (i.e. "Cav1" mutations) and to-tyrosine mutations at amino acid residues 185 and 226 (i.e. a 185Y mutation and a 226Y mutation).

The 428Y mutant (comprising V185Y, K428Y, K226Y, S190F and V207L mutations) is referred interchangeably herein as either "428Y mutant" or "DT-AVR02." The F0 precursor form of the 428Y mutant has the amino acid sequence of SEQ ID NO. 81. The mature 428Y mutant molecule (formed after transfection and expression in cells of a nucleic acid molecule that encodes SEQ ID NO. 81) comprises amino acid residues 26-109 and 137-568 of SEQ ID No. 81—where amino acid residues 26-109 are RSV F F2 residues, amino acid residues 137-513 are RSV F F1 residues, and amino acid residues 514-568 are heterologous sequences and includes a foldon domain, a His tag, a StrepII tag, and a thrombin cleavage site. The signal peptides from amino acids 1-25 and the pep27 peptide from amino acids 100-136 are not present in the final mature trimeric 428Y mutant molecule.

The 427Y mutant (comprising V185Y, K427Y, K226Y, S190F and V207L mutations) is referred interchangeably herein as either "427Y mutant" or "DT-CAV1." The F0 precursor form of the 428Y mutant has the amino acid sequence of SEQ ID NO. 81 with the exception that it comprises a lysine (K) residue at amino acid position 428 and comprises a tyrosine at amino acid position 427. The mature 427Y mutant molecule (formed after transfection and expression in cells of a nucleic acid molecule that encodes this modified version of SEQ ID NO. 81) comprises amino acid residues 26-109 and 137-568 of that modified sequence—where amino acid residues 26-109 are RSV F F2 residues, amino acid residues 137-513 are RSV F F1 residues, and amino acid residues 514-568 are heterologous sequences and includes a foldon domain, a His tag, a StrepII tag, and a thrombin cleavage site. The signal peptides from amino acids 1-25 and the pep27 peptide from amino acids 100-136 are not present in the final mature trimeric 427Y mutant molecule.

The 427Y and 428Y mutants were expressed and purified according to the methods described above and analyzed for conformational integrity via ELISA using motavizumab to normalize total protein, and the conformational 5C4 (site Ø, prefusion-specific) antibody, and a prefusion specific monoclonal antibody that binds to the region between sites antigenic sites IV and V. Ni-NTA coated plates were used (Qiagen) and the assay was developed with one-step TMB reagent (Pierce). As indicated in FIG. 13, the substitution N428Y in place of K427Y markedly improves binding to the site IV-V antibody (FIGS. 13B & D) and also improves binding to the site Ø antibody (FIG. 13A & C).

The substitution of N428Y for K427Y also impacts the aggregation state of the molecule following the crosslinking reaction. Proteins were purified according to the methods \described elsewhere herein and both proteins were crosslinked under identical conditions and processed as described elsewhere herein. During size exclusion chromatography using a Superdex 200 26/60 pg column with PBS as the eluent, the chromatograms of the crosslinked material differ significantly. As shown in FIG. 14A, following the crosslinking reaction, the 427Y mutant (DT-CAV1) produces primarily a higher-order aggregate species as indicated in FIG. 14, and on the corresponding Coomassie-stained SDS-PAGE analysis of the final product (FIG. 14C, left two gel panels). When the 428Y mutant (DT-AVR02) is produced by the same process, a majority of the protein is in the trimeric fraction as evident by the chromatogram (FIG. 14B) and the corresponding Coomassie-stained SDS-PAGE gel of the final product (FIG. 14C, right gel panel).

Studies were also performed to test the immunogenicity of the 427Y mutant (DT-CAV1), the 427Y mutant (DT-AVR02), and the DS-Cav1 mutant described in Mclellan et al. (2013) Science 342:592-598 (which comprises S155C, S290C, S190F, and V207L mutations). Two groups of 10, 6-8 week old, pathogen free, female CB6/F1J mice (Jackson Labs) were immunized in a prime (Day 0)-boost (Day 21) regimen: In both studies group 1 was vaccinated with 10 ug (micrograms) of Alum-adjuvanted DS-Cav1, while group 2 in the first study was vaccinated with 10 ug (micrograms) per animal, per dose of the alum-adjuvanted 427Y mutant (DT-CAV1), and in the second study with 10 ug (micrograms) per animal, per dose of the alum-adjuvanted 428Y mutant (DT-AVR02). Serum was collected at time, on day 35, two weeks after the second vaccination (boost). The results are shown in FIGS. 15A-B—which shows that serum neutralization titers from animals vaccinated with the 428Y mutant (DT-AVR02) (FIG. 15B) are dramatically higher than those from those vaccinated with the 427Y mutant (DT-Cav1) (FIG. 15A).

Example 6

Formulation with Sucrose Reduces Formation of RSV F Aggregates

It has been found that inclusion of sucrose in formulations of the mutant RSV F molecules of the invention significantly reduces the formation of undesirable aggregates. Experiments were performed using the exemplary DT-cross-linked 428Y mutant (DT-AVR02) described above. After final concentration, analytical size-exclusion chromatography (SEC) demonstrated the presence of the desired DT-AVR02 trimers (peak C in FIG. 16A) and also aggregates (peaks A and B in FIG. 16A). Formulation of the DT-AVR02 molecule with 10% sucrose during elution of the purification step appeared to eliminate the formation of aggregates. As shown in FIG. 16B peak C (trimers) remained but peaks A and B (aggregates) were not apparent in the samples formulated with sucrose.

Example 7

In Vivo Testing of AVR02 in Non-Human Primates

Six groups of 5 non-human primates are immunized via intramuscular injection in a prime (Day 0)—boost (Day 28) regimen. Groups 1 and 2 are vaccinated with a high dose (50 mg/per animal/injection) of DT-AVR02, with (Group 1) and without (Group 2) adjuvant; Groups 3 and 4 are vaccinated with a low dose (10 mg/animal/injection) of DT-AVR02, with (Group 3) and without (Group 4) adjuvant; and Groups 5 and 6 are vaccinated with a high dose (50 mg/per animal/injection) of our comparator, DS-Cav1, with (Group 1) and without (Group 2) adjuvant.

Animals in all groups are injected twice, on days 0 and 28. Blood is drawn from all animals on day 0, prior to the prime, and on day 28, prior to the second immunization. Blood is again drawn/collected on day 42 and 49. Peripheral blood mononuclear cells are isolated by standard methods in order to characterize the frequency and phenotype (Th1/Th2) of RSV-specific T cell responses; and serum is analyzed to quantify NHP anti-F responses (IgM, Total IgG, IgG1, IgG2, IgG3), to perform epitope analysis by competition analysis, carried out by standard methods (site Ø and site II), and to quantify neutralization titers, also carried out by standard methods.

Example 8

Phase I Human Clinical Trial of AVR02

Randomized, Placebo-Controlled, Observer-Blinded, Escalating Dose-Ranging Study to Assess the Safety, Tolerability and immunogenicity of a Stabilized Prefusion RSV F Subunit Protein Vaccine, DT-AVR02, Alone or With Alum Adjuvant in healthy (non-pregnant) adults (18 to 50 years of age).

150 subjects are distributed across 7 cohorts, testing 6 formulations and a placebo. Subjects are randomly assigned to vaccine treatment or saline placebo in a 4:1 ratio, so that each cohort includes 20 subjects receiving active vaccine (Groups A, B, C, D, E and F) and 5 subjects receiving placebo (Group G). 6 groups of 20 (active vaccine) and 5 (placebo) subjects are tested. 6×25=150 subjects. Low, medium, and high doses, (50 mcg, 150 mcg, and 500 mcg per injection), each dose formulated with and without alum as an adjuvant.

Subjects are injected IM twice: on Days 0 and Day 90 (+/−5 days). Subjects are followed for all Adverse Events (AEs), including Serious AEs (SAEs) and non-serious AEs, from the time of each vaccination (Days 0 and 90) through 30 days following the vaccination. Furthermore, subjects are contacted via telephone on Days 60, 150, 180, 210, and 310) and asked about the occurrence of SAEs and significant new medical conditions.

The primary objective is to evaluate the safety, reactogenicity, and tolerability of three doses of DT-AVR02 alone or with alum when administered IM to healthy adults, monitored over 44 weeks. The secondary objective is to evaluate the antibody responses in test subjects to three doses of unadjuvanted and adjuvanted DT-AVR02, as measured by: ELISAs to evaluate total Ab responses (including Ab subtype analysis), competition ELISAs to evaluate epitope-specific responses, 2 and 4 weeks after each injection, and Neutralization assays, 2 and 4 weeks after each injection.

While the foregoing invention has been described in some detail for purposes of clarity and understanding, it will be clear to one skilled in the art from a reading of this disclosure that various changes in form and detail can be made without departing from the true scope of the invention. The invention may also be further defined in terms of the following claims.

SEQUENCE LISTING

```
Sequence total quantity: 96
SEQ ID NO: 1            moltype = AA  length = 574
FEATURE                 Location/Qualifiers
source                  1..574
                        mol_type = protein
                        organism = unidentified
                        note = Respiratory syncytial virus
SEQUENCE: 1
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PPTNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEIN LCNVDIFNPK YDCKIMTSKT DVSSSVITSL GAIVSCYGKT  420
KCTASNKNRG IIKTFSNGCD YVSNKGMDTV SVGNTLYYVN KQEGKSLYVK GEPIINFYDP  480
```

```
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                               574

SEQ ID NO: 2            moltype = AA  length = 574
FEATURE                 Location/Qualifiers
source                  1..574
                        mol_type = protein
                        organism = unidentified
                        note = Respiratory syncytial virus
SEQUENCE: 2
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVILS KDQLSGINNI AFSN                               574

SEQ ID NO: 3            moltype = AA  length = 574
FEATURE                 Location/Qualifiers
source                  1..574
                        mol_type = protein
                        organism = unidentified
                        note = Respiratory syncytial virus
SEQUENCE: 3
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                               574

SEQ ID NO: 4            moltype = AA  length = 574
FEATURE                 Location/Qualifiers
source                  1..574
                        mol_type = protein
                        organism = unidentified
                        note = Respiratory syncytial virus
SEQUENCE: 4
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                               574

SEQ ID NO: 5            moltype = AA  length = 574
FEATURE                 Location/Qualifiers
source                  1..574
                        mol_type = protein
                        organism = unidentified
                        note = Respiratory syncytial virus
SEQUENCE: 5
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST QAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                               574

SEQ ID NO: 6            moltype = AA  length = 574
FEATURE                 Location/Qualifiers
source                  1..574
                        mol_type = protein
```

```
                        organism = unidentified
                        note = Respiratory syncytial virus
SEQUENCE: 6
MELPIIKANA ITTILIAVTF CFASSQNITE EFYQSTCSAV SKGYLSALRT GWYTSVITIE  60
LSNIKENKCN GTDAKVKLIK QELDKYKNAV TELQLLMQST TAANNRARRE LPRFMNYTLN  120
NAKKTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                            574

SEQ ID NO: 7            moltype = AA  length = 574
FEATURE                 Location/Qualifiers
source                  1..574
                        mol_type = protein
                        organism = unidentified
                        note = Respiratory syncytial virus
SEQUENCE: 7
MELPILKTNA ITTILTAVTF CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLLLYC KARSTPVTLS KDQLSGINNI AFSN                            574

SEQ ID NO: 8            moltype = AA  length = 574
FEATURE                 Location/Qualifiers
source                  1..574
                        mol_type = protein
                        organism = unidentified
                        note = Respiratory syncytial virus
SEQUENCE: 8
MELPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KEQLSGINNI AFSN                            574

SEQ ID NO: 9            moltype = AA  length = 574
FEATURE                 Location/Qualifiers
source                  1..574
                        mol_type = protein
                        organism = unidentified
                        note = Respiratory syncytial virus
SEQUENCE: 9
MELPILKTNA ITTIFAAVTL CFASSQNITE EFYQSTCSAV SKGYLSALRT GWYTSVITVE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                            574

SEQ ID NO: 10           moltype = AA  length = 568
FEATURE                 Location/Qualifiers
source                  1..568
                        mol_type = protein
                        organism = unidentified
                        note = Respiratory syncytial virus
SEQUENCE: 10
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
```

-continued

```
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHSA WSHPQFEK                                    568

SEQ ID NO: 11          moltype = AA  length = 574
FEATURE                Location/Qualifiers
source                 1..574
                       mol_type = protein
                       organism = unidentified
                       note = Respiratory syncytial virus
SEQUENCE: 11
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NRLLPIVNQQ SCRISNIETV IEFQQMNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                              574

SEQ ID NO: 12          moltype = AA  length = 574
FEATURE                Location/Qualifiers
source                 1..574
                       mol_type = protein
                       organism = unidentified
                       note = Respiratory syncytial virus
SEQUENCE: 12
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 13          moltype = AA  length = 574
FEATURE                Location/Qualifiers
source                 1..574
                       mol_type = protein
                       organism = unidentified
                       note = Respiratory syncytial virus
SEQUENCE: 13
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNKQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DVSSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 14          moltype = AA  length = 574
FEATURE                Location/Qualifiers
source                 1..574
                       mol_type = protein
                       organism = unidentified
                       note = Respiratory syncytial virus
SEQUENCE: 14
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PVANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNTKEGS NICLTRTDRG WYCDNAGSVS FFPQADTCKV  360
QSNRVFCDTM YSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574
```

-continued

```
SEQ ID NO: 15          moltype = AA  length = 574
FEATURE                Location/Qualifiers
source                 1..574
                       mol_type = protein
                       organism = unidentified
                       note = Respiratory syncytial virus
SEQUENCE: 15
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GMAVSKVLHL EGEVNKIKNA LLSTNKAVVS  180
LSNGISVLTS KVLDLKNYIN NRLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                              574

SEQ ID NO: 16          moltype = AA  length = 574
FEATURE                Location/Qualifiers
source                 1..574
                       mol_type = protein
                       organism = unidentified
                       note = Respiratory syncytial virus
SEQUENCE: 16
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IMKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITVI IIVIIVVLLS  540
LIAIGLLLYC KAKNTPVTLS KDQLSGINNI AFSK                              574

SEQ ID NO: 17          moltype = AA  length = 574
FEATURE                Location/Qualifiers
source                 1..574
                       mol_type = protein
                       organism = unidentified
                       note = Respiratory syncytial virus
SEQUENCE: 17
MELLIHRSIA IFLTLAINAL YLTSSQNITE EFYQSTCSAV SRGYFSALRT GWYTSVITIE  60
LSNITETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNVGK STTNIMITAI IIVIIVVLLS  540
LIAIGLLLYC KAKNTPVTLS KDQLSGINNI AFSK                              574

SEQ ID NO: 18          moltype = AA  length = 574
FEATURE                Location/Qualifiers
source                 1..574
                       mol_type = protein
                       organism = unidentified
                       note = Respiratory syncytial virus
SEQUENCE: 18
MELLVHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTNNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEIAREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 19          moltype = AA  length = 574
FEATURE                Location/Qualifiers
source                 1..574
                       mol_type = protein
                       organism = unidentified
                       note = Respiratory syncytial virus
SEQUENCE: 19
```

-continued

```
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NRLLPIVNQQ SCRISNIETV IEFQQMNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                            574

SEQ ID NO: 20          moltype = AA  length = 574
FEATURE                Location/Qualifiers
source                 1..574
                       mol_type = protein
                       organism = unidentified
                       note = Respiratory syncytial virus
SEQUENCE: 20
MELLIHRSSA IFLTLAINAL YLTSSQNITE EFYQSTCSAV SRGYFSALRT GWYTSVITIE  60
LSNITETKCN GTDTKVKLIK QELDKYKNAV TELQLLMQNT PAANNRARRE APQHMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRIFNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRKSD ELLHNVNTGK STTNIMITTI IIVIIVVLLS  540
LIAIGLLLYC KAKNTPVTLS KDQLSGINNI AFSK                            574

SEQ ID NO: 21          moltype = AA  length = 574
FEATURE                Location/Qualifiers
source                 1..574
                       mol_type = protein
                       organism = unidentified
                       note = Respiratory syncytial virus
SEQUENCE: 21
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PPTNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEIN LCNVDIFNPK YDCKIMTSKT DVSSSVITSL GAIVSCYGKT  420
KCTASNKYRG IIKTFSNGCD YVSNKGMDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                            574

SEQ ID NO: 22          moltype = AA  length = 574
FEATURE                Location/Qualifiers
source                 1..574
                       mol_type = protein
                       organism = unidentified
                       note = Respiratory syncytial virus
SEQUENCE: 22
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVILS KDQLSGINNI AFSN                            574

SEQ ID NO: 23          moltype = AA  length = 574
FEATURE                Location/Qualifiers
source                 1..574
                       mol_type = protein
                       organism = unidentified
                       note = Respiratory syncytial virus
SEQUENCE: 23
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
```

-continued

```
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 24          moltype = AA  length = 574
FEATURE                Location/Qualifiers
source                 1..574
                       mol_type = protein
                       organism = unidentified
                       note = Respiratory syncytial virus
SEQUENCE: 24
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 25          moltype = AA  length = 574
FEATURE                Location/Qualifiers
source                 1..574
                       mol_type = protein
                       organism = unidentified
                       note = Respiratory syncytial virus
SEQUENCE: 25
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST QAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 26          moltype = AA  length = 574
FEATURE                Location/Qualifiers
source                 1..574
                       mol_type = protein
                       organism = unidentified
                       note = Respiratory syncytial virus
SEQUENCE: 26
MELPIIKANA ITTILIAVTF CFASSQNITE EFYQSTCSAV SKGYLSALRT GWYTSVITIE  60
LSNIKENKCN GTDAKVKLIK QELDKYKNAV TELQLLMQST TAANNRARRE LPRFMNYTLN  120
NAKKTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 27          moltype = AA  length = 574
FEATURE                Location/Qualifiers
source                 1..574
                       mol_type = protein
                       organism = unidentified
                       note = Respiratory syncytial virus
SEQUENCE: 27
MELPILKTNA ITTILTAVTF CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLLLYC KARSTPVTLS KDQLSGINNI AFSN                              574

SEQ ID NO: 28          moltype = AA  length = 574
FEATURE                Location/Qualifiers
source                 1..574
```

```
                        mol_type = protein
                        organism = unidentified
                        note = Respiratory syncytial virus
SEQUENCE: 28
MELPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IVIIVILLL  540
LIAVGLFLYC KARSTPVTLS KEQLSGINNI AFSN                              574

SEQ ID NO: 29           moltype = AA  length = 574
FEATURE                 Location/Qualifiers
source                  1..574
                        mol_type = protein
                        organism = unidentified
                        note = Respiratory syncytial virus
SEQUENCE: 29
MELPILKTNA ITTIFAAVTL CFASSQNITE EFYQSTCSAV SKGYLSALRT GWYTSVITVE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IVIIVILLS  540
LIAVGLLLYC KARSTPVTLS KDQLSGINNI AFSN                              574

SEQ ID NO: 30           moltype = AA  length = 568
FEATURE                 Location/Qualifiers
source                  1..568
                        mol_type = protein
                        organism = unidentified
                        note = Respiratory syncytial virus
SEQUENCE: 30
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHSA WSHPQFEK                                    568

SEQ ID NO: 31           moltype = AA  length = 574
FEATURE                 Location/Qualifiers
source                  1..574
                        mol_type = protein
                        organism = unidentified
                        note = Respiratory syncytial virus
SEQUENCE: 31
MELPILKTNA ITTIFAAVTL CFASSQNITE EFYQSTCSAV SKGYLSALRT GWYTSVITVE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IVIIVILLS  540
LIAVGLLLYC KARSTPVTLS KDQLSGINNI AFSN                              574

SEQ ID NO: 32           moltype = AA  length = 574
FEATURE                 Location/Qualifiers
source                  1..574
                        mol_type = protein
                        organism = unidentified
                        note = Respiratory syncytial virus
SEQUENCE: 32
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
```

-continued

```
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                            574

SEQ ID NO: 33          moltype = AA  length = 573
FEATURE                Location/Qualifiers
source                 1..573
                       mol_type = protein
                       organism = unidentified
                       note = Respiratory syncytial virus
SEQUENCE: 33
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNKQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DVSSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFS                             573

SEQ ID NO: 34          moltype = AA  length = 574
FEATURE                Location/Qualifiers
source                 1..574
                       mol_type = protein
                       organism = unidentified
                       note = Respiratory syncytial virus
SEQUENCE: 34
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PVANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNTKEGS NICLTRTDRG WYCDNAGSVS FFPQADTCKV  360
QSNRVFCDTM YSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                            574

SEQ ID NO: 35          moltype = AA  length = 574
FEATURE                Location/Qualifiers
source                 1..574
                       mol_type = protein
                       organism = unidentified
                       note = Respiratory syncytial virus
SEQUENCE: 35
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PVANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNTKEGS NICLTRTDRG WYCDNAGSVS FFPQADTCKV  360
QSNRVFCDTM YSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                            574

SEQ ID NO: 36          moltype = AA  length = 574
FEATURE                Location/Qualifiers
source                 1..574
                       mol_type = protein
                       organism = unidentified
                       note = Respiratory syncytial virus
SEQUENCE: 36
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IMKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITVI IIVIIVVLLS  540
LIAIGLLLYC KAKNTPVTLS KDQLSGINNI AFSK                            574
```

```
SEQ ID NO: 37          moltype = AA  length = 574
FEATURE                Location/Qualifiers
source                 1..574
                       mol_type = protein
                       organism = unidentified
                       note = Respiratory syncytial virus
SEQUENCE: 37
MELLIHRSIA IFLTLAINAL YLTSSQNITE EFYQSTCSAV SRGYFSALRT GWYTSVITIE  60
LSNITETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNVGK STTNIMITAI IIVIIVVLLS  540
LIAIGLLLYC KAKNTPVTLS KDQLSGINNI AFSK                              574

SEQ ID NO: 38          moltype = AA  length = 574
FEATURE                Location/Qualifiers
source                 1..574
                       mol_type = protein
                       organism = unidentified
                       note = Respiratory syncytial virus
SEQUENCE: 38
MELLVHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTNNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEIAREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 39          moltype = AA  length = 574
FEATURE                Location/Qualifiers
source                 1..574
                       mol_type = protein
                       organism = unidentified
                       note = Respiratory syncytial virus
SEQUENCE: 39
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NRLLPIVNQQ SCRISNIETV IEFQQMNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                              574

SEQ ID NO: 40          moltype = AA  length = 574
FEATURE                Location/Qualifiers
source                 1..574
                       mol_type = protein
                       organism = unidentified
                       note = Respiratory syncytial virus
SEQUENCE: 40
MELLIHRSSA IFLTLAINAL YLTSSQNITE EFYQSTCSAV SRGYFSALRT GWYTSVITIE  60
LSNITETKCN GTDTKVKLIK QELDKYKNAV TELQLLMQNT PAANNRARRE APQHMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRIFNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRKSD ELLHNVNTGK STTNIMITTI IIVIIVVLLS  540
LIAIGLLLYC KAKNTPVTLS KDQLSGINNI AFSK                              574

SEQ ID NO: 41          moltype = AA  length = 574
FEATURE                Location/Qualifiers
source                 1..574
                       mol_type = protein
                       organism = unidentified
                       note = Respiratory syncytial virus
```

```
SEQUENCE: 41
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PPTNNRARRE LPRFMNYTLN  120
NAKKTNVTLS KKRKRRFLGF LLGVGSAIAS GVAVSKVLHL EGEVNKIKSA LLSTNKAVVS  180
LSNGYSVLTS KVLDLKNYID KQLLPIVNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEIN LCNVDIFNPK YDCKIMTSKT DVSSSVITSL GAIVSCYGKT  420
KCTASNKYRG IIKTFSNGCD YVSNKGMDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                            574

SEQ ID NO: 42           moltype = AA  length = 574
FEATURE                 Location/Qualifiers
source                  1..574
                        mol_type = protein
                        organism = unidentified
                        note = Respiratory syncytial virus
SEQUENCE: 42
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGYSVLTS KVLDLKNYID KQLLPIVNKQ SCSISNIETV IEFQQYNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVILS KDQLSGINNI AFSN                            574

SEQ ID NO: 43           moltype = AA  length = 574
FEATURE                 Location/Qualifiers
source                  1..574
                        mol_type = protein
                        organism = unidentified
                        note = Respiratory syncytial virus
SEQUENCE: 43
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGYSVLTS KVLDLKNYID KQLLPIVNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                            574

SEQ ID NO: 44           moltype = AA  length = 574
FEATURE                 Location/Qualifiers
source                  1..574
                        mol_type = protein
                        organism = unidentified
                        note = Respiratory syncytial virus
SEQUENCE: 44
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKTTNVTLS KKRKRRFLGF LLGVGSAIAS GIAVSKVLHL EGEVNKIKSA LLSTNKAVVS  180
LSNGYSVLTS KVLDLKNYID KQLLPIVNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNTDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                            574

SEQ ID NO: 45           moltype = AA  length = 574
FEATURE                 Location/Qualifiers
source                  1..574
                        mol_type = protein
                        organism = unidentified
                        note = Respiratory syncytial virus
SEQUENCE: 45
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST QAANSRARRE LPRFMNYTLN  120
NTKNTNVTLS KKRKRRFLGF LLGVGSAIAS GIAVSKVLHL EGEVNKIKSA LLSTNKAVVS  180
LSNGYSVLTS KVLDLKNYID KQLLPIVNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
```

```
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 46          moltype = AA  length = 574
FEATURE                Location/Qualifiers
source                 1..574
                       mol_type = protein
                       organism = unidentified
                       note = Respiratory syncytial virus
SEQUENCE: 46
MELLVHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTNNLNVSIS KKRKRRFLGF LLGVGSAIAS GIAVSKVLHL EGEVNKIKNA LLSTNKAVVS  180
LSNGYSVLTS KVLDLKNYIN NQLLPIVNQQ SCRISNIETV IEFQQYNSRL LEIAREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 47          moltype = AA  length = 574
FEATURE                Location/Qualifiers
source                 1..574
                       mol_type = protein
                       organism = unidentified
                       note = Respiratory syncytial virus
SEQUENCE: 47
MELPILKTNA ITTILTAVTF CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGYSVLTS KVLDLKNYID KQLLPIVNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLLLYC KARSTPVTLS KDQLSGINNI AFSN                             574

SEQ ID NO: 48          moltype = AA  length = 574
FEATURE                Location/Qualifiers
source                 1..574
                       mol_type = protein
                       organism = unidentified
                       note = Respiratory syncytial virus
SEQUENCE: 48
MELPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGYSVLTS KVLDLKNYID KQLLPIVNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KEQLSGINNI AFSN                             574

SEQ ID NO: 49          moltype = AA  length = 574
FEATURE                Location/Qualifiers
source                 1..574
                       mol_type = protein
                       organism = unidentified
                       note = Respiratory syncytial virus
SEQUENCE: 49
MELPILKTNA ITTIFAAVTL CFASSQNITE EFYQSTCSAV SKGYLSALRT GWYTSVITVE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGYSVLTS KVLDLKNYID KQLLPIVNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 50          moltype = AA  length = 568
FEATURE                Location/Qualifiers
```

```
source                  1..568
                        mol_type = protein
                        organism = unidentified
                        note = Respiratory syncytial virus
SEQUENCE: 50
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGYSVLTS KVLDLKNYID KQLLPIVNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHSA WSHPQFEK                                    568

SEQ ID NO: 51           moltype = AA  length = 574
FEATURE                 Location/Qualifiers
source                  1..574
                        mol_type = protein
                        organism = unidentified
                        note = Respiratory syncytial virus
SEQUENCE: 51
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTS KVLDLKNYIN NRLLPIVNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IVIIVVLLS  540
LIAIGLLLYC KAKNTPVTLS KDQLSGINNI AFSK                              574

SEQ ID NO: 52           moltype = AA  length = 574
FEATURE                 Location/Qualifiers
source                  1..574
                        mol_type = protein
                        organism = unidentified
                        note = Respiratory syncytial virus
SEQUENCE: 52
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTS KVLDLKNYIN NQLLPIVNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IVIIVVLLS  540
LIAIGLLLYC KAKNTPVTLS KDQLSGINNI AFSK                              574

SEQ ID NO: 53           moltype = AA  length = 573
FEATURE                 Location/Qualifiers
source                  1..573
                        mol_type = protein
                        organism = unidentified
                        note = Respiratory syncytial virus
SEQUENCE: 53
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTS KVLDLKNYIN NQLLPIVNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DVSSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IVIIVVLLS  540
LIAIGLLLYC KAKNTPVTLS KDQLSGINNI AFS                               573

SEQ ID NO: 54           moltype = AA  length = 574
FEATURE                 Location/Qualifiers
source                  1..574
                        mol_type = protein
                        organism = unidentified
                        note = Respiratory syncytial virus
SEQUENCE: 54
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PVANNRARRE APQYMNYTIN  120
```

-continued

```
TTKNLNVSIS KKRKRRFLGF LLGVGSAIAS GIAVSKVLHL EGEVNKIKNA LLSTNKAVVS  180
LSNGYSVLTS KVLDLKNYIN NQLLPIVNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNTKEGS NICLTRTDRG WYCDNAGSVS FFPQADTCKV  360
QSNRVFCDTM YSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 55          moltype = AA  length = 574
FEATURE                Location/Qualifiers
source                 1..574
                       mol_type = protein
                       organism = unidentified
                       note = Respiratory syncytial virus
SEQUENCE: 55
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GMAVSKVLHL EGEVNKIKNA LLSTNKAVVS  180
LSNGYSVLTS KVLDLKNYIN NRLLPIVNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                              574

SEQ ID NO: 56          moltype = AA  length = 574
FEATURE                Location/Qualifiers
source                 1..574
                       mol_type = protein
                       organism = unidentified
                       note = Respiratory syncytial virus
SEQUENCE: 56
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTS KVLDLKNYIN NQLLPIVNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 57          moltype = AA  length = 573
FEATURE                Location/Qualifiers
source                 1..573
                       mol_type = protein
                       organism = unidentified
                       note = Respiratory syncytial virus
SEQUENCE: 57
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTS KVLDLKNYIN NQLLPIVNKQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DVSSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFS                               573

SEQ ID NO: 58          moltype = AA  length = 574
FEATURE                Location/Qualifiers
source                 1..574
                       mol_type = protein
                       organism = unidentified
                       note = Respiratory syncytial virus
SEQUENCE: 58
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PVANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTS KVLDLKNYIN NQLLPIVNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNTKEGS NICLTRTDRG WYCDNAGSVS FFPQADTCKV  360
QSNRVFCDTM YSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
```

-continued

```
LIAIGLLLYC KAKNTPVTLS KDQLSGINNI AFSK                        574

SEQ ID NO: 59          moltype = AA  length = 574
FEATURE                Location/Qualifiers
source                 1..574
                       mol_type = protein
                       organism = unidentified
                       note = Respiratory syncytial virus
SEQUENCE: 59
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GMAVSKVLHL EGEVNKIKNA LLSTNKAVVS  180
LSNGYSVLTS KVLDLKNYIN NRLLPIVNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                        574

SEQ ID NO: 60          moltype = AA  length = 574
FEATURE                Location/Qualifiers
source                 1..574
                       mol_type = protein
                       organism = unidentified
                       note = Respiratory syncytial virus
SEQUENCE: 60
MELLIHRSSA IFLTLAINAL YLTSSQNITE EFYQSTCSAV SRGYFSALRT GWYTSVITIE  60
LSNITETKCN GTDTKVKLIK QELDKYKNAV TELQLLMQNT PAANNRARRE APQHMNYTIN  120
TTKNLNVSIS KKRKRRFLGF LLGVGSAIAS GIAVSKVLHL EGEVNKIKNA LLSTNKAVVS  180
LSNGYSVLTS KVLDLKNYIN NQLLPIVNQQ SCRIFNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRKSD ELLHNVNTGK STTNIMITTI IIVIIVVLLS  540
LIAIGLLLYC KAKNTPVTLS KDQLSGINNI AFSK                        574

SEQ ID NO: 61          moltype = AA  length = 574
FEATURE                Location/Qualifiers
source                 1..574
                       mol_type = protein
                       organism = unidentified
                       note = Respiratory syncytial virus
SEQUENCE: 61
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PPTNNRARRE LPRFMNYTLN  120
NAKKTNVTLS KKRKRRFLGF LLGVGSAIAS GVAVSKVLHL EGEVNKIKSA LLSTNKAVVS  180
LSNGYSVLTF KVLDLKNYID KQLLPILNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEIN LCNVDIFNPK YDCKIMTSKT DVSSSVITSL GAIVSCYGKT  420
KCTASNKYRG IIKTFSNGCD YVSNKGMDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                        574

SEQ ID NO: 62          moltype = AA  length = 574
FEATURE                Location/Qualifiers
source                 1..574
                       mol_type = protein
                       organism = unidentified
                       note = Respiratory syncytial virus
SEQUENCE: 62
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGYSVLTF KVLDLKNYID KQLLPILNKQ SCSISNIETV IEFQQYNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVILS KDQLSGINNI AFSN                        574

SEQ ID NO: 63          moltype = AA  length = 574
FEATURE                Location/Qualifiers
source                 1..574
                       mol_type = protein
                       organism = unidentified
```

```
                         note = Respiratory syncytial virus
SEQUENCE: 63
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGYSVLTF KVLDLKNYID KQLLPILNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 64            moltype = AA  length = 574
FEATURE                  Location/Qualifiers
source                   1..574
                         mol_type = protein
                         organism = unidentified
                         note = Respiratory syncytial virus
SEQUENCE: 64
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKTTNVTLS KKRKRRFLGF LLGVGSAIAS GIAVSKVLHL EGEVNKIKSA LLSTNKAVVS  180
LSNGYSVLTF KVLDLKNYID KQLLPILNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNTDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                             574

SEQ ID NO: 65            moltype = AA  length = 574
FEATURE                  Location/Qualifiers
source                   1..574
                         mol_type = protein
                         organism = unidentified
                         note = Respiratory syncytial virus
SEQUENCE: 65
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST QAANSRARRE LPRFMNYTLN  120
NTKNTNVTLS KKRKRRFLGF LLGVGSAIAS GIAVSKVLHL EGEVNKIKSA LLSTNKAVVS  180
LSNGYSVLTF KVLDLKNYID KQLLPILNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 66            moltype = AA  length = 574
FEATURE                  Location/Qualifiers
source                   1..574
                         mol_type = protein
                         organism = unidentified
                         note = Respiratory syncytial virus
SEQUENCE: 66
MELLVHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTNNLNVSIS KKRKRRFLGF LLGVGSAIAS GIAVSKVLHL EGEVNKIKNA LLSTNKAVVS  180
LSNGYSVLTF KVLDLKNYIN NQLLPILNQQ SCRISNIETV IEFQQYNSRL LEIAREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 67            moltype = AA  length = 574
FEATURE                  Location/Qualifiers
source                   1..574
                         mol_type = protein
                         organism = unidentified
                         note = Respiratory syncytial virus
SEQUENCE: 67
MELPILKTNA ITTILTAVTF CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGYSVLTF KVLDLKNYID KQLLPILNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
```

-continued

```
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLLLYC KARSTPVTLS KDQLSGINNI AFSN                              574

SEQ ID NO: 68          moltype = AA  length = 574
FEATURE                Location/Qualifiers
source                 1..574
                       mol_type = protein
                       organism = unidentified
                       note = Respiratory syncytial virus
SEQUENCE: 68
MELPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGYSVLTF KVLDLKNYID KQLLPILNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KEQLSGINNI AFSN                              574

SEQ ID NO: 69          moltype = AA  length = 574
FEATURE                Location/Qualifiers
source                 1..574
                       mol_type = protein
                       organism = unidentified
                       note = Respiratory syncytial virus
SEQUENCE: 69
MELPILKTNA ITTIFAAVTL CFASSQNITE EFYQSTCSAV SKGYLSALRT GWYTSVITVE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGYSVLTF KVLDLKNYID KQLLPILNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 70          moltype = AA  length = 568
FEATURE                Location/Qualifiers
source                 1..568
                       mol_type = protein
                       organism = unidentified
                       note = Respiratory syncytial virus
SEQUENCE: 70
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGYSVLTF KVLDLKNYID KQLLPILNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHSA WSHPQFEK                                    568

SEQ ID NO: 71          moltype = AA  length = 574
FEATURE                Location/Qualifiers
source                 1..574
                       mol_type = protein
                       organism = unidentified
                       note = Respiratory syncytial virus
SEQUENCE: 71
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTF KVLDLKNYIN NRLLPILNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                              574

SEQ ID NO: 72          moltype = AA  length = 574
```

```
FEATURE                 Location/Qualifiers
source                  1..574
                        mol_type = protein
                        organism = unidentified
                        note = Respiratory syncytial virus
SEQUENCE: 72
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTF KVLDLKNYIN NQLLPILNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                            574

SEQ ID NO: 73           moltype = AA  length = 573
FEATURE                 Location/Qualifiers
source                  1..573
                        mol_type = protein
                        organism = unidentified
                        note = Respiratory syncytial virus
SEQUENCE: 73
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTF KVLDLKNYIN NQLLPILNKQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DVSSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFS                             573

SEQ ID NO: 74           moltype = AA  length = 574
FEATURE                 Location/Qualifiers
source                  1..574
                        mol_type = protein
                        organism = unidentified
                        note = Respiratory syncytial virus
SEQUENCE: 74
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PVANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTF KVLDLKNYIN NQLLPILNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNTKEGS NICLTRTDRG WYCDNAGSVS FFPQADTCKV  360
QSNRVFCDTM YSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                            574

SEQ ID NO: 75           moltype = AA  length = 574
FEATURE                 Location/Qualifiers
source                  1..574
                        mol_type = protein
                        organism = unidentified
                        note = Respiratory syncytial virus
SEQUENCE: 75
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GMAVSKVLHL EGEVNKIKNA LLSTNKAVVS  180
LSNGYSVLTF KVLDLKNYIN NRLLPILNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                            574

SEQ ID NO: 76           moltype = AA  length = 574
FEATURE                 Location/Qualifiers
source                  1..574
                        mol_type = protein
                        organism = unidentified
                        note = Respiratory syncytial virus
SEQUENCE: 76
MELLIHRSSA IFLTLAINAL YLTSSQNITE EFYQSTCSAV SRGYFSALRT GWYTSVITIE  60
```

-continued

```
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTF KVLDLKNYIN NQLLPILNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IVIIVVLLS  540
LIAIGLLLYC KAKNTPVTLS KDQLSGINNI AFSK                              574

SEQ ID NO: 77          moltype = AA  length = 573
FEATURE                Location/Qualifiers
source                 1..573
                       mol_type = protein
                       organism = unidentified
                       note = Respiratory syncytial virus
SEQUENCE: 77
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTF KVLDLKNYIN NQLLPILNKQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DVSSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IVIIVVLLS  540
LIAIGLLLYC KAKNTPVTLS KDQLSGINNI AFS                               573

SEQ ID NO: 78          moltype = AA  length = 574
FEATURE                Location/Qualifiers
source                 1..574
                       mol_type = protein
                       organism = unidentified
                       note = Respiratory syncytial virus
SEQUENCE: 78
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PVANNRARRE APQYMNYTIN  120
TTKNLNVSIS KKRKRRFLGF LLGVGSAIAS GIAVSKVLHL EGEVNKIKNA LLSTNKAVVS  180
LSNGYSVLTF KVLDLKNYIN NQLLPILNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNTKEGS NICLTRTDRG WYCDNAGSVS FFPQADTCKV  360
QSNRVFCDTM YSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IVIIVVLLS  540
LIAIGLLLYC KAKNTPVTLS KDQLSGINNI AFSK                              574

SEQ ID NO: 79          moltype = AA  length = 574
FEATURE                Location/Qualifiers
source                 1..574
                       mol_type = protein
                       organism = unidentified
                       note = Respiratory syncytial virus
SEQUENCE: 79
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GMAVSKVLHL EGEVNKIKNA LLSTNKAVVS  180
LSNGYSVLTF KVLDLKNYIN NRLLPILNQQ SCRISNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IVIIVVLLS  540
LIAIGLLLYC KAKNTPVTLS KDQLSGINNI AFSK                              574

SEQ ID NO: 80          moltype = AA  length = 574
FEATURE                Location/Qualifiers
source                 1..574
                       mol_type = protein
                       organism = unidentified
                       note = Respiratory syncytial virus
SEQUENCE: 80
MELLIHRSSA IFLTLAINAL YLTSSQNITE EFYQSTCSAV SRGYFSALRT GWYTSVITIE  60
LSNITETKCN GTDTKVKLIK QELDKYKNAV TELQLLMQNT PAANNRARRE APQHMNYTIN  120
TTKNLNVSIS KKRKRRFLGF LLGVGSAIAS GIAVSKVLHL EGEVNKIKNA LLSTNKAVVS  180
LSNGYSVLTF KVLDLKNYIN NQLLPILNQQ SCRIFNIETV IEFQQYNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKYRG IIKTFSNGCD YVSNKGVDTV SVGNTLYYVN KLEGKNLYVK GEPIINYYDP  480
```

-continued

```
LVFPSDEFDA SISQVNEKIN QSLAFIRKSD ELLHNVNTGK STTNIMITTI IIVIIVVLLS  540
LIAIGLLLYC KAKNTPVTLS KDQLSGINNI AFSK                              574

SEQ ID NO: 81          moltype = AA  length = 568
FEATURE                Location/Qualifiers
source                 1..568
                       mol_type = protein
                       organism = unidentified
                       note = Respiratory syncytial virus
SEQUENCE: 81
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGYSVLTF KVLDLKNYID KQLLPILNKQ SCSISNIETV IEFQQYNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKYRG IIKTFSNGCD YVSNKGVDTV SVGNTLYYVN KQEGKSLYVK GEPIINFYDP  480
LVFPSDEFDA SISQVNEKIN QSLAFIRKSD EVVSAIGGFI PEAPRDGQAY VRKDGEWVLL  540
STFLGGLVPR GSHHHHHHSA WSHPQFEK                                     568

SEQ ID NO: 82          moltype = AA  length = 568
FEATURE                Location/Qualifiers
source                 1..568
                       mol_type = protein
                       organism = unidentified
                       note = Respiratory syncytial virus
SEQUENCE: 82
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHSA WSHPQFEK                                     568

SEQ ID NO: 83          moltype = AA  length = 574
FEATURE                Location/Qualifiers
source                 1..574
                       mol_type = protein
                       organism = unidentified
                       note = Respiratory syncytial virus
SEQUENCE: 83
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNTGK STTNIMITTI IIVIIVVLLS  540
LIAIGLLLYC KAKNTPVTLS KDQLSGINNI AFSK                              574

SEQ ID NO: 84          moltype = AA  length = 568
FEATURE                Location/Qualifiers
source                 1..568
                       mol_type = protein
                       organism = unidentified
                       note = Respiratory syncytial virus
SEQUENCE: 84
MELLIHRSSA IFLTLAINAL YLTSSQNITE EFYQSTCSAV SRGYFSALRT GWYTSVITIE  60
LSNITETKCN GTDTKVKLIK QELDKYKNAV TELQLLMQNT PAANNRARRE APQHMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRIFNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRKSD ELLSAIGGYI PEAPRDGQAY VRKDGEWVLL  540
STFLGGLVPR GSHHHHHHSA WSHPQFEK                                     568

SEQ ID NO: 85          moltype = AA  length = 574
FEATURE                Location/Qualifiers
source                 1..574
                       mol_type = protein
```

```
                          organism = unidentified
                          note = Respiratory syncytial virus
SEQUENCE: 85
MELLIHRSSA IFLTLAINAL YLTSSQNITE EFYQSTCSAV SRGYFSALRT GWYTSVITIE  60
LSNITETKCN GTDTKVKLIK QELDKYKNAV TELQLLMQNT PAANNRARRE APQHMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRIFNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRKSD ELLHNVNTGK STTNIMITTI IIVIIVVLLS  540
LIAIGLLLYC KAKNTPVTLS KDQLSGINNI AFSK                             574

SEQ ID NO: 86             moltype = AA  length = 568
FEATURE                   Location/Qualifiers
source                    1..568
                          mol_type = protein
                          organism = unidentified
                          note = Respiratory syncytial virus
SEQUENCE: 86
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHSA WSHPQFEK                                    568

SEQ ID NO: 87             moltype = AA  length = 574
FEATURE                   Location/Qualifiers
source                    1..574
                          mol_type = protein
                          organism = unidentified
                          note = Respiratory syncytial virus
SEQUENCE: 87
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNTGK STTNIMITTI IIVIIVVLLS  540
LIAIGLLLYC KAKNTPVTLS KDQLSGINNI AFSK                             574

SEQ ID NO: 88             moltype = AA  length = 568
FEATURE                   Location/Qualifiers
source                    1..568
                          mol_type = protein
                          organism = unidentified
                          note = Respiratory syncytial virus
SEQUENCE: 88
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHSA WSHPQFEK                                    568

SEQ ID NO: 89             moltype = AA  length = 574
FEATURE                   Location/Qualifiers
source                    1..574
                          mol_type = protein
                          organism = unidentified
                          note = Respiratory syncytial virus
SEQUENCE: 89
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTF KVLDLKNYID KQLLPILNKQ SCSISNIETV IEFQQKNNRL LEITREFSVN  240
```

-continued

```
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNTGK STTNIMITTI IIVIIVVLLS  540
LIAIGLLLYC KAKNTPVTLS KDQLSGINNI AFSK                            574

SEQ ID NO: 90          moltype = AA  length = 568
FEATURE                Location/Qualifiers
source                 1..568
                       mol_type = protein
                       organism = unidentified
                       note = Respiratory syncytial virus
SEQUENCE: 90
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHSA WSHPQFEK                                  568

SEQ ID NO: 91          moltype = AA  length = 574
FEATURE                Location/Qualifiers
source                 1..574
                       mol_type = protein
                       organism = unidentified
                       note = Respiratory syncytial virus
SEQUENCE: 91
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNTGK STTNIMITTI IIVIIVVLLS  540
LIAIGLLLYC KAKNTPVTLS KDQLSGINNI AFSK                            574

SEQ ID NO: 92          moltype = AA  length = 55
FEATURE                Location/Qualifiers
REGION                 1..55
                       note = Description of Artificial Sequence: Synthetic
                        polypeptide
source                 1..55
                       mol_type = protein
                       organism = synthetic construct
SEQUENCE: 92
SAIGGYIPEA PRDGQAYVRK DGEWVLLSTF LGGLVPRGSH HHHHHSAWSH PQFEK       55

SEQ ID NO: 93          moltype = AA  length = 27
FEATURE                Location/Qualifiers
REGION                 1..27
                       note = Description of Artificial Sequence: Synthetic peptide
source                 1..27
                       mol_type = protein
                       organism = synthetic construct
SEQUENCE: 93
GYIPEAPRDG QAYVRKDGEW VLLSTFL                                   27

SEQ ID NO: 94          moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 94
LVPRGS                                                          6

SEQ ID NO: 95          moltype = AA  length = 6
FEATURE                Location/Qualifiers
REGION                 1..6
                       note = Description of Artificial Sequence: Synthetic 6xHis
                        tag
```

-continued

```
source                  1..6
                        mol_type = protein
                        organism = synthetic construct
SEQUENCE: 95
HHHHHH                                                                    6

SEQ ID NO: 96           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 96
WSHPQFEK                                                                  8
```

We claim:

1. A mutant RSV F molecule comprising: (a) an F2 polypeptide comprising amino acid residues 26-109 of SEQ ID NO 81, and (b) an F1 polypeptide comprising amino acid residues 137-513 of SEQ ID NO 81; wherein the F2 polypeptide is linked to the F1 polypeptide by a disulfide bond.

2. The mutant RSV F molecule of claim 1, wherein the molecule binds to a pre-fusion specific antibody.

3. The mutant RSV F molecule of claim 1, wherein the molecule binds to an antibody selected from the group consisting of D25, 5C4, AM22 and AM14.

4. The mutant RSV F molecule of claim 1, wherein the molecule further comprises one or more tags useful for detection or purification of the RSV F molecule.

5. The mutant RSV F molecule of claim 4, wherein the tag is selected from the group consisting of: Strep tags, Strep II tags, FLAG tags, glutathione S-transferase tags, green fluorescent proteintags, hemagglutinin A tags, histidine tags, luciferase tags, maltose-binding protein tags, c-Myc tags, protein A tags, and protein G tags.

6. The mutant RSV F molecule of claim 4, wherein the tag comprises SEQ ID NO. 95.

7. The mutant RSV F molecule of claim 4, wherein the tag comprises SEQ ID NO. 96.

8. The mutant RSV F molecule of claim 4, wherein the tag is a proteolytically cleavable tag.

9. A soluble, mature trimeric RSVF molecule consisting of three monomers, wherein each monomer comprises (a) an F2 polypeptide comprising amino acid residues 26-109 of SEQ ID NO 81, and (b) an F1 polypeptide comprising amino acid residues 137-513 of SEQ ID NO. 81, and (c) a heterologous trimerization domain, wherein the F2 polypeptide is linked to the F1 polypeptide by a disulfide bond.

10. The RSV F molecule of claim 9, wherein the heterologous trimerization domain is a foldon domain, a GCN4 domain, or a T4 fibrinitin domain.

11. The RSV F molecule of claim 9, wherein the heterologous trimerization domain comprises SEQ ID NO. 93.

12. The RSVF molecule of claim 9, wherein the molecule comprises one or more DT cross links and is stabilized in the pre-F conformation.

13. The RSVF molecule of claim 10, wherein the molecule comprises one or more DT cross links and is stabilized in the pre-F conformation.

14. The RSVF molecule of claim 11, wherein the molecule comprises one or more DT cross links and is stabilized in the pre-F conformation.

15. A pharmaceutical composition comprising the RSV molecule of claim 9.

16. A pharmaceutical composition comprising the RSV molecule of claim 10.

17. A pharmaceutical composition comprising the RSV molecule of claim 11.

18. A pharmaceutical composition comprising the RSV molecule of claim 12.

19. A pharmaceutical composition comprising the RSV molecule of claim 13.

20. A pharmaceutical composition comprising the RSV molecule of claim 14.

* * * * *